(12) United States Patent
Petrukhin et al.

(10) Patent No.: US 12,168,664 B2
(45) Date of Patent: Dec. 17, 2024

(54) TRIAZOLOPYRIMIDINES, THEIR PREPARATION AND USE

(71) Applicants: Konstantin Petrukhin, New Windsor, NY (US); Kirsten Alison Rinderspacher, Mount Vernon, NY (US); Shi-Xian Deng, White Plains, NY (US); Andras Varadi, New York, NY (US); Boglarka Racz, New York, NY (US); Peter Bernstein, Philadelphia, PA (US); Patricia C. Weber, Yardley, PA (US); Donald W. Landry, New York, NY (US); Andrew S. Wasmuth, Brooklyn, NY (US)

(72) Inventors: Konstantin Petrukhin, New Windsor, NY (US); Kirsten Alison Rinderspacher, Mount Vernon, NY (US); Shi-Xian Deng, White Plains, NY (US); Andras Varadi, New York, NY (US); Boglarka Racz, New York, NY (US); Peter Bernstein, Philadelphia, PA (US); Patricia C. Weber, Yardley, PA (US); Donald W. Landry, New York, NY (US); Andrew S. Wasmuth, Brooklyn, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 1009 days.

(21) Appl. No.: 17/085,791

(22) Filed: Oct. 30, 2020

(65) Prior Publication Data

US 2021/0047337 A1 Feb. 18, 2021

Related U.S. Application Data

(63) Continuation of application No. PCT/US2019/030172, filed on May 1, 2019.

(Continued)

(51) Int. Cl.
C07D 487/04 (2006.01)
A61P 27/02 (2006.01)
C07D 519/00 (2006.01)

(52) U.S. Cl.
CPC ............ C07D 487/04 (2013.01); A61P 27/02 (2018.01); C07D 519/00 (2013.01)

(58) Field of Classification Search
CPC ...... C07D 519/00; C07D 487/04; A61P 27/02
See application file for complete search history.

(56) References Cited

U.S. PATENT DOCUMENTS

2017/0247327 A1 8/2017 Petrukhin et al.

FOREIGN PATENT DOCUMENTS

WO WO 2014/152013 A1 9/2014

OTHER PUBLICATIONS

International Search Report issued Sep. 13, 2019 in connection with PCT International Application No. PCT/US2019/030172.

(Continued)

*Primary Examiner* — Marcos L Sznaidman
(74) *Attorney, Agent, or Firm* — Gary J. Gershik

(57) ABSTRACT

The present invention provides a compound having the structure:

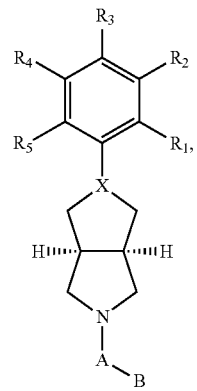

wherein $R_1$, $R_2$, $R_3$, $R_4$, and $R_5$ are each independently H, halogen, $CF_3$, $C_1$-$C_4$ alkyl, aryl or heteroaryl; X is N or $CR_6$, wherein $R_6$ is H, OH, or halogen; A is absent or present, and when present is

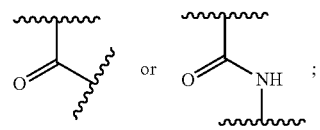

B has the structure:

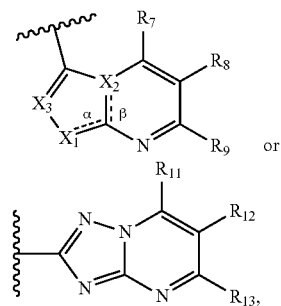

or a pharmaceutically acceptable salt thereof.

20 Claims, 12 Drawing Sheets

Related U.S. Application Data

(60) Provisional application No. 62/665,047, filed on May 1, 2018.

(56) References Cited

OTHER PUBLICATIONS

Written Opinion (form PCT/ISA/237) issued Sep. 13, 2019 in connection with PCT International Application No. PCT/US2019/030172.

International Preliminary Report on Patentability issued Nov. 3, 2020, including Written Opinion of the International Searching Authority issued Sep. 13, 2019, in connection with PCT International Application No. PCT/US2019/030172.

all-*trans*-retinal dimer-phosphatidylethanolamine all-*trans*-retinal dimer

TRIAZOLOPYRIMIDINES, THEIR PREPARATION AND USE

CROSS-REFERENCE TO RELATED APPLICATIONS

This application is a continuation of PCT/US2019/030172, filed May 1, 2019, claiming priority of U.S. Provisional Application No. 62/665,047, filed May 1, 2018, the contents of each of which are hereby incorporated by reference herein.

GOVERNMENT SUPPORT

This invention was made with government support under Grant number NS074476 awarded by the National Institutes of Health. The government has certain rights in the invention.

Throughout this application, certain publications are referenced in parentheses. Full citations for these publications may be found immediately preceding the claims. The disclosures of these publications in their entireties are hereby incorporated by reference into this application in order to describe more fully the state of the art to which this invention relates.

BACKGROUND OF THE INVENTION

Age-related macular degeneration (AMD) is the leading cause of blindness in developed countries. It is estimated that 62.9 million individuals worldwide have the most prevalent atrophic (dry) form of AMD; 8 million of them are Americans. Due to increasing life expectancy and current demographics, this number is expected to triple by 2020. There is currently no FDA-approved treatment for dry AMD. Given the lack of treatment and high prevalence, development of drugs for dry AMD is of utmost importance. Clinically, atrophic AMD represents a slowly progressing neurodegenerative disorder in which specialized neurons (rod and cone photoreceptors) die in the central part of the retina called macula (1). Histopathological and clinical imaging studies indicate that photoreceptor degeneration in dry AMD is triggered by abnormalities in the retinal pigment epithelium (RPE) that lies beneath photoreceptors and provides critical metabolic support to these light-sensing neuronal cells. Experimental and clinical data indicate that excessive accumulation of cytotoxic autofluorescent lipid-protein-retinoid aggregates (lipofuscin) in the RPE is a major trigger of dry AMD (2-9). In addition to AMD, dramatic accumulation of lipofuscin is the hallmark of Stargardt Disease (STGD), an inherited form of juvenile-onset macular degeneration. The major cytotoxic component of RPE lipofuscin is pyridinium bisretinoid A2E (FIG. 1). Additional cytotoxic bisretinoids are isoA2E, atRAL di-PE, and A2-DHP-PE (40, 41). Formation of A2E and other lipofuscin bisretinoids, such as A2-DHP-PE (A2-dihydropyridine-phosphatidylethanolamine) and atRALdi-PE (all-trans-retinal dimer-phosphatidylethanolamine), begins in photoreceptor cells in a non-enzymatic manner and can be considered as a by-product of the properly functioning visual cycle.

A2E is a product of condensation of all-trans retinaldehyde with phosphatidyl-ethanolamine which occurs in the retina in a non-enzymatic manner and, as illustrated in FIG. 4, can be considered a by-product of a properly functioning visual cycle (10). Light-induced isomerization of 11-cis retinaldehyde to its all-trans form is the first step in a signaling cascade that mediates light perception. The visual cycle is a chain of biochemical reactions that regenerate visual pigment (11-cis retinaldehyde conjugated to opsin) following exposure to light.

As cytotoxic bisretinoids are formed during the course of a normally functioning visual cycle, partial pharmacological inhibition of the visual cycle may represent a treatment strategy for dry AMD and other disorders characterized by excessive accumulation of lipofuscin (25-27, 40, 41).

SUMMARY OF THE INVENTION

The present invention provides a compound having the structure:

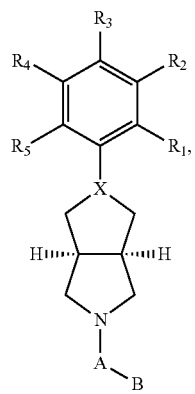

wherein
$R_1$, $R_2$, $R_3$, $R_4$, and $R_5$ are each independently H, halogen, $CF_3$, $OCF_3$, alkyl, haloalkyl, aryl or heteroaryl;
X is N or $CR_6$,
  wherein $R_6$ is H, OH, or halogen;
A is absent or present, and when present is

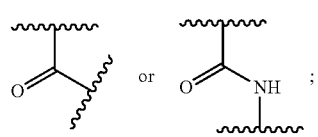

B has the structure:

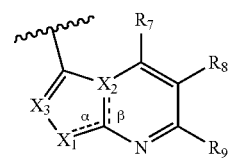

wherein
α and β are each a bond that is present or absent;
$X_1$ is N, NH or $NR_{10}$,
  wherein $R_{10}$ is alkyl, alkenyl or alkynyl;
$X_2$ is C or N;
$X_3$ is CH or N;
$R_7$, $R_8$ and $R_9$ are each, independently, H, halogen, alkyl, alkenyl, alkynyl, alkyl-OH, alkyl-$NH_2$, alkyl-OAc alkyl-O(CO)-alkyl, alkyl-O-alkyl, haloalkyl, cycloalkyl, O-alkyl, NH-alkyl, C(O)OH, C(O)—$NH_2$, C(O)—N($CH_3$)$_2$, C(O)—$NHCH_3$, NHC(O)—N($CH_3$)$_2$, CN or $CF_3$, wherein $X_1$, $X_2$ and $X_3$ are each N, α is present and β is absent; or $X_1$ is NH, $X_2$ is C, $X_3$ is CH, α is absent and β is present; or $X_1$ is N, $X_2$ is N, $X_3$ is CH, α is present and β is absent; or $X_1$ is NH or $NR_{10}$, $X_2$ is C, $X_3$ is N, α is absent and β is present, wherein when $X_1$ is NH, $X_2$ is C, $X_3$ is N, α is absent and β is present, then one of $R_7$, $R_8$ and $R_9$ is other than H, or B has the structure:

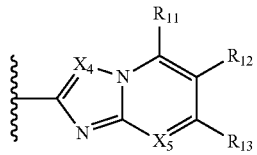

wherein $X_4$ and $X_5$ are each, independently, is N or CH; and $R_{11}$, $R_{12}$ and $R_{13}$ are each, independently, H, halogen, alkyl, alkenyl, alkynyl alkyl-OH, alkyl-$NH_2$, alkyl-OAc, alkyl-O(CO)-alkyl, alkyl-O-alkyl, haloalkyl, cycloalkyl, O-alkyl, NH-alkyl, C(O)OH, C(O)—$NH_2$, C(O)—N($CH_3$)$_2$, C(O)—$NHCH_3$, NHC(O)—N($CH_3$)$_2$, CN or $CF_3$, or a pharmaceutically acceptable salt thereof.

BRIEF DESCRIPTION OF THE FIGURES

FIG. 9D: Dose-dependent RBP4 reduction after oral dosing of 7a.

FIG. 11: Serum RPB4 levels in three groups of mice at baseline and at end of 8-week treatment period with 7a.

DETAILED DESCRIPTION OF THE INVENTION

Figure 1:
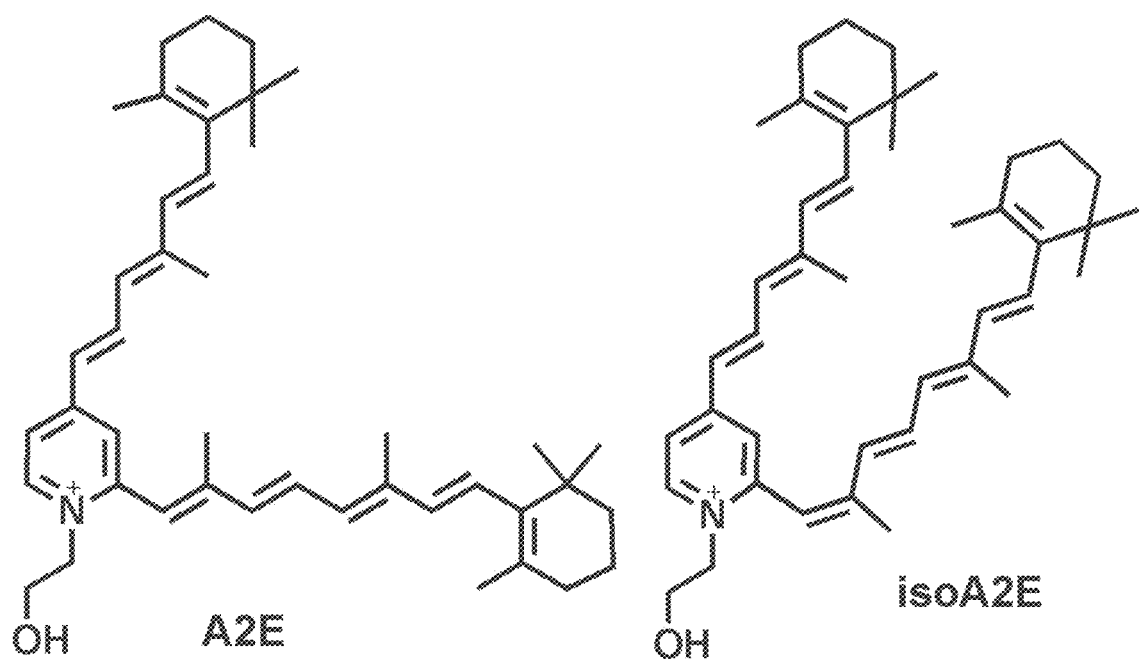
FIG. 1. Structure of bisretinoid A2F, a cytotoxic component of retinal lipofuscin.

The present invention provides a compound having the structure:

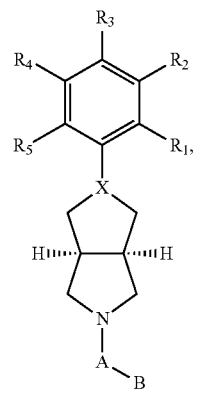

wherein $R_1$, $R_2$, $R_3$, $R_4$, and $R_5$ are each independently H, halogen, $CF_3$, $OCF_3$, alkyl, haloalkyl, aryl or heteroaryl;

X is N or $CR_6$, wherein $R_6$ is H, OH, or halogen;

A is absent or present, and when present is

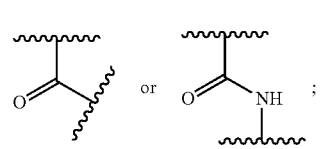

B has the structure:

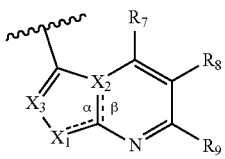

wherein
α and β are each a bond that is present or absent;
$X_1$ is N, NH or $NR_{10}$,
   wherein $R_{10}$ is alkyl, alkenyl or alkynyl;
$X_2$ is C or N;
$X_3$ is CH or N;
$R_7$, $R_8$ and $R_9$ are each, independently, H, halogen, alkyl, alkenyl, alkynyl, alkyl-OH, alkyl-$NH_2$, alkyl-OAc alkyl-O(CO)-alkyl, alkyl-O-alkyl, haloalkyl, cycloalkyl, O-alkyl, NH-alkyl, C(O)OH, C(O)—$NH_2$, C(O)—N(CH$_3$)$_2$, C(O)—NHCH$_3$, NHC(O)—N(CH$_3$)$_2$, CN or CF$_3$,
wherein
$X_1$, $X_2$ and $X_3$ are each N, α is present and β is absent; or
$X_1$ is NH, $X_2$ is C, $X_3$ is CH, α is absent and β is present; or
$X_1$ is N, $X_2$ is N, $X_3$ is CH, α is present and β is absent; or
$X_1$ is NH or $NR_{10}$, $X_2$ is C, $X_3$ is N, α is absent and β is present, wherein
   when $X_1$ is NH, $X_2$ is C, $X_3$ is N, α is absent and β is present, then one of $R_7$, $R_8$ and $R_9$ is other than H,
or B has the structure:

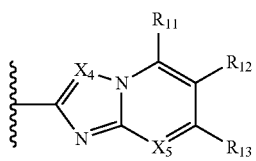

wherein
$X_4$ and $X_5$ are each, independently, is N or CH; and
$R_{11}$, $R_{12}$ and $R_{13}$ are each, independently, H, halogen, alkyl, alkenyl, alkynyl alkyl-OH, alkyl-$NH_2$, alkyl-OAc, alkyl-O(CO)-alkyl, alkyl-O-alkyl, haloalkyl, cycloalkyl, O-alkyl, NH-alkyl, C(O)CH, C(O)—$NH_2$, C(O)—N(CH$_3$)$_2$, C(O)—NHCH$_3$, NHC(O)—N(CH$_3$)$_2$, CN or CF$_3$,
or a pharmaceutically acceptable salt thereof.

In one embodiment of the above compound, wherein $R_1$, $R_2$, $R_3$, $R_4$, and $R_5$ are each independently H, halogen, CF$_3$ or $C_1$-$C_4$ alkyl.

In one embodiment of the above compound, B has the structure:

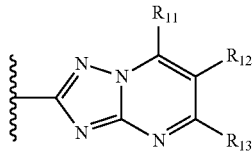

wherein
$R_{12}$ and $R_{13}$ are each, independently, H, halogen, alkyl, alkenyl, alkynyl alkyl-OH, alkyl-$NH_2$, alkyl-OAc, alkyl-O(CO)-alkyl, alkyl-O-alkyl, haloalkyl, cycloalkyl, O-alkyl, NH-alkyl, C(O)OH, C(O)—$NH_2$, C(O)—N(CH$_3$)$_2$, C(O)—NHCH$_3$, NHC(O)—N(CH$_3$)$_2$, CN or CF$_3$.

The present invention also provides a compound having the structure:

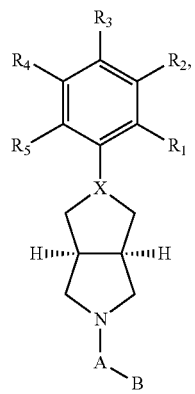

wherein
$R_1$, $R_2$, $R_3$, $R_4$, and $R_5$ are each independently H, halogen, CF$_3$ or $C_1$-$C_4$ alkyl;
X is N or CR$_6$,
   wherein $R_6$ is H, OH, or halogen;
A is absent or present, and when present is

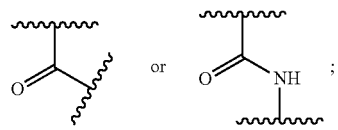

B has the structure:

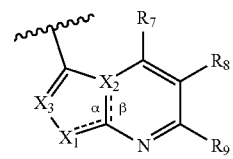

wherein
α and β are each a bond that is present or absent;
$X_1$ is N, NH or NR$^{10}$,
   wherein $R_{10}$ is alkyl, alkenyl or alkynyl;
$X_2$ is C or N;
$X_3$ is CH or N;
$R_7$, $R_8$ and $R_9$ are each, independently, H, halogen, alkyl, alkenyl, alkynyl, alkyl-OH, alkyl-$NH_2$, alkyl-OAc alkyl-O(CO)-alkyl, alkyl-O-alkyl, haloalkyl, cycloalkyl, O-alkyl, NH-alkyl, C(O)OH, C(O)—$NH_2$, C(O)—N(CH$_3$)$_2$, C(O)—NHCH$_3$, NHC(O)—N(CH$_3$)$_2$, CN or CF$_3$,
wherein
$X_1$, $X_2$ and $X_3$ are each N, α is present and β is absent; or
$X_1$ is NH, $X_2$ is C, $X_3$ is CH, α is absent and β is present; or $X_1$ is N, $X_2$ is N, $X_3$ is CH, α is present and β is absent; or $X_1$ is NH or $NR_{10}$, $X_2$ is C, $X_3$ is N, α is absent and β is present, wherein when $X_1$ is NH, $X_2$ is C, $X_3$ is N, α is absent and β is present, then one of $R_7$, $R_8$ and $R_9$ is other than H, or B has the structure:

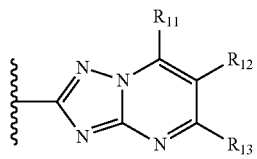

wherein $R_{11}$, $R_{12}$ and $R_{13}$ are each, independently, H, halogen, alkyl, alkenyl, alkynyl alkyl-OH, alkyl-$NH_2$, alkyl-OAc, alkyl-O(CO)-alkyl, alkyl-O-alkyl, haloalkyl, cycloalkyl, O-alkyl, NH-alkyl, C(O)OH, C(O)—$NH_2$, C(O)—$N(CH_3)_2$, C(O)—$NHCH_3$, NHC(O)—$N(CH_3)_2$, CN or $CF_3$, or a pharmaceutically acceptable salt thereof.

In some embodiments, the compound having the structure:

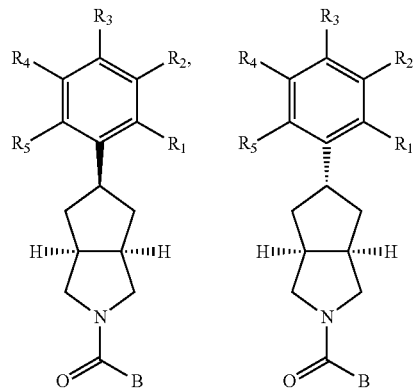

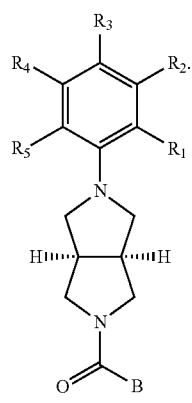

In some embodiments, the compound having the structure:

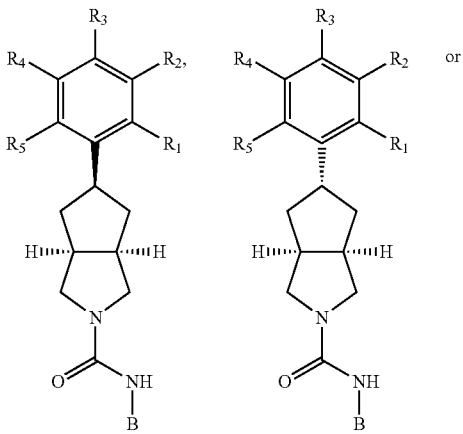

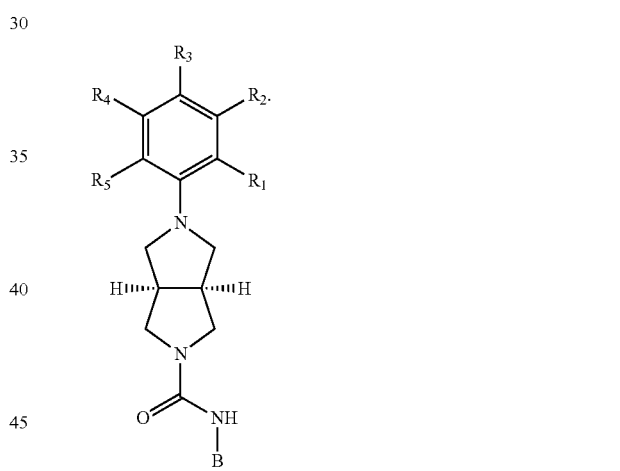

In some embodiments, the compound having the structure:

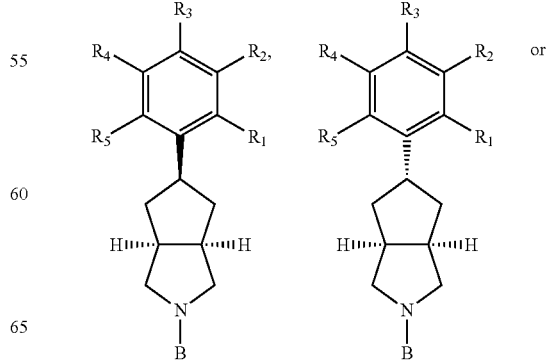

-continued

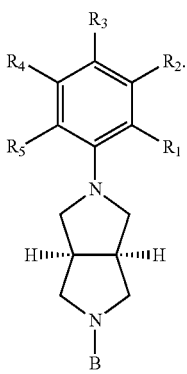

The present invention also provides a compound having the structure:

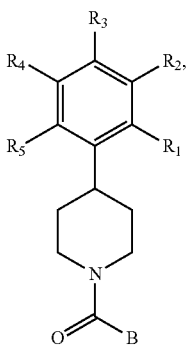

wherein
R₁, R₂, R₃, R₄, and R₅ are each independently H, halogen, CF₃, OCF₃, alkyl, haloalkyl, aryl or heteroaryl; and
B has the structure:

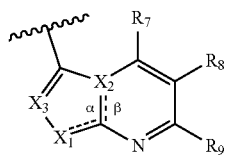

wherein
α and β are each a bond that is present or absent;
$X_1$ is N, NH or NR$_{10}$,
  wherein R$_{10}$ is alkyl, alkenyl or alkynyl;
$X_2$ is C or N;
$X_3$ is CH or N;
R₇, R₈ and R₉ are each, independently, H, halogen, alkyl, alkenyl, alkynyl, alkyl-OH, alkyl-NH₂, alkyl-OAc, alky-O-alkyl, haloalkyl, cycloalkyl, O-alkyl, NH-alkyl, C(O)OH, C(O)—NH₂, C(O)—N(CH₃)₂, C(O)—NHCH₃, NHC(O)—N(CH₃)₂, CN, or CF₃,
wherein
$X_1$, $X_2$ and $X_3$ are each N, α is present and β is absent; or
$X_1$ is NH, $X_2$ is C, $X_3$ is CH, α is absent and β is present; or
$X_1$ is N, $X_2$ is N, $X_3$ is CH, α is present and β is absent; or
$X_1$ is NH or NR$_{10}$, $X_2$ is C, $X_3$ is N, α is absent and β is present, wherein when $X_1$ is NH, $X_2$ is C, $X_3$ is N, α is absent and β is present, then one of R₇, R₈ and R₉ is other than H,
or B has the structure:

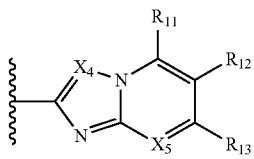

Wherein
$X_4$ and $X_5$ are each, independently, is N or CH; and
R₁₁, R₁₂ and R₁₃ are each, independently, H, halogen, alkyl, alkyl-OH, alkyl-NH₂, alkyl-OAc, alky-O-alkyl, haloalkyl, cycloalkyl, O-alkyl, NH-alkyl, C(O)OH, C(O)—NH₂, C(O)—N(CH₃)₂, C(O)—NHCH₃, NHC(O)—N(CH₃)₂, CN, or CF₃,
or a pharmaceutically acceptable salt thereof.

In one embodiment of the above compound, wherein R₁, R₂, R₃, R₄, and R₅ are each independently H, halogen, CF₃ or C₁-C₄ alkyl.

In one embodiment of the above compound, B has the structure:

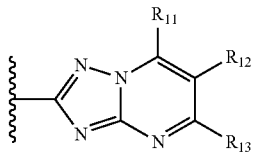

wherein
$R^{11}$, $R^{12}$ and R₁₃ are each, independently, H, halogen, alkyl, alkenyl, alkynyl alkyl-OH, alkyl-NH₂, alkyl-OAc, alkyl-O(CO)-alkyl, alkyl-O-alkyl, haloalkyl, cycloalkyl, O-alkyl, NH-alkyl, C(O)OH, C(O)—NH₂, C(O)—N(CH₃)₂, C(O)—NHCH₃, NHC(O)—N(CH₃)₂, CN or CF₃.

The present invention also provides a compound having the structure:

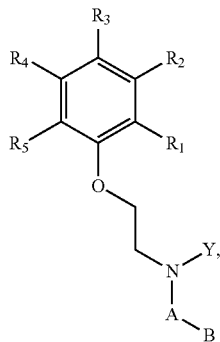

wherein
R₁, R₂, R₃, R₄, and R₅ are each independently H, halogen, CF₃, OCF₃, alkyl, haloalkyl, aryl or heteroaryl;
Y is alkyl;

A is absent or present, and when present is

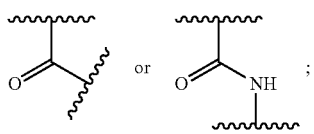

and

B has the structure:

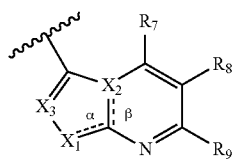

wherein

α and β are each a bond that is present or absent;
$X_1$ is N, NH or $NR_{10}$,
  wherein $R_{10}$ is alkyl, alkenyl or alkynyl;
$X_2$ is C or N;
$X_3$ is CH or N;
$R_7$, $R_8$ and $R_9$ are each, independently, H, halogen, alkyl, alkenyl, alkynyl, alkyl-OH, alkyl-$NH_2$, alkyl-OAc, alky-O-alkyl, haloalkyl, cycloalkyl, O-alkyl, NH-alkyl, C(O)OH, C(O)—$NH_2$, C(O)—$N(CH_3)_2$, C(O)—$NHCH_3$, NHC(O)—$N(CH_3)_2$, CN, or $CF_3$,
wherein
$X_1$, $X_2$ and $X_3$ are each N, α is present and β is absent; or
$X_1$ is NH, $X_2$ is C, $X_3$ is CH, α is absent and β is present; or
$X_1$ is N, $X_2$ is N, $X_3$ is CH, α is present and β is absent; or
$X_1$ is NH or $NR_{10}$, $X_2$ is C, $X_3$ is N, α is absent and β is present, wherein
  when $X_1$ is NH, $X_2$ is C, $X_3$ is N, α is absent and β is present, then one of $R_7$, $R_8$ and $R_9$ is other than H,
or B has the structure:

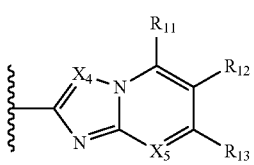

wherein
$X_4$ and $X_5$ are each, independently, is N or CH; and
$R_{11}$, $R_{12}$ and $R_{13}$ are each, independently, H, halogen, alkyl, alkyl-OH, alkyl-$NH_2$, alkyl-OAc, alky-O-alkyl, haloalkyl, cycloalkyl, O-alkyl, NH-alkyl, C(O)OH, C(O)—$NH_2$, C(O)—$N(CH_3)_2$, C(O)—$NHCH_3$, NHC(O)—$N(CH_3)_2$, CN, or $CF_3$,
or a pharmaceutically acceptable salt thereof.

In one embodiment of the above compound, wherein $R_1$, $R_2$, $R_3$, $R_4$, and $R_5$ are each independently H, halogen, $CF_3$ or $C_1$-$C_4$ alkyl.

In one embodiment of the above compound, B has the structure:

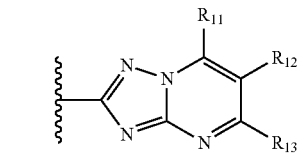

wherein $R_{11}$, $R_{12}$ and $R_{13}$ are each, independently, H, halogen, alkyl, alkenyl, alkynyl alkyl-OH, alkyl-$NH_2$, alkyl-OAc, alkyl-O(CO)-alkyl, alkyl-O-alkyl, haloalkyl, cycloalkyl, O-alkyl, NH-alkyl, C(O)OH, C(O)—$NH_2$, C(O)—$N(CH_3)_2$, C(O)—$NHCH_3$, NHC(O)—N$(CH_3)_2$, CN or $CF_3$.

In some embodiment, the compound having the structure:

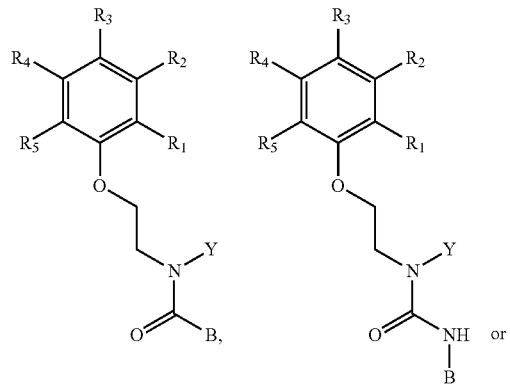

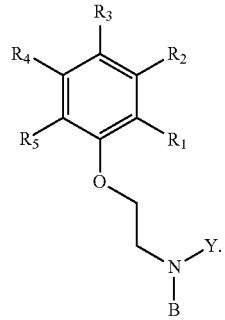

In some embodiments, wherein one of $R_1$, $R_2$, $R_3$, $R_4$, and $R_5$ is other than H.

In some embodiments, wherein two of $R_1$, $R_2$, $R_3$, $R_4$, and $R_5$ are other than H.

In some embodiments, B has the structure:

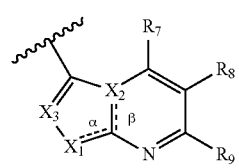

wherein

α and β are each a bond that is present or absent;

$X_1$ is N, NH or $NR_{10}$,
  wherein Rn is alkyl, alkenyl or alkynyl;

$X_2$ is C or N;

$X_3$ is CH or N;

$R_7$, $R_8$ and $R_9$ are each, independently, H, halogen, alkyl, alkenyl, alkynyl, alkyl-OH, alkyl-$NH_2$, alkyl-OAc alkyl-C(CO)-alkyl, alkyl-O-alkyl, haloalkyl, cycloalkyl, O-alkyl, NH-alkyl, C(O)OH, C(O)—$NH_2$, C(O)—N($CH_3$)$_2$, C(O)—$NHCH_3$, NHC(O)—N($CH_3$)$_2$, CN or $CF_3$, wherein $X_1$, $X_2$ and $X_3$ are each N, α is present and β is absent; or $X_1$ is NH, $X_2$ is C, $X_3$ is CH, α is absent and β is present; or $X_1$ is N, $X_2$ is N, $X_3$ is CH, α is present and β is absent; or $X_1$ is NH or $NR_{10}$, $X_2$ is C, $X_3$ is N, α is absent and β is present, wherein
  when $X_1$ is NH, $X_2$ is C, $X_3$ is N, α is absent and β is present, then one of $R_7$, $R_8$ and $R_9$ is other than H.

In some embodiments, B has the structure:

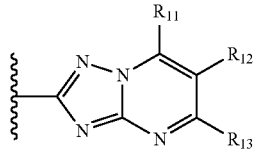

wherein $R_{11}$, $R_{12}$ and $R_{13}$ are each, independently, H, halogen, alkyl, alkenyl, alkynyl alkyl-OH, alkyl-$NH_2$, alkyl-OAc, alkyl-O(CO)-alkyl, alkyl-O-alkyl, haloalkyl, cycloalkyl, O-alkyl, NH-alkyl, C(O)OH, C(O)—$NH_2$, C(O)—N($CH_3$)$_2$, C(O)—$NHCH_3$, NHC(O)—N($CH_3$)$_2$, CN or $CF_3$.

In some embodiments, the compound wherein B has the structure:

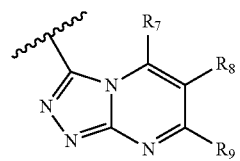

$R_7$, $R_8$ and $R_9$ are each, independently, H, halogen, alkyl, alkyl-OH, alkyl-$NH_2$, alkyl-OAc, alkyl-O-alkyl, haloalkyl, cycloalkyl, O-alkyl, NH-alkyl, C(O)OH, C(O)—$NH_2$, C(O)—N($CH_3$)$_2$, C(O)—$NHCH_3$, NHC(O)—N($CH_3$)$_2$, CN, or $CF_3$.

In some embodiments, the compound wherein B has the structure:

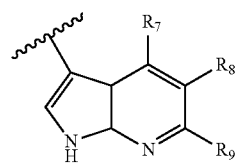

$R_7$, $R_8$ and $R_9$ are each, independently, H, halogen, alkyl, alkyl-OH, alkyl-$NH_2$, alkyl-OAc, alkyl-O-alkyl, haloalkyl, cycloalkyl, O-alkyl, NH-alkyl, C(O)OH, C(O)—$NH_2$, C(O)—N($CH_3$)$_2$, C(O)—$NHCH_3$, NHC(O)—N($CH_3$)$_2$, CN, or $CF_3$.

In some embodiments, the compound wherein B has the structure:

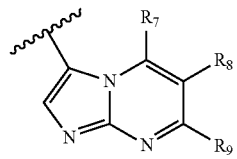

$R_7$, $R_8$ and $R_9$ are each, independently, H, halogen, alkyl, alkyl-OH, alkyl-$NH_2$, alkyl-OAc, alkyl-O-alkyl, haloalkyl, cycloalkyl, O-alkyl, NH-alkyl, C(O)OH, C(O)—$NH_2$, C(O)—N($CH_3$)$_2$, C(O)—$NHCH_3$, NHC(O)—N($CH_3$)$_2$, CN, or $CF_3$.

In some embodiments, the compound wherein B has the structure:

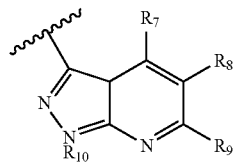

$R_7$, $R_8$ and $R_9$ are each, independently, H, halogen, alkyl, alkyl-OH, alkyl-$NH_2$, alkyl-OAc, alkyl-O-alkyl, haloalkyl, cycloalkyl, O-alkyl, NH-alkyl, C(O)OH, C(O)—$NH_2$, C(O)—N($CH_3$)$_2$, C(O)—$NHCH_3$, NHC(O)—N($CH_3$)$_2$, CN, or $CF_3$; and $R_{10}$ is alkyl, alkenyl or alkynyl.

In some embodiments, the compound wherein $R_7$, $R_8$ and $R_9$ are each, independently, H, Cl, Br, F, $OCH_3$, $OCH_2CH_3$, $CF_3$, CN, $CH_3$, $CH_3CH_3$, C(O)OH or C(O)—$NH_2$ In some embodiments, the compound wherein $R_7$, $R_8$ and $R_9$ are each, independently, H, $CH_2CH_2OH$, $CH_2CH_2OCH_3$, $CH_2CH_2OAc$, $CH_2CH_2Cl$, $CH_2CH_2F$ or $CH_2CH_2Br$.

In some embodiments, the compound wherein $R_7$, $R_8$ and $R_9$ are each, independently, H, halogen or alkyl.

In some embodiments, the compound wherein two of $R_7$, $R_8$ and $R_9$ are each H and the remaining one of $R_7$, $R_8$ and $R_9$ is other than H.

In some embodiments, the compound wherein one of $R_7$, $R_8$ and $R_9$ is H and the remaining two of $R_7$, $R_8$ and $R_9$ are each other than H.

In some embodiments, the compound wherein B has the structure:

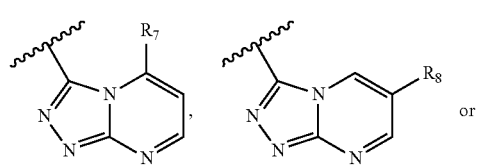

-continued

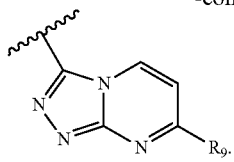

In some embodiments, the compound wherein $R_7$, $R_8$ and $R_9$ are each, independently, H, $CH_3$, Br, Cl, F, $CH_2CH_2OH$, $CH_2CH_2OCH_3$, $CH_2CH_2OAc$, $CH_2CH_2Cl$, $CH_2CH_2F$ or $CH_2CH_2Br$.

In some embodiments, the compound wherein B has the structure:

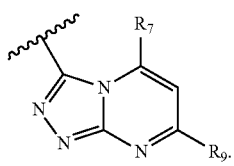

In some embodiments, the compound wherein $R_7$ and $R_9$ are each, independently, H, $CH_3$, Br, Cl, F, $CH_2CH_2OH$, $CH_2CH_2OCH_3$, $CH_2CH_2OAc$, $CH_2CH_2Cl$, $CH_2CH_2F$ or $CH_2CH_2Br$.

In some embodiments, the compound wherein B has the structure:

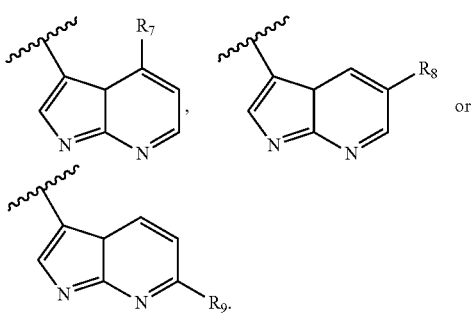

In some embodiments, the compound wherein $R_7$, $R_8$ and $R_9$ are each, independently, H, $CH_3$, Br, Cl, F, $CH_2CH_2OH$, $CH_2CH_2OCH_3$, $CH_2CH_2OAc$, $CH_2CH_2Cl$, $CH_2CH_2F$ or $CH_2CH_2Br$.

In some embodiments, the compound wherein B has the structure:

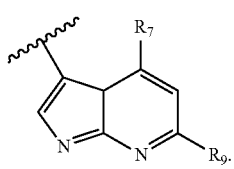

In some embodiments, the compound wherein $R_7$ and $R_9$ are each, independently, H, $CH_3$, Br, Cl, F, $CH_2CH_2OH$, $CH_2CH_2OCH_3$, $CH_2CH_2OAc$, $CH_2CH_2Cl$, $CH_2CH_2F$ or $CH_2CH_2Br$.

In some embodiments, the compound wherein B has the structure:

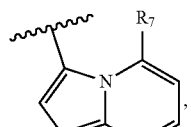 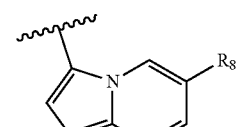

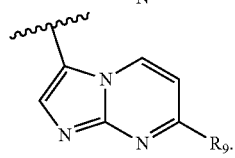

In some embodiments, the compound wherein $R_7$, $R_8$ and $R_9$ are each, independently, H, $CH_3$, Br, Cl, F, $CH_2CH_2OH$, $CH_2CH_2OCH_3$, $CH_2CH_2OAc$, $CH_2CH_2Cl$, $CH_2CH_2F$ or $CH_2CH_2Br$.

In some embodiments, the compound wherein B has the structure:

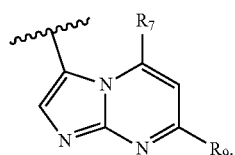

In some embodiments, the compound wherein $R_7$ and $R_9$ are each, independently, H, $CH_3$, Br, Cl, F, $CH_2CH_2OH$, $CH_2CH_2OCH_3$, $CH_2CH_2OAc$, $CH_2CH_2Cl$, $CH_2CH_2F$ or $CH_2CH_2Br$.

In some embodiments, the compound wherein B has the structure:

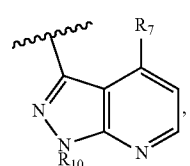 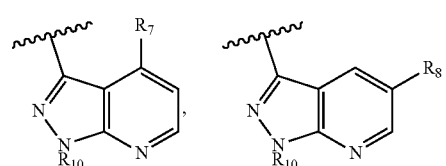

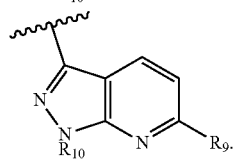

In some embodiments, the compound wherein $R_7$, $R_8$ and $R_9$ are each, independently, H, $CH_3$, Br, Cl, F, $CH_2CH_2OH$, $CH_2CH_2OCH_3$, $CH_2CH_2OAc$, $CH_2CH_2Cl$, $CH_2CH_2F$ or $CH_2CH_2Br$; and Rn is alkyl.

In some embodiments, the compound wherein B has the structure:

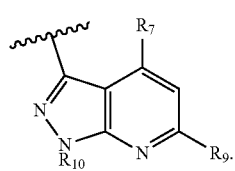

In some embodiments, the compound wherein $R_7$ and $R_9$ are each, independently, H, $CH_3$, Br, Cl, F, $CH_2CH_2OH$, $CH_2CH_2OCH_3$, $CH_2CH_2OAc$, $CH_2CH_2Cl$, $CH_2CH_2F$ or $CH_2CH_2Br$; and $R_{10}$ is alkyl.

In some embodiments, the compound wherein B has the structure:

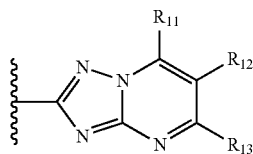

wherein
$R_{11}$, $R_{12}$ and $R_{13}$ are each, independently, H, halogen, alkyl, alkyl-OH, alkyl-$NH_2$, alkyl-OAc, alkyl-O-alkyl, haloalkyl, cycloalkyl, O-alkyl, NH-alkyl, C(O)OH, C(O)—$NH_2$, C(O)—N($CH_3$)$_2$, C(O)—NH$CH_3$, NHC(O)—N($CH_3$)$_2$, CN, or $CF_3$.

In some embodiments, the compound wherein B has the structure:

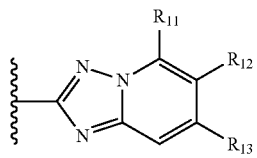

wherein
$R_{11}$, $R_{12}$ and $F_{13}$ are each, independently, H, halogen, alkyl, alkyl-OH, alkyl-$NH_2$, alkyl-OAc, alkyl-O-alkyl, haloalkyl, cycloalkyl, O-alkyl, NH-alkyl, C(O)OH, C(O)—$NH_2$, C(O)—N($CH_3$)$_2$, C(O)—NH$CH_3$, NHC(O)—N($CH_3$)$_2$, CN, or $CF_3$.

In some embodiments, the compound wherein B has the structure:

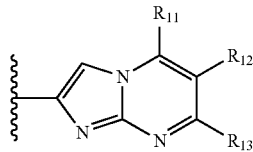

wherein
$R_{11}$, $R_{12}$ and $R_{13}$ are each, independently, H, halogen, alkyl, alkyl-OH, alkyl-$NH_2$, alkyl-OAc, alkyl-O-alkyl, haloalkyl, cycloalkyl, O-alkyl, NH-alkyl, C(O)OH, C(O)—$NH_2$, C(O)—N($CH_3$)$_2$, C(O)—NH$CH_3$, NHC(O)—N($CH_3$)$_2$, CN, or $CF_3$.

In some embodiments, the compound wherein B has the structure:

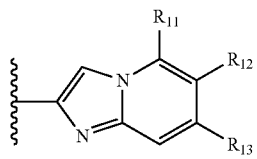

wherein
$R_{11}$, $R_{12}$ and $R_{13}$ are each, independently, H, halogen, alkyl, alkyl-OH, alkyl-$NH_2$, alkyl-OAc, alkyl-O-alkyl, haloalkyl, cycloalkyl, O-alkyl, NH-alkyl, C(O)OH, C(O)—$NH_2$, C(O)—N($CH_3$)$_2$, C(O)—NH$CH_3$, NHC(O)—N($CH_3$)$_2$, CN, or $CF_3$.

In some embodiments, the compound $R_{11}$, $R_{12}$ and $R_{13}$ are each, independently, H, Cl, Br, F, O$CH_3$, O$CH_2CH_3$, $CF_3$, CN, $CH_3$, $CH_3CH_3$, C(O)OH or C(O)—$NH_2$.

In some embodiments, the compound Ru, $R_{12}$ and $R_{13}$ are each, independently, H, $CH_2CH_2OH$, $CH_2CH_2OCH_3$, $CH_2CH_2OAc$, $CH_2CH_2Cl$, $CH_2CH_2F$ or $CH_2CH_2Br$.

In some embodiments, the compound $R_{11}$, $R_{12}$ and $R_{13}$ are each, independently, H, halogen or alkyl.

In some embodiments, the compound wherein two of $R_{11}$, $R_{12}$ and $R_{13}$ are each H and the remaining one of $R_{11}$, $R_{12}$ and $R_{13}$ is other than H.

In some embodiments, the compound wherein one of $R_{11}$, $R_{12}$ and $R_{13}$ is H and the remaining two of $R_{11}$, $R_{12}$ and $R_{13}$ are each other than H.

In some embodiments, the compound wherein B has the structure:

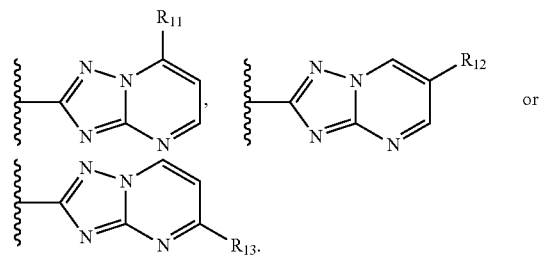

In some embodiments, the compound wherein $R_{11}$, $R_{12}$ and $R_{13}$ are each, independently, H, $CH_3$, Br, Cl, F, $CH_2CH_2OH$, $CH_2CH_2OCH_3$, $CH_2CH_2OAc$, $CH_2CH_2Cl$, $CH_2CH_2F$ or $CH_2CH_2Br$.

In some embodiments, the compound wherein B has the structure:

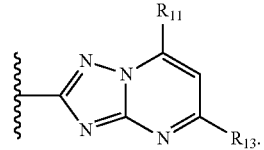

In some embodiments, the compound wherein $R_{11}$ and $R_{13}$ are each, independently, H, $CH_3$, Br, Cl, F, $CH_2CH_2OH$, $CH_2CH_2OCH_3$, $CH_2CH_2OAc$, $CH_2CH_2Cl$, $CH_2CH_2F$ or $CH_2CH_2Br$.

In some embodiments, the compound wherein X is N. In some embodiments, the compound wherein X is CH.

In some embodiments, the compound wherein $R_1$, $R_2$, $R_3$, $R_4$, and $R_5$ are each H, t-Bu, Cl, F, or $CF_3$.

In some embodiments, the compound wherein
$R_1$, $R_2$, $R_3$, and $R_4$ are each H; and
$R_5$ is $CF_3$ or t-Bu.

In some embodiments, the compound wherein
$R_1$, $R_3$ and $R_4$ are each H;
$R_2$ is halogen;
$R_5$ is $CF_3$ or t-Bu.

In some embodiments, the compound wherein
$R_1$, $R_2$, $R_3$, and $R_4$ are each H,
$R_5$ is $CF_3$ or t-Bu.

In some embodiments, the compound wherein
$R_1$, $R_2$, $R_3$, and $R_4$ are each H,
$R_5$ is $CF_3$.

In some embodiments, the compound wherein
$R_1$, $R_2$, $R_3$, $R_4$, and $R_5$ are each H, methyl, ethyl, phenyl, t-Bu, i-Pr, Cl, Br, F or $CF_3$;

In some embodiments, the compound wherein
wherein
$R_1$, $R_2$, $R_3$, and $R_4$ are each H;
$R_5$ is —H, methyl, ethyl, i-Pr or phenyl.

In some embodiments, the compound wherein
$R_1$, $R_2$, $R_3$, $R_4$, and $R_5$ are each H, methyl, ethyl, phenyl, t-Bu, i-Pr, $OCF_3$, $CF_3$, $OCF_2CF_3$, $CF_2CF_3$, Cl, Br, or F.

In some embodiments, the compound wherein
$R_1$, $R_2$, $R_3$, and $R_4$ are each H;
$R_5$ is —H, $OCF_3$, $CF_2CF_3$, methyl, ethyl, i-Pr or phenyl.

In some embodiments, the compound wherein one of $R_1$, $R_2$, $R_3$, $R_4$, and $R_5$ is other than H.

In some embodiments, the compound wherein two of $R_1$, $R_2$, $R_3$, $R_4$ and $R_5$ are other than H.

In some embodiments, the compound wherein two or more of $R_1$, $R_2$, $R_3$, $R_4$, and $R_5$ are other than H.

In some embodiments, the compound wherein three of $R_1$, $R_2$, $R_3$, $R_4$, and $R_5$ are other than H.

In some embodiments, the compound Wherein three or more of $R_1$, $R_2$, $R_3$, $R_4$, and $R_5$ are other than H.

In some embodiments, the compound wherein having the structure:

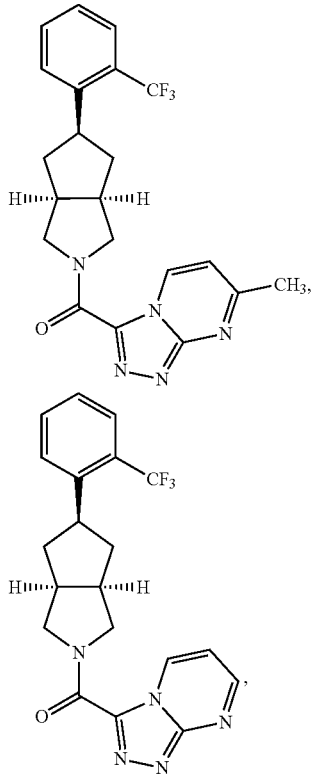

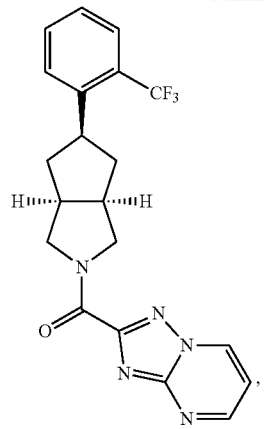

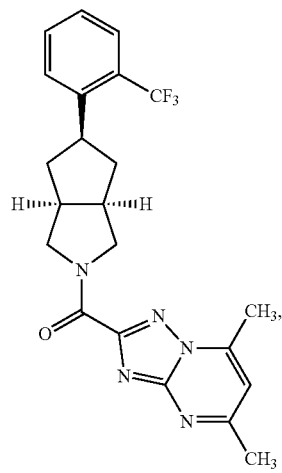

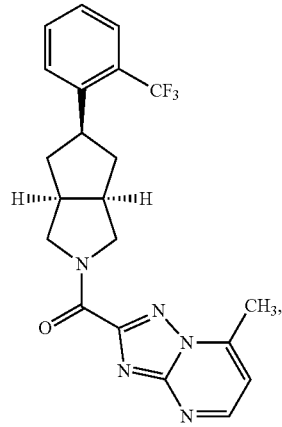

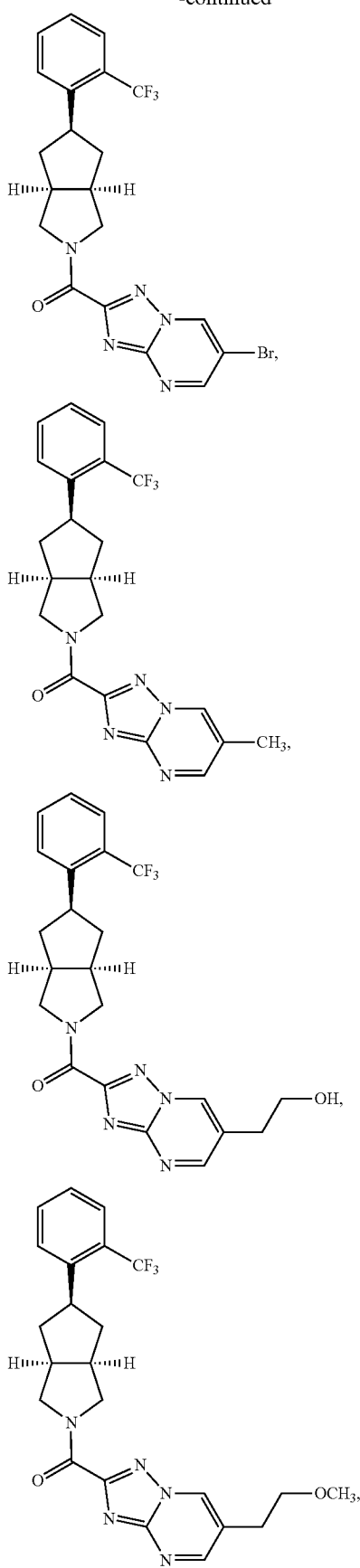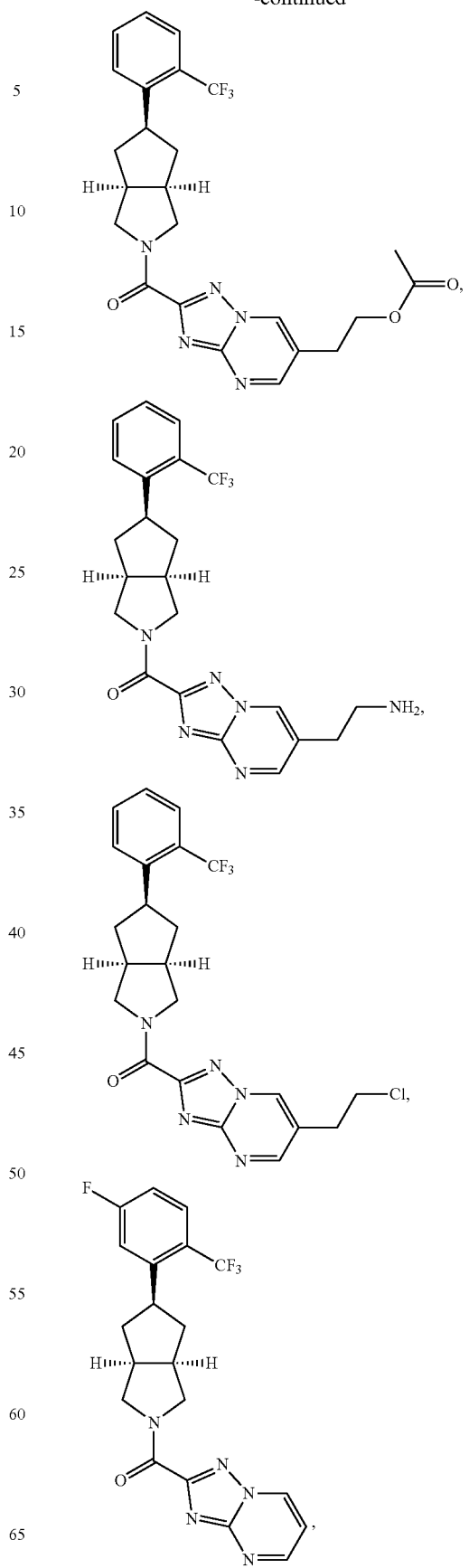

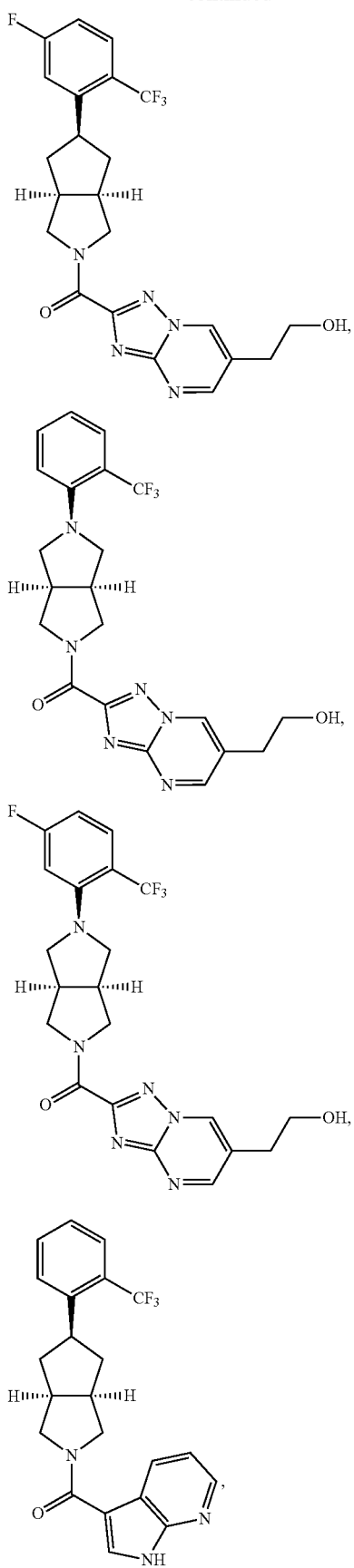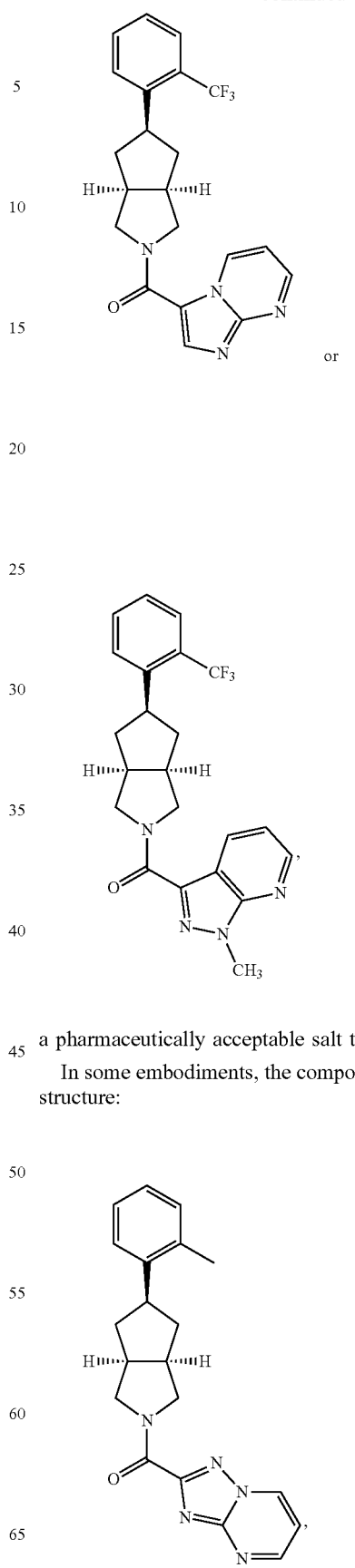
a pharmaceutically acceptable salt thereof.
In some embodiments, the compound wherein having the structure:
(10a)
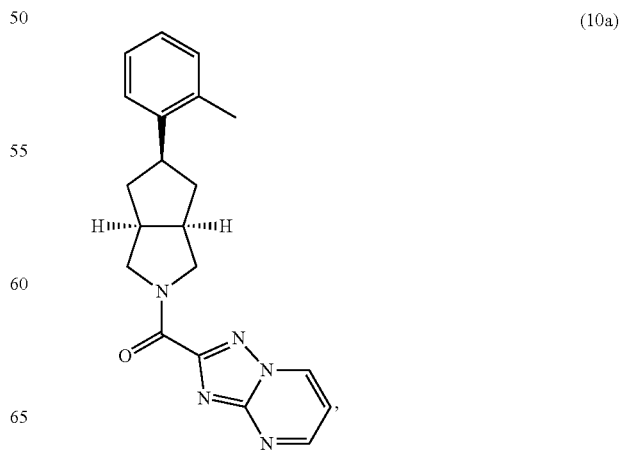

-continued
(10b)
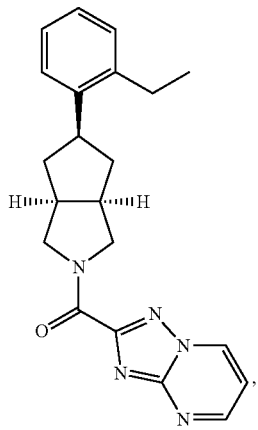
(10c)
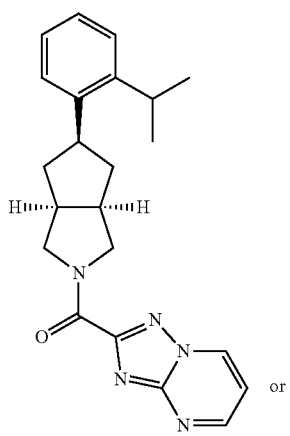
or
(10d)
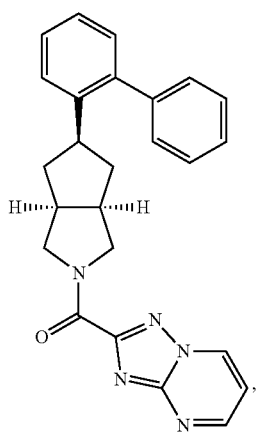
a pharmaceutically acceptable salt thereof.
In some embodiments, the compound wherein having the structure:
(9a)
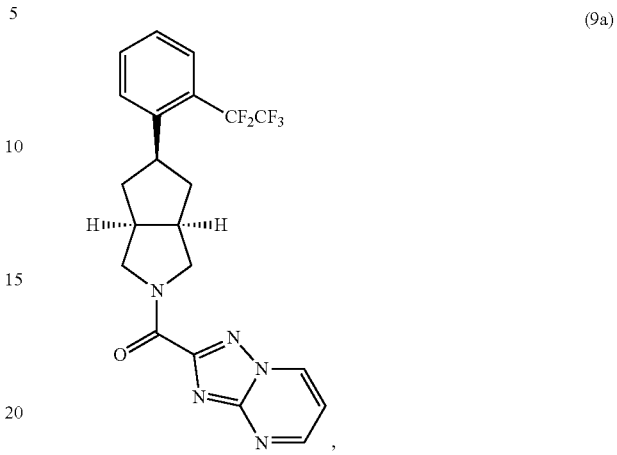
(9b)
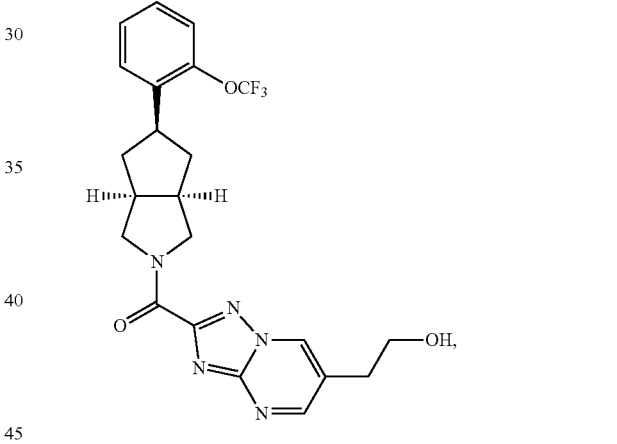
(9c)
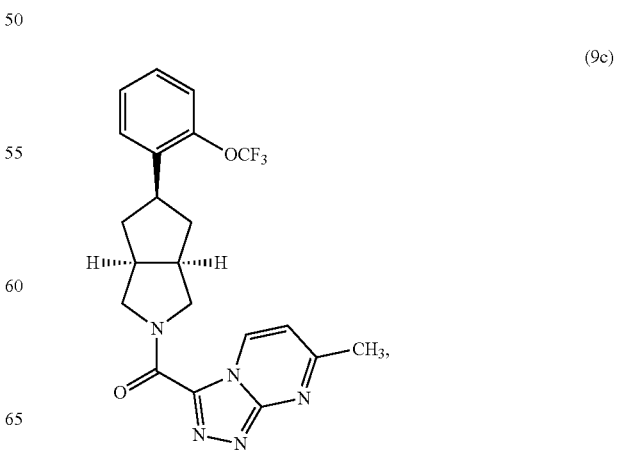

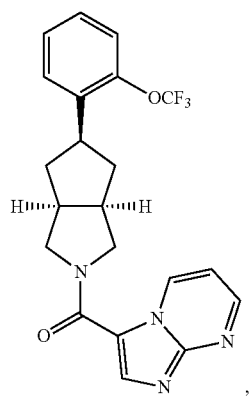 (9d)
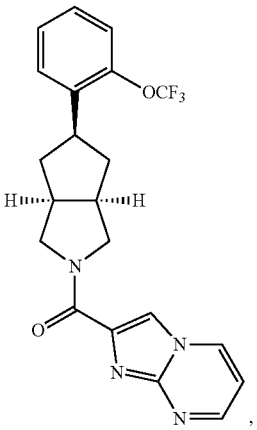 (9g)
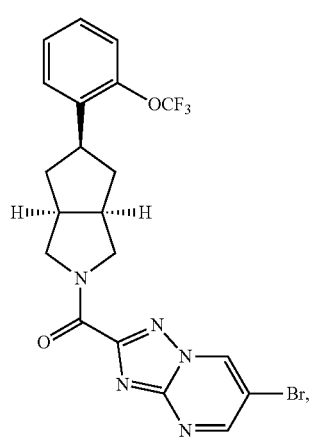 (9e)
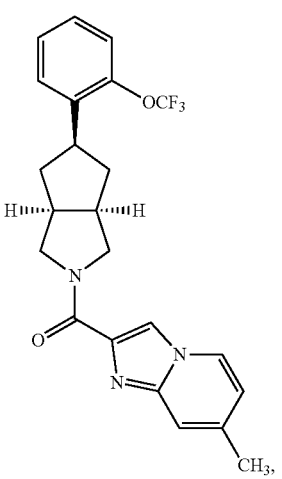 (9h)
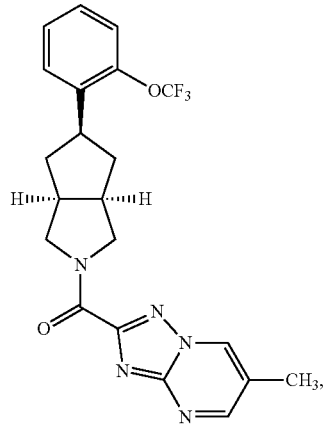 (9f)
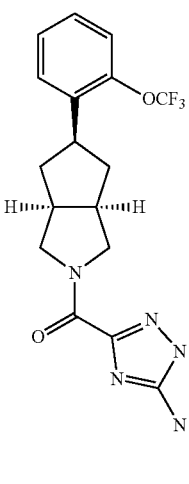 (9i)

-continued (9j)

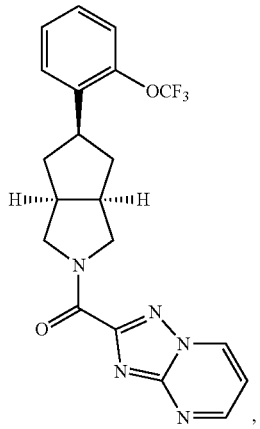

a pharmaceutically acceptable salt thereof.

In some embodiments, B is other than

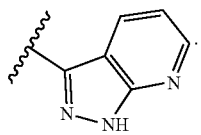 [SMILES: *c1n[nH]c2ncccc12]

In any embodiment of any of the above compounds, $R_1$, $R_2$, $R_3$, $R_4$, and $R_5$ are each independently H, halogen, $CF_3$, $C_1$-$C_{12}$ alkyl, aryl or heteroaryl.

In any embodiment of any of the above compounds, $R_1$, $R_2$, $R_3$, $R_4$, and $R_5$ are each independently H, halogen, $CF_3$, $C_1$-$C_6$ alkyl, aryl or heteroaryl.

In any embodiment of any of the above compounds, $R_1$, $R_2$, $R_3$, $R_4$, and $R_5$ are each independently H, halogen, $CF_3$, $C_1$-$C_4$ alkyl, aryl or heteroaryl.

In any embodiment of any of the above compounds where one of $R_1$, $R_2$, $R_3$, $R_4$, and $R_5$ is other than H, the compound is more active than the corresponding compound where $R_1$, $R_2$, $R_3$, $R_4$, and $R_5$ are each H. For example, the compound corresponding to compound 10a where $R_1$, $R_2$, $R_3$, $R_4$, and $R_5$ are each H is less active. Without being bound by any specific theory, it is believed that the position of the substitution at the $R_1$ or $R_5$ position on the phenyl ring of, e.g., compounds 10a-10d increases activity relative to the corresponding compounds where $R_1$, $R_2$, $R_3$, $R_4$, and $R_5$ are each H. The claimed compounds each containing a substitution at the $R_1$ or $R_5$ position have improved activity in RBP4 assays and reduced or no substantial activity in PPARγ assays.

The present invention provides a pharmaceutical composition comprising a compound of the present invention and a pharmaceutically acceptable carrier.

The present invention provides a method for treating a disease characterized by excessive lipofuscin accumulation in the retina in a mammal afflicted therewith comprising administering to the mammal an effective amount of a compound of the present invention or a composition of the present invention.

The present invention provides a method for lowering the serum concentration of RBP4 in a mammal comprising administering to the mammal an effective amount of a compound of the present invention or a composition of the present invention.

In some embodiments of the method, wherein the disease is further characterized by bisretinoid-mediated macular degeneration.

In some embodiments of the method, wherein the amount of the compound is effective to lower the serum concentration of RBP4 in the mammal.

In some embodiments of the method, wherein the amount of the compound is effective to lower the retinal concentration of a bisretinoid in lipofuscin in the mammal.

In some embodiments of the method, wherein the bisretinoid is A2E. In some embodiments of the method, wherein the bisretinoid is isoA2E. In some embodiments of the method, wherein the bisretinoid is A2-DHP-PE. In some embodiments of the method, wherein the bisretinoid is atRAL di-PE.

In some embodiments of the method, wherein the disease characterized by excessive lipofuscin accumulation in the retina is Age-Related Macular Degeneration.

In some embodiments of the method, wherein the disease characterized by excessive lipofuscin accumulation in the retina is cry (atrophic) Age-Related Macular Degeneration.

In some embodiments of the method, wherein the disease characterized by excessive lipofuscin accumulation in the retina is Stargardt Disease.

In some embodiments of the method, wherein the disease characterized by excessive lipofuscin accumulation in the retina is Best disease.

In some embodiments of the method, wherein the disease characterized by excessive lipofuscin accumulation in the retina is adult vitelli form maculopathy.

In some embodiments of the method, wherein the disease characterized by excessive lipofuscin accumulation in the retina is Stargardt-like macular dystrophy.

In some embodiments, bisretinoid-mediated macular degeneration is Age-Related Macular Degeneration or Stargardt Disease. In some embodiments, the bisretinoid-mediated macular degeneration is Age-Related Macular Degeneration. In some embodiments, the bisretinoid-mediated macular degeneration is dry (atrophic) Age-Related Macular Degeneration.

In some embodiments, the bisretinoid-mediated macular degeneration is Stargardt Disease. In some embodiments, the bisretinoid-mediated macular degeneration is Best disease. In some embodiments, the bisretinoid-mediated macular degeneration is adult vitelliform maculopathy. In some embodiments, the bisretinoid-mediated macular degeneration is Stargardt-like macular dystrophy. The bisretinoid-mediated macular degeneration may comprise the accumulation of lipofuscin deposits in the retinal pigment epithelium.

In some embodiments of the method, the amount of the compound is administered to the eye of the mammal.

In some embodiments of the method, the amount of the compound is administered topically to the eye of the mammal.

Figure 2:
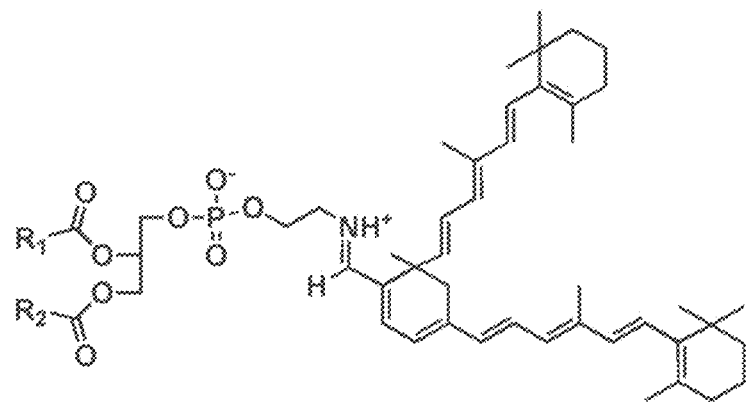
FIG. 2. Structure of bisretinoid atRAL di-PE (all-trans retinal dimer-phosphatidyl ethanolamine), a cytotoxic component of retinal lipofuscin. R1 and R2 refer to various fatty acid constituents.
Figure 2:
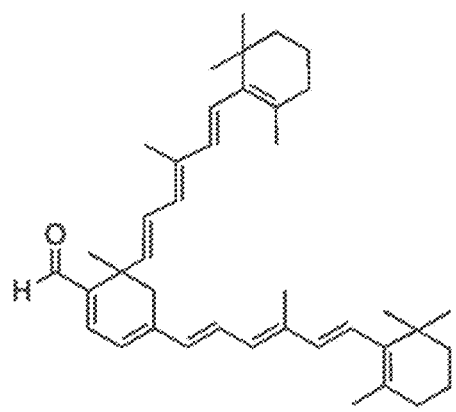
Figure 3:
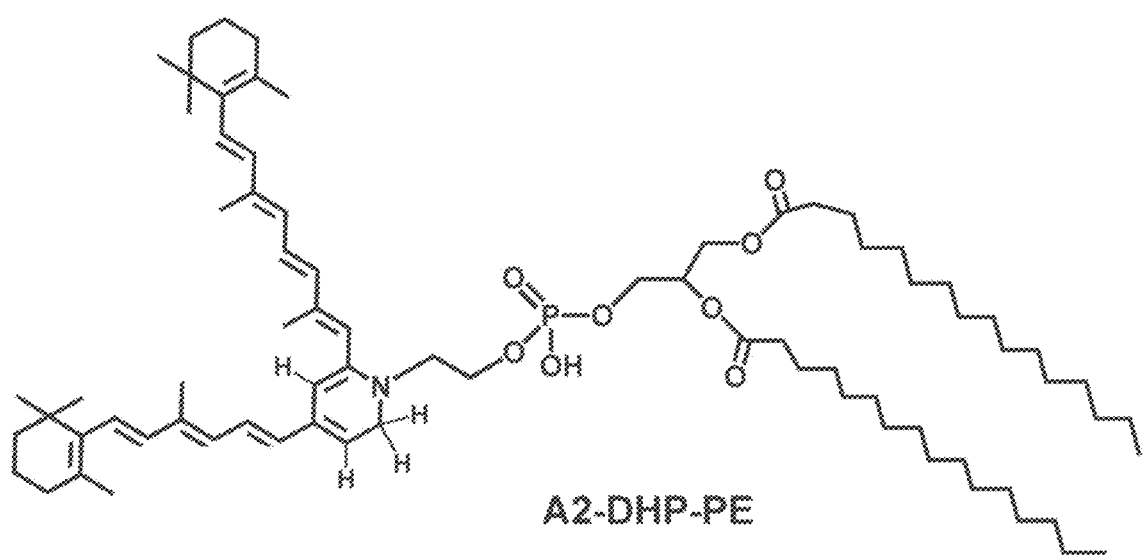
FIG. 3. Structure of bisretinoid A2-DHP-PE, a cytotoxic component of retinal lipofuscin.

As used herein, "bisretinoid lipofuscin" is lipofuscin containing a cytotoxic bisretinoid. Cytotoxic bisretinoids include but are not necessarily limited to A2E, isoA2E, atRAL di-PE, and A2-DHP-PE (FIGS. 1, 2, and 3).

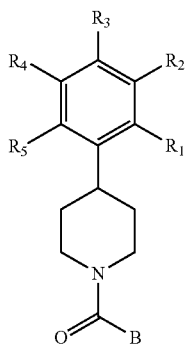

The compounds of the present application having the above structure may be synthesized using the methods disclosed in WO 2014/15201, published Sep. 25, 2014, or WO 2015/168286, published Nov. 5, 2015, the contents of each of which are hereby incorporated by reference.

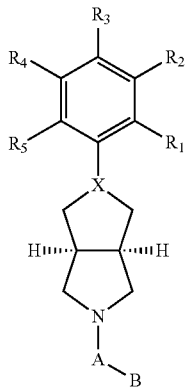

The compounds of the present application having the above structure may be synthesized according to the methods disclosed in WO 2014/152018, published Sep. 25, 2014, or WO 2014/151936, published Sep. 25, 2014, the contents of each of which are hereby incorporated by reference.

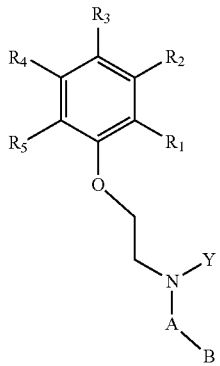

The compounds of the present application having the above structure may be synthesized according to the methods disclosed in WO 2014/151959, published Sep. 25, 2014, the contents of which are hereby incorporated by reference.

The B groups described herein may be attached to the following compounds by amide coupling or similar coupling methods known to one skilled in the art to prepare the compounds of the present application.

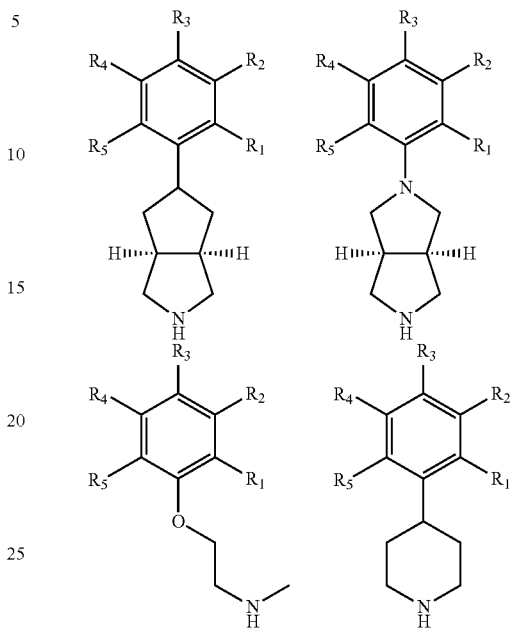

For example, a mixture of the above amine (1 equiv), desired carboxylic acid "B" group (1 equiv), triethylamine ($Et_3N$) (3 equiv), and 2-(1H-benzotriazole-1-yl)-1,1,3,3-tetramethyluronium hexafluorophosphate (HBTU) (1.5 equiv) in DMF (0.25 M) are stirred at room temperature until the reaction is complete by LC-MS. The mixture is diluted with $H_2O$ and extracted with EtOAc. The combined organic extracts are washed with $H_2O$, brine, dried over $Na_2SO_4$, filtered, and concentrated under reduced pressure. The resulting residue is purified by silica gel chromatography (typical eluents included either a mixture of or hexanes and EtOAc or a mixture of $CH_2Cl_2$ and a 90:9:1 mixture of $CH_2Cl_2/CH_3OH$/concentrated $NH_4OH$) Lo afford the desired carboxamide.

Except where otherwise specified, when the structure of a compound of this invention includes an asymmetric carbon atom, it is understood that the compound occurs as a racemate, racemic mixture, and isolated single enantiomer. All such isomeric forms of these compounds are expressly included in this invention. Except where otherwise specified, each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "Enantiomers, Racemates and Resolutions" by J. Jacques, A. Collet and S. Wilen, Pub. John Wiley & Sons, N Y, 1981. For example, the resolution may be carried out by preparative chromatography on a chiral column.

The subject invention is also intended to include all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include C-13 and C-14.

It will be noted that any notation of a carbon in structures throughout this application, when used without further notation, are intended to represent all isotopes of carbon, such as $^{12}C$, $^{13}C$, or $^{14}C$. Furthermore, any compounds containing $^{13}C$ or $^{14}C$ may specifically have the structure of any of the compounds disclosed herein.

It will also be noted that any notation of a hydrogen in structures throughout this application, when used without further notation, are intended to represent all isotopes of hydrogen, such as $^{1}H$, $^{2}H$, or $^{3}H$. Furthermore, any compounds containing $^{13}C$ or $^{14}C$ may specifically have the structure of any of the compounds disclosed herein.

Isotopically-labeled compounds can generally be prepared by conventional techniques known to those skilled in the art using appropriate isotopically-labeled reagents in place of the non-labeled reagents employed.

The term "substitution", "substituted" and "substituent" refers to a functional group as described above in which one or more bonds to a hydrogen atom contained therein are replaced by a bond to non-hydrogen or non-carbon atoms, provided that normal valencies are maintained and that the substitution results in a stable compound. Substituted groups also include groups in which one or more bonds to a carbon(s) or hydrogen(s) atom are replaced by one or more bonds, including double or triple bonds, to a heteroatom. Examples of substituent groups include the functional groups described above, and halogens (i.e., F, Cl, Br, and I); alkyl groups, such as methyl, ethyl, n-propyl, isopropryl, n-butyl, tert-butyl, and trifluoromethyl; hydroxyl; alkoxy groups, such as methoxy, ethoxy, n-propoxy, and isopropoxy; aryloxy groups, such as phenoxy; arylalkyloxy, such as benzyloxy (phenylmethoxy) and p-trifluoromethylbenzyloxy (4-trifluoromethylphenylmethoxy); heteroaryloxy groups; sulfonyl groups, such as trifluoromethanesulfonyl, methanesulfonyl, and p-toluenesulfonyl; nitro, nitrosyl; mercapto; sulfanyl groups, such as methylsulfanyl, ethylsulfanyl and propylsulfanyl; cyano; amino groups, such as amino, methylamino, dimethylamino, ethylamino, and diethylamino; and carboxyl. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

In the compounds used in the method of the present invention, the substituents may be substituted or unsubstituted, unless specifically defined otherwise.

In the compounds used in the method of the present invention, alkyl, heteroalkyl, monocyclic, bicyclic, aryl, heteroaryl and heterocyclic groups can be further substituted by replacing one or more hydrogen atoms with alternative non-hydrogen groups. These include, but are not limited to, halo, hydroxy, mercapto, amino, carboxy, cyano and carbamoyl.

It is understood that substituents and substitution patterns on the compounds used in the method of the present invention can be selected by one of ordinary skill in the art to provide compounds that are chemically stable and that can be readily synthesized by techniques known in the art from readily available starting materials. If a substituent is itself substituted with more than one group, it is understood that these multiple groups may be on the same carbon or on different carbons, so long as a stable structure results.

In choosing the compounds used in the method of the present invention, one of ordinary skill in the art will recognize that the various substituents, i.e., $R_1$, $R_2$, etc. are to be chosen in conformity with well-known principles of chemical structure connectivity.

As used herein, "alkyl" includes both branched and straight-chain saturated aliphatic hydrocarbon groups having a specified number of carbon atoms and may be unsubstituted or substituted. Thus, $C_1$-$C_n$ as in "$C_1$-$C_n$ alkyl" is defined to include groups having 1, 2, . . . , n–1 or n carbons in a linear or branched arrangement. For example, $C_1$-$C_6$, as in "$C_1$-$C_6$ alkyl" is defined to include groups having 1, 2, 3, 4, 5, or 6 carbons in a linear or branched arrangement, and specifically includes methyl, ethyl, n-propyl, isopropyl, n-butyl, t-butyl, pentyl, and hexyl. Unless otherwise specified contains one to ten carbons. Alkyl groups can be unsubstituted or substituted with one or more substituents, including but not limited to halogen, alkoxy, alkylthio, trifluoromethyl, difluoromethyl, methoxy, and hydroxyl.

As used herein, "$C_1$-$C_4$ alkyl" includes both branched and straight-chain $C_1$-$C_4$ alkyl.

As used herein, "alkenyl" refers to a non-aromatic hydrocarbon radical, straight or branched, containing at least 1 carbon to carbon double bond, and up to the maximum possible number of non-aromatic carbon-carbon double bonds may be present, and may be unsubstituted or substituted. For example, "$C_2$-$C_6$ alkenyl" means an alkenyl radical having 2, 3, 4, 5, or 6 carbon atoms, and up to 1, 2, 3, 4, or 5 carbon-carbon double bonds respectively. Alkenyl groups include ethenyl, propenyl, butenyl and cyclohexenyl.

As used herein, "heteroalkyl" includes both branched and straight-chain saturated aliphatic hydrocarbon groups having at least 1 heteroatom within the chain or branch.

As used herein, "cycloalkyl" includes cyclic rings of alkanes of three to eight total carbon atoms, or any number within this range (i.e., cyclopropyl, cyclobutyl, cyclopentyl, cyclohexyl, cycloheptyl or cyclooctyl).

As used herein, "heterocycloalkyl" is intended to mean a 5- to 10-membered nonaromatic ring containing from 1 to 4 heteroatoms selected from the group consisting of O, N and S, and includes bicyclic groups. "Heterocyclyl" therefore includes, but is not limited to the following: imidazolyl, piperazinyl, piperidinyl, pyrrolidinyl, morpholinyl, thiomorpholinyl, tetrahydropyranyl, dihydropiperidinyl, tetrahydrothiophenyl and the like. If the heterocycle contains nitrogen, it is understood that the corresponding N-oxides thereof are also encompassed by this definition.

As used herein, "aryl" is intended to mean any stable monocyclic, bicyclic or polycyclic carbon ring of up to 10 atoms in each ring, wherein at least one ring is aromatic, and may be unsubstituted or substituted. Examples of such aryl elements include but are not limited to: phenyl, p-toluenyl (4-methylphenyl), naphthyl, tetrahydro-naphthyl, indanyl, phenanthryl, anthryl or acenaphthyl. In cases where the aryl substituent is bicyclic and one ring is non-aromatic, it is understood that attachment is via the aromatic ring.

The term "alkylaryl" refers to alkyl groups as described above wherein one or more bonds to hydrogen contained therein are replaced by a bond to an aryl group as described above. It is understood that an "alkylaryl" group is connected to a core molecule through a bond from the alkyl group and that the aryl group acts as a substituent on the alkyl group. Examples of arylalkyl moieties include, but are not limited to, benzyl (phenylmethyl), p-trifluoromethylbenzyl (1-trifluoromethylphenylmethyl), 1-phenylethyl, 2-phenylethyl, 3-phenylpropyl, 2-phenylpropyl and the like.

The term "heteroaryl" as used herein, represents a stable monocyclic, bicyclic or polycyclic ring of up to 10 atoms in each ring, wherein at least one ring is aromatic and contains from 1 to 4 heteroatoms selected from the group consisting of O, N and S. Bicyclic aromatic heteroaryl groups include but are not limited to phenyl, pyridine, pyrimidine or pyridizine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrrazolyl, indolyl, benzotriazolyl, benzothiazolyl, benzoxazolyl, isoxazolyl, isothiazolyl, furanyl, thienyl, benzothienyl, benzofuranyl, quinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition. As used herein, "monocycle" includes any stable polycyclic carbon ring of up to 10 atoms and may be unsubstituted or substituted. Examples of such non-aromatic monocycle elements include but are not limited to: cyclobutyl, cyclopentyl, cyclohexyl, and cycloheptyl. Examples of such aromatic monocycle elements include but are not limited to: phenyl. As used herein, "heteromonocycle" includes any monocycle containing at least one heteroatom.

As used herein, "bicycle" includes any stable polycyclic carbon ring of up to 10 atoms that is fused to a polycyclic carbon ring of up to 10 atoms with each ring being independently unsubstituted or substituted. Examples of such non-aromatic bicycle elements include but are not limited to: decahydronaphthalene. Examples of such aromatic bicycle elements include but are not limited to: naphthalene. As used herein, "heterobicycle" includes any bicycle containing at least one heteroatom.

The compounds used in the method of the present invention may be prepared by techniques well known in organic synthesis and familiar to a practitioner ordinarily skilled in the art. However, these may not be the only means by which to synthesize or obtain the desired compounds.

The compounds of present invention may be prepared by techniques described in Vogel's Textbook of Practical Organic Chemistry, A. I. Vogel, A. R. Tatchell, B. S. Furnis, A. J. Hannaford, P. W. G. Smith, (Prentice Hall) 5th Edition (1996), March's Advanced Organic Chemistry: Reactions, Mechanisms, and Structure, Michael B. Smith, Jerry March, (Wiley-Interscience) 5" Edition (2007), and references therein, which are incorporated by reference herein. However, these may not be the only means by which to synthesize or obtain the desired compounds.

The compounds of the present invention may be prepared by techniques described herein. The synthetic methods used to prepare the compounds of Examples 1 may be used to prepare additional compounds.

The various R groups attached to the aromatic rings of the compounds disclosed herein may be added to the rings by standard procedures, for example, those set forth in Advanced Organic Chemistry: Part B: Reaction and Synthesis, Francis Carey and Richard Sundberg, (Springer) 5th ed. Edition. (2007), the content of which is hereby incorporated by reference.

Another aspect of the invention comprises a compound of the present invention as a pharmaceutical composition.

As used herein, the term "pharmaceutically active agent" means any substance or compound suitable for administration to a subject and furnishes biological activity or other direct effect in the treatment, cure, mitigation, diagnosis, or prevention of disease, or affects the structure or any function of the subject. Pharmaceutically active agents include, but are not limited to, substances and compounds described in the Physicians' Desk Reference (PDR Network, LLC; 64th edition; Nov. 15, 2009) and "Approved Drug Products with Therapeutic Equivalence Evaluations" (U.S. Department Of Health And Human Services, $30^{th}$ edition, 2010), which are hereby incorporated by reference. Pharmaceutically active agents which have pendant carboxylic acid groups may be modified in accordance with the present invention using standard esterification reactions and methods readily available and known to those having ordinary skill in the art of chemical synthesis. Where a pharmaceutically active agent does not possess a carboxylic acid group, the ordinarily skilled artisan will be able to design and incorporate a carboxylic acid group into the pharmaceutically active agent where esterification may subsequently be carried out so long as the modification does not interfere with the pharmaceutically active agent's biological activity or effect.

The compounds of the present invention may be in a salt form. As used herein, a "salt" is a salt of the instant compounds which has been modified by making acid or base salts of the compounds. In the case of compounds used to treat a disease, the salt is pharmaceutically acceptable. Examples of pharmaceutically acceptable salts include, but are not limited to, mineral or organic acid salts of basic residues such as amines; alkali or organic salts of acidic res' dues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately treating a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1-19).

A salt or pharmaceutically acceptable salt is contemplated for all compounds disclosed herein.

As used herein, "treating" means preventing, slowing, halting, or reversing the progression of a disease or infection. Treating may also mean improving one or more symptoms of a disease or infection.

The compounds of the present invention may be administered in various forms, including those detailed herein. The treatment with the compound may be a component of a combination therapy or an adjunct therapy, i.e., the subject or patient in need of the drug is treated or given another drug for the disease in conjunction with one or more of the instant compounds. This combination therapy can be a sequential therapy where the patient is treated first with one drug and then the other or the two drugs are given simultaneously. These can be administered independently by the same route or by two or more different routes of administration depending on the dosage forms employed.

As used herein, a "pharmaceutically acceptable carrier" is a pharmaceutically acceptable solvent, suspending agent or vehicle, for delivering the instant compounds to the animal or human. The carrier may be liquid or solid and is selected with the planned manner of administration in mind. Liposomes are also a pharmaceutically acceptable carrier.

The dosage of the compounds administered in treatment will vary depending upon factors such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds used in the method of the present invention may comprise a single compound or mixtures thereof with additional agents. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection, topical application, or other methods, into or onto a site of infection, all using dosage forms well known to those of ordinary skill in the pharmaceutical arts.

The compounds used in the method of the present invention can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral, rectal, topical, intravenous or direct injection or parenteral administration. The compounds can be administered alone or mixed with a pharmaceutically acceptable carrier. This carrier can be a solid or liquid, and the type of carrier is generally chosen based on the type of administration being used. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol. 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol (Gilbert S. Banker, Christopher T. Rhodes, Eds.). All of the aforementioned publications are incorporated by reference herein.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds used in the method of the present invention may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines. The compounds may be administered as components of tissue-targeted emulsions.

The compounds used in the method of the present invention may also be coupled to soluble polymers as targetable drug carriers or as a prodrug. Such polymers include polyvinylpyrrolidone, pyran copolymer, polyhydroxylpropylmethacrylamide-phenol, polyhydroxyethylaspartamidephenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon, caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient compounds and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

For oral administration in liquid dosage form, the oral drug components are combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water-soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

The compounds used in the method of the present invention may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

Parenteral and intravenous forms may also include minerals and other materials to make them compatible with the type of injection or delivery system chosen.

Each embodiment disclosed herein is contemplated as being applicable to each of the other disclosed embodiments. Thus, all combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Materials and Methods
TR-FRET Assay for Retinol-Induced RBP4-TTR Interaction

Figure 7:
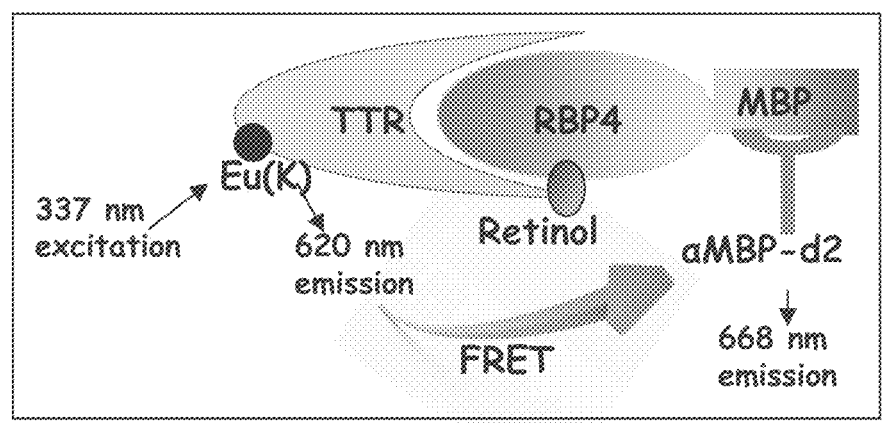
FIG. 7. Schematic depiction of the HTRF-based assay format for characterization of RBP4 antagonists disrupting retinol-induced RBP4-TTR interaction.

Binding of a desired RBP4 antagonist displaces retinol and induces hindrance for RBP4-TTR interaction resulting in the decreased FRET signal (FIG. 7). Bacterially expressed MBP-RBP4 and untagged TTR were used in this assay. For the use in the TR-FRET assay, the maltose binding protein (MBP)-tagged human RBP4 fragment (amino acids 19-201) was expressed in the Gold(DE3)pLysS $E.$ $coli$ strain (Stratagene) using the pMAL-c4x vector. Following cell lysis, recombinant RBP4 was purified from the soluble fraction using the ACTA FPLC system (GE Healthcare) equipped with the 5-ml the MBP Trap HP column. Human untagged TTR was purchased from Calbiochem. Untagged TTR was labeled directly with $Eu^{3+}$ Cryptate-NHS using the HTRF Cryptate Labeling kit from CisBio following the manufacturer's recommendations. HTRF assay was performed in white low volume 384 well plates (Greiner-Bio) in a final assay volume of 16 µl per well. The reaction buffer contained 10 mM Tris-HCl pH 7.5, 1 mM DTT, 0.05% NP-40, 0.05% Prionex, 6% glycerol, and 400 mM KF. Each reaction contained 60 nM MBP-RBP4 and 2 nM TTR-Eu along with 26.7 nM of anti-MBP antibody conjugated with d2 (Cisbio). Titration of test compounds in this assay was conducted in the presence of 1 µM retinol. All reactions were assembled in the dark under dim red light and incubated overnight at +4° C. wrapped in aluminum foil. TR-FRET signal was measured in the SpectraMax M5e Multimode Plate Reader (Molecular Device). Fluorescence was excited at 337 nm and two readings per well were taken: Reading 1 for time-gated energy transfer from Eu(K) to d2 (337 nm excitation, 668 nm emission, counting delay 75 microseconds, counting window 100 microseconds) and Reading 2 for Eu(K) time-gated fluorescence (337 nm excitation, 620 nm emission, counting delay 400 microseconds, counting window 400 microseconds). The TR-FRET signal was expressed as the ratio of fluorescence intensity: $Flu_{665}/Flu_{620} \times 10{,}000$.

Scintillation Proximity RBP4 Binding Assay

Untagged human RBP4 purified from the urine of tubular proteinuria patients was purchased from Fitzgerald Industries International. It was biotinylated using the EZ-Link Sulfo-NHS-LC-Biotinylation kit from Pierce following the manufacturer's recommendations. Binding experiments were performed in 96-well plates (OptiPlate, PerkinElmer) in a final assay volume of 100 µl per well in SPA buffer (1×PBS, pH 7.4, 1 mM EDTA, 0.1% BSA, 0.5% CHAPS). The reaction mix contained 10 nM $^3$H-Retinol (48.7 Ci/mmol; PerkinElmer), 0.3 mg/well Streptavidin-PVT beads, 50 nM biotinylated RBP4 and a test compound. Nonspecific binding was determined in the presence of 20 µM of unlabeled retinol. The reaction mix was assembled in the dark under dim red light. The plates were sealed with clear tape (TopSeal-A: 96-well microplate, PerkinElmer), wrapped in the aluminum foil, and allowed to equilibrate 6 hours at room temperature followed by overnight incubation at +4° C. Radiocounts were measured using a TopCount NXT counter (Packard Instrument Company).

PPARγ Agonist Assay

Figure 8:
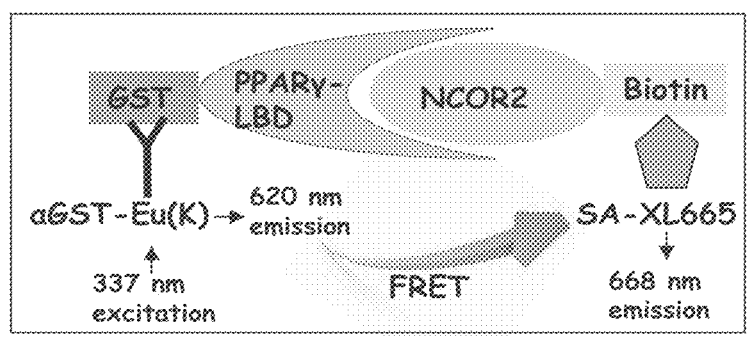
FIG. 8. Schematic depiction of the in vitro TR-FRET-based PPARγ-NCOR interaction assay to be used as a counter-screen. GST-tagged PPARγ fragment interacts with biotinylated NCOR peptide in the absence of ligand generating FRET. Test compounds specific for RBP4 should not affect the signal. Compounds with PPARγ agonistic activity induce conformation changes in the ligand binding domain of PPARγ leading to disruption of the PPARγ-NCOR interaction which is registered as a decrease in the FRET signal.

Significant safety issues are associated with the clinical use of PPARγ agonists (increased risk of death, myocardial infarction, stroke, congestive heart failure, hepatotoxicity, peripheral edema, weight gain and carcinogenicity[1-4]). We wanted to characterize the compounds we identified in a pilot screen as potential PPARγ agonists. The PPARγ assay is based on agonist-sensitive interaction of the GST-tagged ligand-binding domain (LRD) of the nuclear receptor PPARγ with the biotinylated corepressor NCOR peptide (FIG. 8).

The following reagents were used for the PPARγ agonist assay implementation:

1. GST-PPARγ_LBD:

Bacterially expressed protein fragment. For bacterial expression, ligand-binding domain of PPARγ (amino acids 176-477, GenBank accession number NP 005028) was subcloned into the SalI-NotI sites of pGEX-6p-3 vector. After the introduction of expression plasmid to the BL21-Gold (DE3)pLysS *E. coli* strain (Stratagene) recombinant protein (GST-tagged PPARγ-LBD) was purified from 1 L cultures using AKTA FPLC system (GE Healthcare) equipped with 5-ml GST Trap HP.

2. Biotinylated NCOR2 Peptide:

Biotin-Ahx(aminohexanoic acid)-ADPASNLGLE-DIIRKALMGSF-NH2

1 mM stock in DMSO

3. Eu(K)-Anti-GST Ab:

$Eu^{3+}$ Cryptate conjugated mouse monoclonal antibody anti-glutathione S-transferase from Cisbio (Cat no. 61GSTKLA)—320 nM, reconstituted in water 4. Streptavidin-XL665:

XL665-conjugated streptavidin from Cisbio (Cat no. 610SAXLA)—20 uM, reconstituted in water 5. Rosiglitazone (Positive Control).

Cayman Chemicals Cat #71740. 20 mM stock in DMSO. DMSO: Hybri-Max grade, Sigma cat 4 D2650

Buffers:

6. 5×HTRF Buffer:

50 mM Tris-HCl pH 7.5; 5 mM DTT; 0.25% NP-40; 0.25% BSA; 30% glycerol.

7. 4M KF Solution.

Made from potassium fluoride powder, Fluka cat #60238

Assay reactions are performed in a final volume of 16 ul. Final concentrations of components are: GST-PPARγ, 7 nM; NCOR2 peptide, 300 nM; Rosiglitazone (positive control), 20 μM.

Working solution was made containing 1×HTRF buffer and 100 mM KF (1×, 100).

The following three reagent solutions were prepared:

PPARγ: 18.7 nM PPARg in 1×, 100

NCOR2: 1200 nM NCOR2 in 1×, 100

Rosiglitazone (positive control): 80 uM in 1×, 100

In well of the 384-well assay plate, mix 6 ul of PPARγ solution, 4 ul of NCOR2 solution and 4 μl of Rosi solution. Test compounds diluted from DMSO stocks to 4× assay concentration in 1×HTRF, 100 mM KF buffer may be dispensed to well instead of Rosi. Negative control wells contained DMSO solvent alone; positive control well contained 10 uM biotin. Detection mix containing 6 nM of Eu(K)-anti-GST Ab and 336 nM of Streptavidin-XL665 was prepared in 1×HTRF, 100 mM KF assay buffer. Two μl of detection mix was added per well. Final concentrations of assay components in a 16-ul reaction mix are: 7 nM GST-PPARγ_LBD, 300 nM NCOR2, 0.75 nM Eu(K)-anti-GST Ab, 42 nM Streptavidin-XL665, 20 uM Rosiglitazone or test compounds. The plate was incubated for 16 hrs at 4° C.

HTRF signal was measured in the SpectraMax M5e Multimode Plate Reader (Molecular Device). Fluorescence was excited at 337 nm. Two readings per well were taken: Reading 1 for time-gated energy transfer from Eu(K) to XL665 (337 nm excitation, 668 nm emission, counting delay 50 microseconds, counting window 400 microseconds) and Reading 2 for Eu(K) time-gated fluorescence (337 nm excitation, 620 nm emission, counting delay 50 microseconds, counting window 400 microseconds). The signal was expressed as the ratio of fluorescence intensity: $Flu_{668}/Flu_{620} \times 10,000$.

Pharmacodynamic Studies of 7a and 7p in Balb/c Mice Following a Single Oral Administration Animal protocols were approved by the Institutional Animal Care and Use Committee of Columbia University and complied with guidelines set forth by The Association for Research in Vision and Ophthalmology. Compounds were prepared as a suspension in 0.9% NaCl, 2% Tween 80 for oral administration. Compounds were administered to Balb/c mice in a volume of 100 μL through oral gavage. The doses used were 15 mg/kg, 25 mg/kg and 35 mg/kg for 7a while two doses, 25 mg/kg and 35 mg/kg, were tested for DENG-31(FFB-0000082). Blood samples were collected at pre-dose and 1 hr, 2 hr, 4 hr, 6 hr, 8 hr, and 24 hr timepoints. Whole blood was drawn into a centrifuge tube and was let clot at room temperature for 30 min followed by centrifugation at 2,000×g for 15 minutes at +4° C. to collect serum. Serum RBP4 was measured using the RBP4 (mouse/rat) dual ELISA kit (AdipoGen) following the manufacturer's instructions.

Effect of 7a on accumulation of N-retinylidene-N-retinylethanolamine (A2E) in Eyes of the $Abca4^{-/-}$ Mice Animal protocols were approved by the Institutional Animal Care and Use Committee of Columbia University and complied with guidelines set forth by The Association for Research in Vision and Ophthalmology. Ten week-old Abca4 null mutant mice (129/SV×C57BL/6J) bred as previously described[26, 27] were used in the study. $Abca4^{-/-}$ (knockout) and C57BL/6J (wild-type control) mice were raised under 12 h on-off cyclic lighting with an in-cage illuminance of 30-50 lux. For long-term oral dosing 7a was formulated into Purina 5035 rodent chow at Research Diets, Inc. (New Brunswick, NJ) to ensure consistent 35 mg/kg daily oral dosing. Animals were administered the AKR-XI-85-containing chow for 8 weeks. Blood samples were collected at baseline and at the end of the dosing period for serum RBP4 measurements. Whole blood was drawn into a centrifuge tube and was let clot at room temperature for 30 min followed by centrifugation at 2,000×g for 15 minutes at +4° C. to collect serum. Serum RBP4 was measured using the RBP4 (mouse/rat) dual ELISA kit (AdipoGen) following the manufacturer's instructions.

After the completion of dosing, animals were euthanized and posterior eyecups consisting of sclera, choroid and RPE were prepared from enucleated eyes according to the standard techniques. Eyecups were combined in pools and shipped on dry ice to EyeCRO LLC, Oklahoma City, OK for the A2E analysis. A previously established HPLC method (Journal of Biological Chemistry, 275, 29354-29360) was utilized for quantifying A2E in mouse eyecups. Quantitation of A2E was conducted by manually integrating the A2E peak (approximately 12-min elution time) which was identified by the co-elution with the synthetic A2E standard and by characteristic absorbance spectrum. Calibration was conducted using the known amounts of synthetic A2E. All samples were processed at EyeCRO in a masked manner.

Example 1. Synthesis of Compounds

Scheme 1. General synthetic pathway

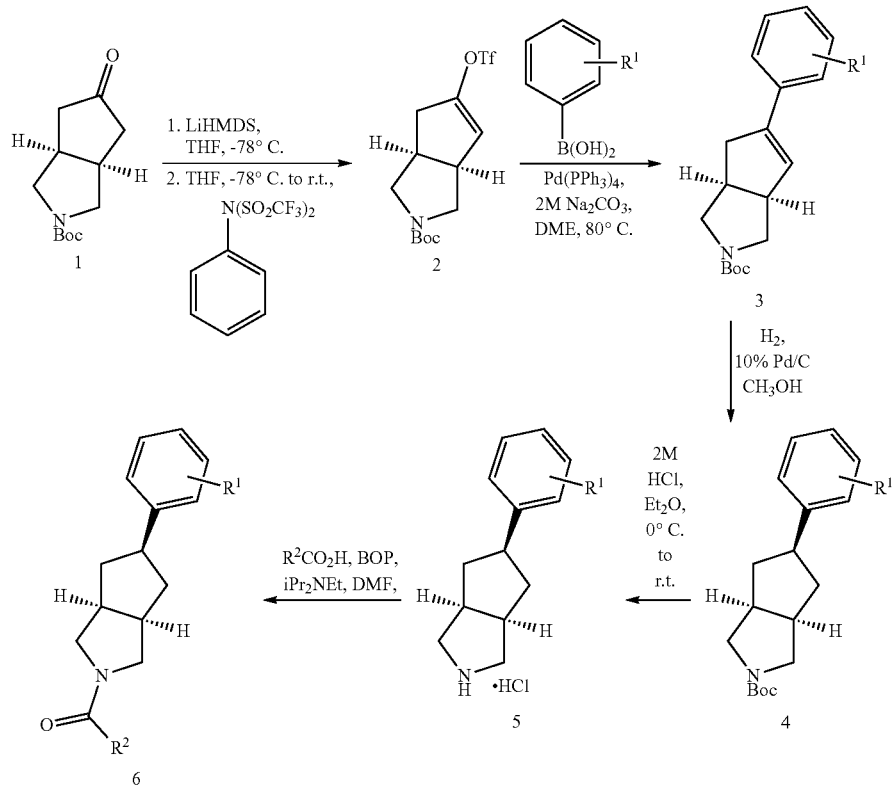

General Procedure:

Step 1: Lithium bis(trimethylsilyl)amide (LiHMDS) was added via syringe to a yellow-orange solution of tert-butyl-5-oxooctahydrocyclopenta[c]pyrrole-2-carboxylate (1) (1.4 M) in anhydrous tetrahydrofuran (THF), stirred at −78° C. The reaction mixture was stirred at −78° C. for 1 h 45 min, after which a solution of N-phenyltrifluoromethanesulfonimide (0.9 M) in anhydrous THF was added portionwise. The reaction mixture was stirred at −78° C. for another 2 h, after which it was allowed to warm to room temperature. It was concentrated in vacuo and purified via normal phase silica gel column chromatography (0% to 15% ethyl acetate in hexanes).

Step 2: Compound 2 (0.04 M) (1 equiv) and the respective moronic acid (2.5 equiv) were stirred in a 1:2 mixture of 2 M aqueous sodium carbonate and 1,2-dimethoxyethane. The reaction mixture was evacuated and purged with argon. Tetrakis(triphenylphosphine)palladium(0) (0.1 equiv) was added, and the reaction mixture was evacuated and purged with argon. It was heated to and stirred at 80° C. for 6 h, after which it was allowed to cool to room temperature. Ethyl acetate was added and the reaction mixture was concentrated in vacuo. An additional volume of ethyl acetate was added. The organic and aqueous layers were separated. The organic layer was washed with brine (2×) and dried with anhydrous sodium sulfate. The solvent was evaporated in vacuo. The resulting crude material was purified via normal phase silica gel column chromatography (hexanes followed by 20% ethyl acetate in hexanes followed by ethyl acetate).

Step 3: Compound 3 (0.5 M) was stirred in methanol. The reaction mixture was evacuated and purged with argon. 10% Palladium on carbon was added. The reaction mixture was evacuated and purged with argon. Then it was evacuated and purged three times with hydrogen, after which a steady stream of hydrogen was allowed to pass through the reaction mixture. The reaction mixture was stirred overnight, then filtered through a celite pad with methanol. The filtrate was concentrated in vacuo. The resulting crude material was carried on to the next step.

Step 4: Compound 4 (0.7 M) (1 equiv) was stirred in methylene chloride at 0° C. A 2-M solution of HCl in diethyl ether (5.6 equiv) was added portionwise. The reaction mixture was allowed to warm to room temperature and was stirred overnight. Subsequent addition of diethyl ether resulted in the formation of a precipitate, which was isolated via vacuum filtration.

Step 5: The hydrochloric acid salt, 5, (0.14 M) (1 equiv), the respective carboxylic acid (1 equiv), and (benzotriazol-1-yloxy)tris(dimethylamino)phosphonium hexafluorophosphate (BOP) (1.5 equiv) were stirred in anhydrous DMF at room temperature. Diisopropylethylamine (3.0 equiv) was added via syringe. The reaction mixture was stirred overnight, after which distilled water was added. The resulting precipitate was isolated via vacuum filtration.

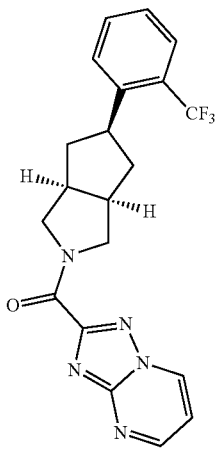 [SMILES: O=C(c1nc2ncccn2n1)N1C[C@H]2C[C@@H](c3ccccc3C(F)(F)F)C[C@H]2C1]

7a: Off-white solid; Yield: 87%; 1H NMR (400 MHz, (CDCl3)): δ 8.95 (d, J=6.8 Hz, 1H), 8.92 (dd, J=3.6, 1.6 Hz, 1H), 7.60 (d, J=8.0 Hz, 1H), 7.51 (d, J=6.0 Hz, 2H), 7.28 (d, J=7.2 Hz, 1H), 7.24 (dd, J=6.8, 4.8 Hz, 1H), 4.17 (s, 2H), 3.93 (d, J=5.6 Hz, 2H), 3.56-3.50 (m, 1H), 2.95-2.88 (m, 2H), 2.37 (doublet of pentets, J=37.6, 6.8 Hz, 2H), 1.69-1.57 (m, 2H); 13C NMR (101 MHz, (CDCl3)): δ 161.6, 159.4, 155.7, 155.0, 142.9, 136.5, 132.3, 128.0 (2C), 126.2, 125.8 (2C), 111.5, 54.2, 52.6, 44.1, 43.0, 41.6, 41.4, 41.1; LC-MS (M$^+$+H): 402; EI+ HRMS (m/z): [M]+ calcd. for C20H18N5OF3: 401.14635. Found: 401.14615.

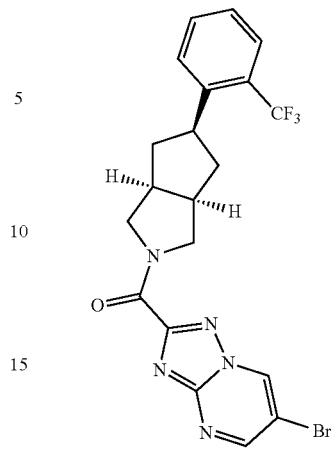

7c: Orange solid; Yield: 78%; 1H NMR (400 MHz, (CDCl3)): δ 9.05 (d, J=2.4 Hz, 1H), 8.91 (d, J=2.4 Hz, 1H), 7.61 (d, J=7.2 Hz, 1H), 7.52 (s, 2H), 7.31-7.28 (m, 1H), 4.14 (d, J=5.6 Hz, 1H), 3.93 (d, J=5.6 Hz, 1H), 3.55-3.49 (m, 1H), 2.96-2.86 (m, 2H), 2.62 (d, J=8.8 Hz, 1H), 2.37 (doublet of pentets, J=36.4, 7.2 Hz, 2H), 1.69-1.56 (m, 3H); LC-MS (M$^+$+H): 480; EI+ HRMS (m/z): [M]+ calcd. for C20H17N5OBrF3: 479.05686. Found: 479.05726.

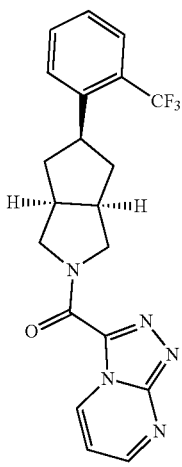

7b: Off-white solid; Yield: 72%; 1H NMR (400 MHz, (CDCl3)): δ 8.95 (dd, J=6.8, 2.0 Hz, 1H), 8.92 (dd, J=4.4, 2.0 Hz, 1H), 7.60 (d, J=8.0 Hz, 1H), 7.51 (d, J=6.8 Hz, 2H), 7.30-7.27 (m, 1H), 7.23 (dd, J=7.2, 4.4 Hz, 1H) 4.18-4.17 (m, 2H), 3.93 (d, J=6.0 Hz, 1H), 3.56-3.49 (m, 1H), 2.95-2.86 (m, 2H), 2.37 (doublet of pentets, J=36.8, 7.2 Hz, 2H), 1.69-1.57 (m, 3H); 13C NMR (101 MHz, (CDCl3)): δ 161.6, 159.4, 155.7 (2C), 136.5 (2C), 132.2, 128.0 (2C), 126.2 (3C), 111.5, 54.2, 52.6, 44.2, 43.0, 41.6, 41.4, 41.2; LC-MS (M$^+$+H): 402; EI+ HRMS (m/z): [M]+ calcd. for C20H18N5OF3: 401.14635. Found: 401.14542.

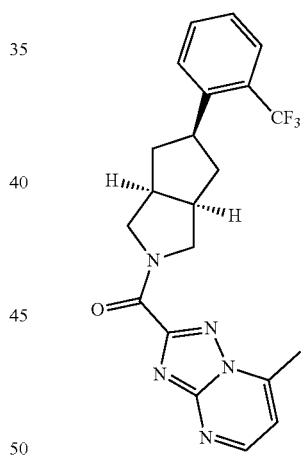

7d: Pale-pink solid; Yield: 98%; 1H NMR (400 MHz, (CDCl3)): δ 8.77 (d, J=4.8 Hz, 1H), 7.60 (d, J=7.6 Hz, 1H), 7.54 (d, J=8.0 Hz, 1H), 7.50 (d, J=8.0 Hz, 1H), 7.28 (d, J=7.6 Hz, 1H), 7.04 (d, J=3.6 Hz, 1H), 4.14 (d, J=5.6 Hz, 2H), 3.93 (d, J=5.6 Hz, 2H), 3.57-3.48 (m, 1H), 2.94 (s, 3H), 2.92-2.86 (m, 2H), 2.36 (doublet of pentets, J=41.2, 6.4 Hz, 2H), 1.69-1.58 (m, 2H); 13C NMR (101 MHz, (CDCl3)): δ 161.0, 154.9 (2C), 132.2 (2C), 128.0 (2C), 126.2 (2C), 125.8 (2C), 111.0, 54.2, 52.5, 44.1, 43.0, 41.7, 41.5, 41.1, 17.6; LC-MS (M$^+$+H): 416; EI+ HRMS (m/z): [M]+ calcd. for C21H20N5OF3: 415.16200. Found: 415.16092.

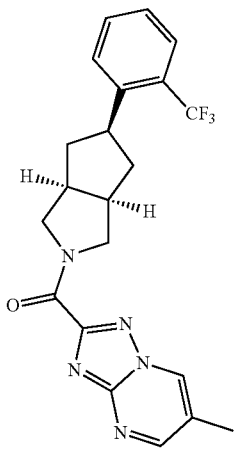 [SMILES: Cc1cnc2nc(C(=O)N3C[C@H]4C[C@@H](c5ccccc5C(F)(F)F)C[C@H]4C3)nn2c1]

7e: Pale-orange solid; Yield: 89%; 1H NMR (400 MHz, (CDCl3)): δ 8.77 (d, J=2.4 Hz, 1H), 8.70 (s, 1H), 7.60 (d, J=8.0 Hz, 1H), 7.53-7.46 (m, 2H), 7.28 (d, J=7.6 Hz, 1H), 4.21-4.12 (m, 2H), 3.92 (d, J=5.6 Hz, 2H), 3.57-3.48 (m, 1H), 2.95-2.83 (m, 2H), 2.51 (s, 3H), 2.36 (doublet of pentets, J=36.0, 6.8 Hz, 2H), 1.68-1.56 (m, 2H); 13C NMR (101 MHz, (CDCl3)): δ 161.1, 159.6, 158.0, 153.9, 142.9, 134.2, 132.2, 128.0, 126.2, 125.9, 125.8, 125.7, 121.8, 54.2, 52.6, 44.2, 43.0, 41.6, 41.4, 41.1, 15.6; LC-MS (M$^+$+H): 416; EI+ HRMS (m/z): [M]+ calcd. for C21H20N5OF3: 415.16200. Found: 415.16163.

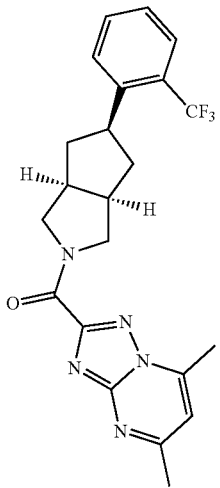 [SMILES: Cc1cc(C)n2nc(C(=O)N3C[C@H]4C[C@@H](c5ccccc5C(F)(F)F)C[C@H]4C3)nc2n1]

7f: Pale-orange solid; Yield: 38%; 1H NMR (400 MHz, (CDCl3)): δ 7.60 (d, J=8.0 Hz, 1H), 7.51 (dd, J=14.4, 7.6 Hz, 2H), 7.28 (d, J 7.6 Hz, 1H), 6.90 (s, 1H), 4.19 (dd, J=12.4, 3.2 Hz, 1H), 4.13 (dd, J=12.4, 6.8 Hz, 1H), 3.92 (d, J=5.2 Hz, 2H), 3.55-3.49 (m, 1H), 2.87 (s, 3H), 2.70 (s, 3H), 2.64 (d, J=9.6 Hz, 1H), 2.35 (doublet of pentets, J=40.0, 6.8 Hz, 2H), 1.69-1.56 (m, 3H); 13C NMR (101 MHz, (CDCl3)): δ 165.9, 160.7, 160.0, 147.5 (2C), 132.3, 128.0 (2C), 126.2 (2C), 125.8 (2C), 111.9, 54.3, 52.5, 44.1, 43.0, 41.7, 41.5, 41.1, 25.3, 17.3; LC-MS (M$^+$+H): 430; EI+ HRMS (m/z): [M]+ calcd. for C22H22N5OF3: 429.17765. Found: 429.17711.

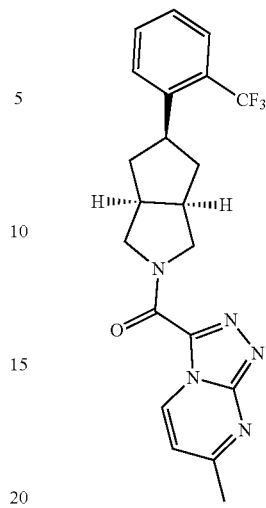

7g: Off-white solid; Yield: 70%; 1H NMR (400 MHz, (CDCl3)): δ 8.77 (d, J=4.4 Hz, 1H), 7.60 (d, J=8.0 Hz, 1H), 7.53 (d, J=8.0 Hz, 1H), 7.49 (d, J=7.6 Hz, 1H), 7.28 (d, J=8.0 Hz, 1H), 7.04 (d, J 4.4 Hz, 1H), 4.14 (d, J=5.6 Hz, 2H), 3.93 (d, J=6.0 Hz, 2H), 3.57-3.47 (m, 1H), 2.93 (s, 3H), 2.92-2.83 (m, 2H), 2.37 (doublet of pentets, J=41.2, 6.4 Hz, 2H), 1.69-1.56 (m, 2H); 13C NMR (101 MHZ, (CDCl3)): δ 160.9, 159.9, 155.2, 155.0, 148.9, 142.9, 132.2, 128.0, 126.2, 125.8 (2C), 125.7, 123.4, 111.0, 54.2, 44.1, 43.0, 41.6, 41.4, 41.1, 17.5; LC-MS (M$^+$+H): 416.

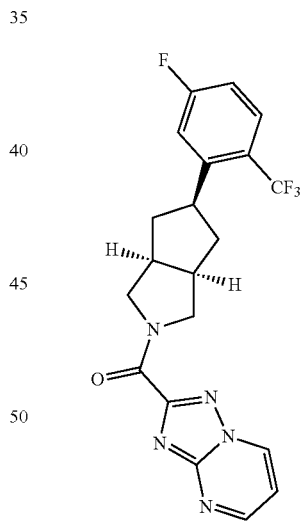

7h: Tan solid; Yield: 59%; 1H NMR (400 MHz, (CDCl3)): δ 8.95 (dd, J=4.8, 2.0 Hz, 1H), 8.92 (dd, J=3.6, 2.0 Hz, 1H), 7.60 (dd, J=8.8, 6.0 Hz, 1H), 7.23 (dd, J=6.8, 4.0 Hz, 1H), 7.19 (d, J=10.8 Hz, 1H), 6.96 (t, J=6.0 Hz, 1H), 4.18 (d, J=4.4 Hz, 2H), 3.93 (d, J=4.8 Hz, 2H), 3.52-3.49 (m, 1H), 2.94-2.88 (m, 2H), 2.38 (doublet of pentets, J=30.8, 6.8 Hz, 2H), 1.63-1.53 (m, 2H); 13C NMR (101 MHz, (CDCl3)): δ 161.5, 159.4, 155.7, 155.0, 136.5, 128.4, 115.1, 114.9, 113.5, 113.3, 111.5, 54.2, 52.5, 44.0, 43.0, 41.6, 41.4, 41.1; LC-MS (M$^+$+H): 420.

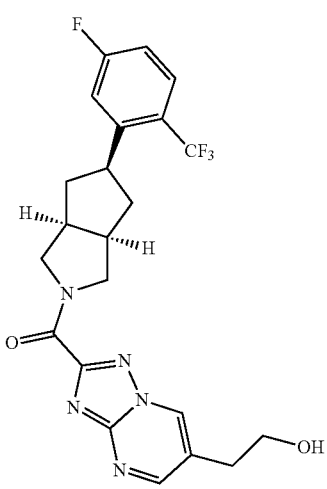 [SMILES: O=C(c1nc2ncc(CCO)cn2n1)N1C[C@H]2C[C@@H](c3cc(F)ccc3C(F)(F)F)C[C@H]2C1]
7i: Tan solid; Yield: 60%; 1H NMR (400 MHz, ((CD$_3$)$_2$SO): δ 8.94 (s, 1H), 8.83 (s, 1H), 7.69-7.52 (m, 1H), 7.21 (d, J=12.0 Hz, 1H), 6.95 (s, 1H), 4.18 (s, 2H), 4.01 (s, 2H), 3.91 (s, 2H), 3.51 (s, 1H), 3.03 (s, 2H), 2.90 (s, 2H), 2.50-2.32 (m, 2H), 1.41-1.25 (m, 3H); LC-MS (M$^+$+H): 464; EI+ HRMS (m/z): [M]+ calcd. for C22H21N5O2F4: 463.16314. Found: 463.16196.
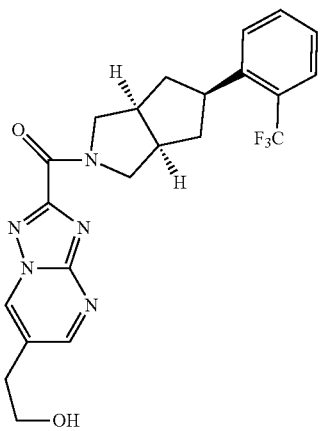 [SMILES: O=C(c1nc2ncc(CCO)cn2n1)N1C[C@H]2C[C@@H](c3ccccc3C(F)(F)F)C[C@H]2C1]
7j: 1H NMR (400 MHz, CDCl3): δ 8.7 (s, broad, 2H), 7.5 (d, 1H), 7.4 (m, 2H), 7.2 (m, 1H), 4.2 (m, 2H), 4.0 (m, 2H), 3.9 (m, 2H), 3.5 (m, 1H), 3.3 (m, 2H), 2.9 (m, 2H), 2.3 (m, 2H), 1.5 (m, 2H). MS: 446 (M+1)
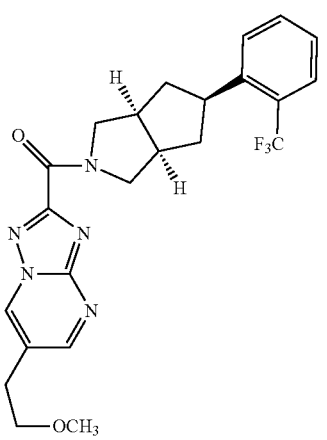 [SMILES: COCCc1cnc2nc(C(=O)N3C[C@H]4C[C@@H](c5ccccc5C(F)(F)F)C[C@H]4C3)nn2c1]
7k: 1H NMR (400 MHz, CDCl3): δ 8.7 (s, broad, 2H), 7.5 (d, 1H), 7.4 (m, 2H), 7.2 (m, 1H), 4.1 (m, 4H), 3.8 (m, 2H), 3.6 (m), 3.4 (s, 3H), 3.3 (m, 2H), 2.9 (m, 2H), 2.3 (m, 2H), 1.5 (m). MS: 460 (M+1)
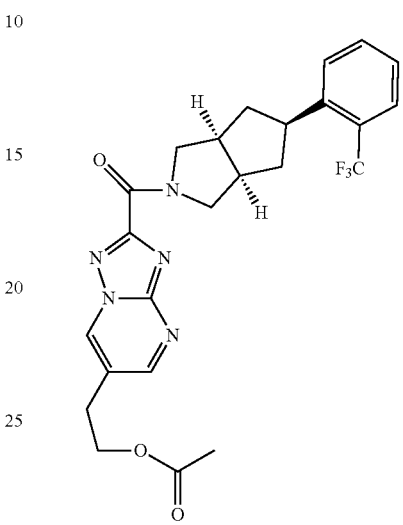
7l: 1H NMR (400 MHz, CDCl3): δ 8.7 (s, broad, 2H), 7.5 (d, 1H), 7.4 (m, 2H), 7.2 (m, 1H), 4.3 (t, 2H), 4.1 (m, 2H), 3.8 (m, 2H), 3.4 (m, 1H), 3.0 (t, 2H), 2.8 (m, 2H), 2.3 (m, 2H), 2.0 (s, 3H), 1.5 (m). MS: 488 (M+1)
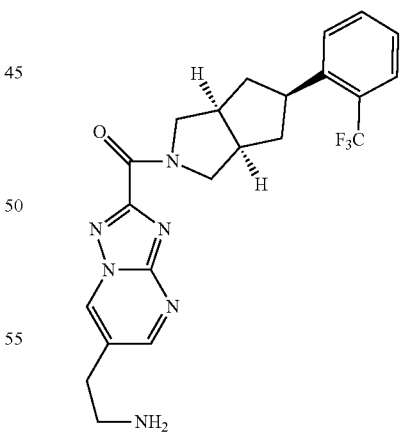
7m: 1H NMR (400 MHz, CDCl3): δ 8.7 (s, broad, 2H), 7.5 (d, 1H), 7.4 (m, 2H), 7.2 (m, 1H), 4.1 (m, 2H), 3.8 (m, 2H), 3.6 (m), 3.3 (m, 2H), 2.9-2.8 (m, 4H), 2.3 (m, 2H), 1.5 (m). MS: 445 (M+1)

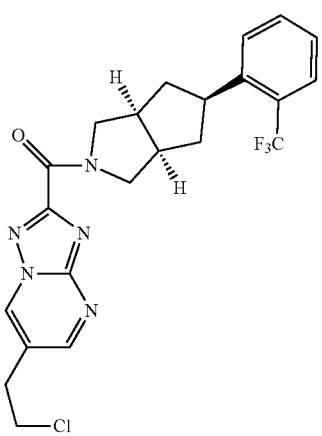 [SMILES: O=C(c1nc2ncc(CCCl)cn2n1)N1C[C@H]2C[C@@H](c3ccccc3C(F)(F)F)C[C@H]2C1]

7n: 1H NMR (400 MHz, CDCl3): δ 8.7 (s, broad, 2H), 7.5 (d, 1H), 7.4 (m, 2H), 7.2 (m, 1H), 4.1 (m, 4H), 3.8 (m, 2H), 3.6 (m), 3.3 (m, 2H), 2.9 (m, 2H), 2.3 (m, 2H), 1.5 (m). MS: 464 (M+1)

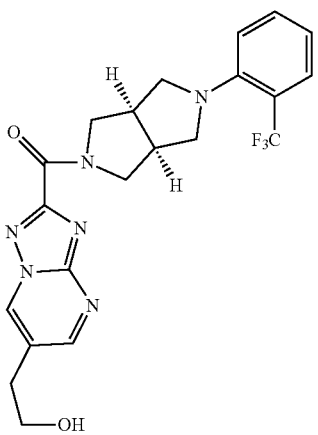 [SMILES: O=C(c1nc2ncc(CCO)cn2n1)N1C[C@@H]2CN(c3ccccc3C(F)(F)F)C[C@@H]2C1]

7o: 1H NMR (400 MHz, CDCl3): δ 8.9 (s, 1H), 8.8 (s, 1H), 7.4 (m, 1H), 7.3 (m, 1H), 7.0 (m, 1H), 6.9 (m, 1H), 4.3 (m, 2H), 4.0 (m, 2H), 3.8 (m, 2H), 3.6 (m, 2H), 3.4 (m, 2H), 3.2 (m, 2H), 2.9 (m, 2H). MS: 447 (M+1)

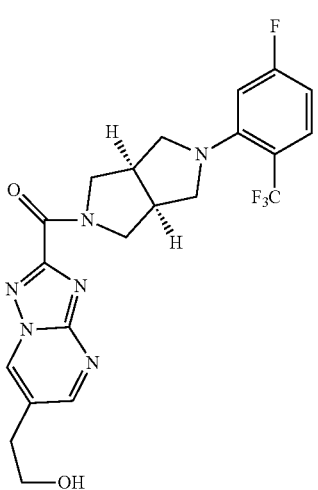 [SMILES: O=C(c1nc2ncc(CCO)cn2n1)N1C[C@@H]2CN(c3cc(F)ccc3C(F)(F)F)C[C@@H]2C1]

7p: 1H NMR (400 MHz, CDCl3): δ 8.9 (s, 1H), 8.8 (s, 1H), 7.4 (m, 1H), 6.7 (m, 1H), 6.6 (m, 1H), 4.3 (m, 2H), 4.0 (m, 2H), 3.8 (m, 2H), 3.6 (m, 2H), 3.4 (m, 2H), 3.2 (m, 2H), 2.9 (m, 2H). MS: 465 (M+1)

Example 2: RPB4 Assay

The compounds listed below were tested in two in vitro assays, RBP4 binding (SPA) and retinol-dependent RBP4-TTR interaction (HTRF) (Table 1). The compounds bound to RBP4 and/or antagonized retinol-dependent RBP4-TTR interaction. This activity indicates that the compounds reduce the levels of serum RBP4 and retinol.

TABLE 1

| Compound | SPA binding assay for RBP4 -IC$_{50}$ (μM) | HTRF assay for antagonists of RBP4-TTR interaction - IC$_{50}$ (μM) |
|---|---|---|
| 7g | 0.045 | 0.415 |
| 7b | 0.046 | 0.661 |
| 7a | 0.023 | 0.209; 0.194; 0.240 |
| 7f | 0.108 | 4.58; 7.44 |
| 7d | 0.122 | 1.85; 2.80 |
| 7c | 0.039 | 0.949 |
| 7d | 0.122 | 0.306 |
| 7j | 0.016 | 0.200 |
| 7k | 0.067 | 1.012 |
| 7l | 0.023 | 0.23 |
| 7m | 0.247 | 1.465 |
| 7n | 0.067 | 0.628 |
| 7h | 0.038 | 0.41 |
| 7i | — | 0.494 |
| 7o | 0.022 | 0.257 |
| 7p | 0.037 | 0.150 |
| 7q | 0.031 | 0.491 |
| 7r | 0.044 | 2.05; 2.19 |
| 7s | 0.025 | 0.626; 0.703 |

Example 3: PPARγ Assay

The compounds of the present invention are advantageous in that they were tested in a PPARγ agonist assay and were inactive as PPARγ agonists (Table 2). PPARγ activation has been implicated as a cause of weight gain in humans (43). The compounds of the present invention do not substantially activate PPARγ, thereby avoiding an unwanted side effect, e.g. weight gain, of treatment of the disclosed retinol diseases.

TABLE 2

| Compound | PPAR γ assay (HTRF) for agonist of this nuclear receptor - IC$_{50}$ (μM) |
|---|---|
| 7a | >100 |
| 7b | >100 |
| 7c | >100 |
| 7d | >100 |
| 7e | >100 |
| 7f | >100 |
| 7g | >100 |
| 7h | >100 |
| 7j | >100 |
| 7e | >100 |
| 7k | >100 |
| 7l | >100 |
| 7m | >100 |
| 7n | >100 |
| 7o | >100 |
| 7p | >100 |
| 7q | >100 |
| 7r | >100 |
| 7s | >100 |
| Rosiglitazone (ctl) | 0.056 ± 0.008 |

Example 4: Metabolism Assay

The compounds listed below were tested in various metabolic stability and CYP inhibition assays. The results are described in Table 3.

TABLE 3

| Compound | Metabolic stability in liver microsomes: % Remaining at 30 min, HLM (%) | CYP inhibition, fluorescent, IC$_{50}$: IC$_{50}$, CYP2C9 (μM) | CYP inhibition, fluorescent, IC$_{50}$: IC$_{50}$, CYP2C19 (μM) | CYP inhibition, fluorescent, IC$_{50}$: IC$_{50}$, CYP2D6 (μM) | CYP inhibition, fluorescent, IC$_{50}$: IC$_{50}$, CYP3A4 (μM) |
|---|---|---|---|---|---|
| 7g | 61 | 5.1; >100 | >100 | >100; >100 | >100:>100 |
| 7a | 85 | >100 | >20 | >100 | >100 |
| 7e | 85; 66 | 16.0; 50.0 | >20; >100 | 12.4; 36.0 | 9.8; >100 |
| 7j | 73 | 60 | >100 | >100 | >100 |
| 7o | — | — | >20 | >20 | >20 |
| 7p | 73 | >20 | >20 | >20 | >20 |
| 7q | 26 | — | — | — | — |
| 7s | — | >92 | >100 | >100 | >100 |

Compounds 7a, 7e, 7g and 7p show good metabolic stability and no appreciable CYP P450 inhibition indicating satisfactory drug-like properties.

Example 5: Serum RBP4 Reduction

The main objective of this study was to demonstrate in vivo target engagement and establish a proof of in vivo activity in mice. In order to attain this objective, the effect of oral compound administration was studied in mice. Three doses of compound 7a and two doses of 7p were tested in Balb/c mice assay for reduction of serum RBP4.

Figure 9A:
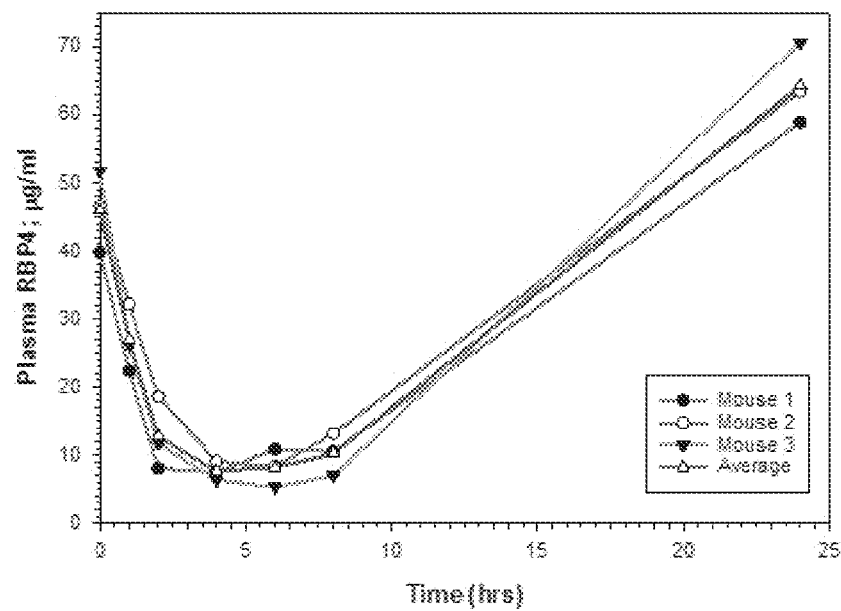
FIG. 9A: Serum RBP4 reduction in mice treated with single 15 mg/kg dose of compound of 7a. Serum RBP4 reduction, absolute values (μg/ml Plasma RBP4). Single dose 15 mg/kg PO, mice, serum RPB4 values.
Figure 9B:
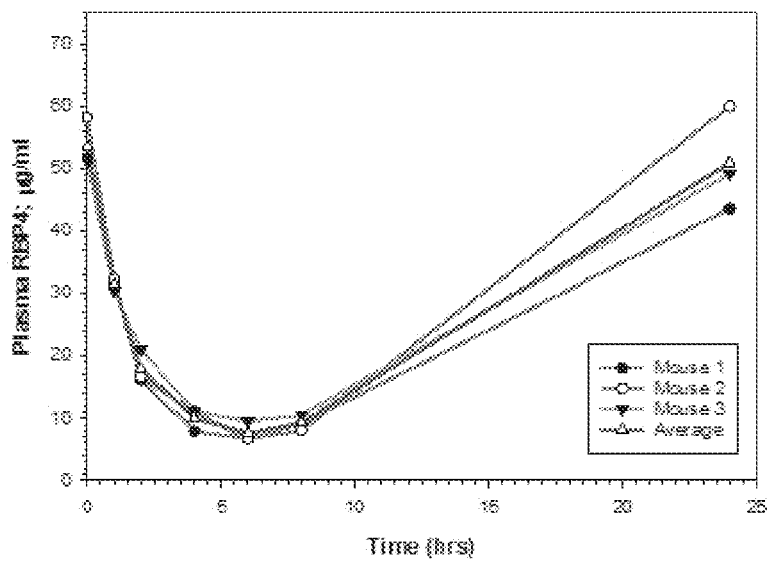
FIG. 9B: Serum RBP4 reduction in mice treated with single 25 mg/kg dose of compound of 7a. Serum RBP4 reduction, absolute values (μg/ml Plasma RBP4). Single dose 25 mg/kg PO, mice, serum RPB4 values.
Figure 9C:
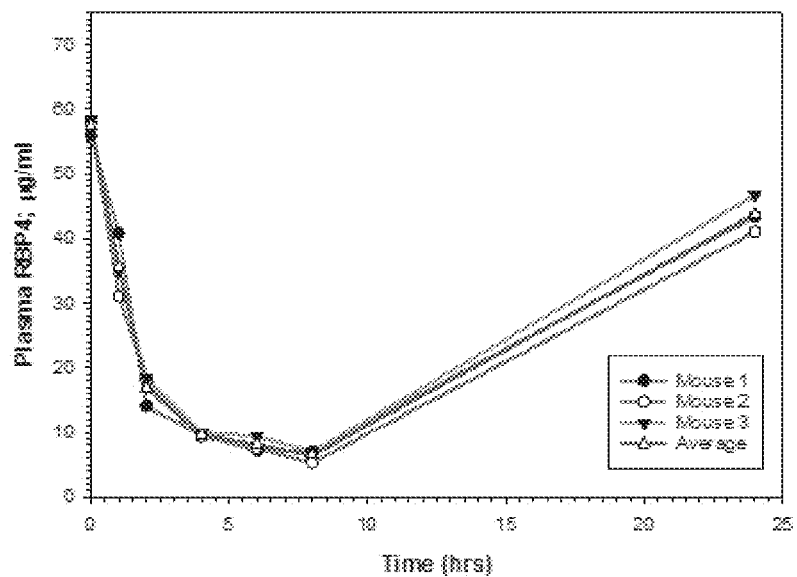
FIG. 9C: Serum RBP4 reduction in mice treated with single 35 mg/kg dose of compound of 7a. Serum RBP4 reduction, absolute values (μg/ml Plasma RBP4). Single dose 35 mg/kg PO, mice, serum RPB4 values.
Figure 9D:
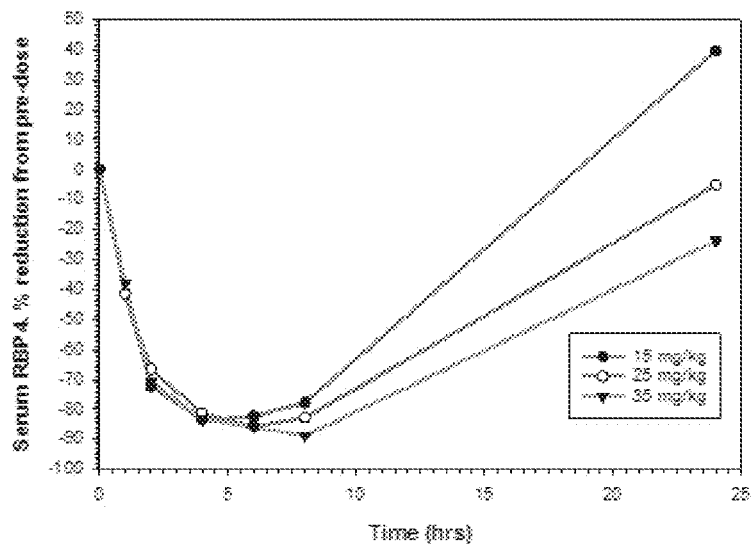

The doses used were 15 mg/kg, 25 mg/kg and 35 mg/kg for 7a (FIGS. 9A-C). At the 15 mg/kg dose, 7a induced a maximum RBP4 reduction of 83% at the 4 hr. At the 25 mg/kg dose, 7a induced a maximum RBP4 reduction of 86% at the 6 hr timepoint. At the 35 mg/kg dose, 7a induced a maximum RBP4 reduction of 89% at the 8 hr timepoint. In summary, 7a induced significant dose-dependent RBP4 lowering in mice (FIG. 9D) with the maximal RBP4 reduction of 89% at the highest dose.

Figure 10A:
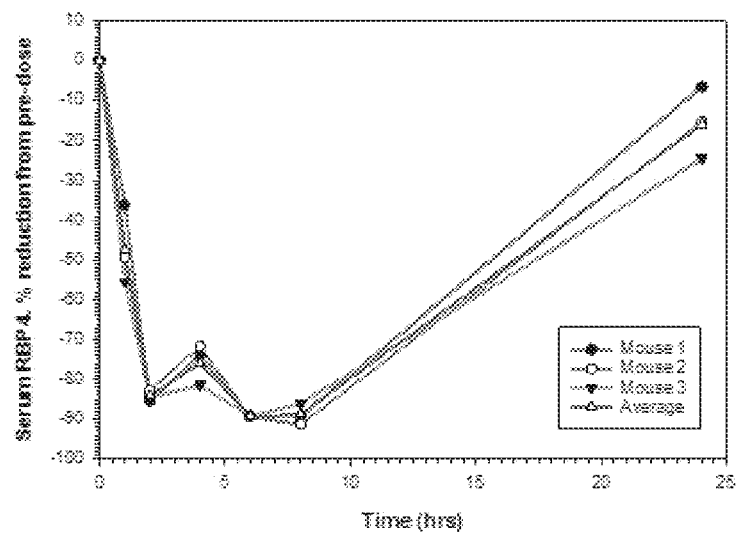
FIG. 10A: Serum RBP4 reduction in mice treated with single 25 mg/kg dose of compound of 7p. Serum RBP4 reduction, absolute values (μg/ml Plasma RBP4). Single dose 25 mg/kg PO, mice, serum RPB4 values.
Figure 10B:
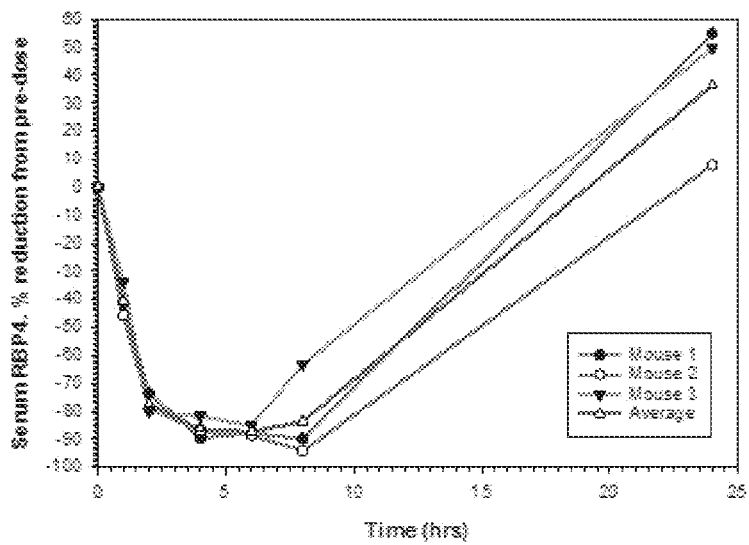
FIG. 10B: Serum RBP4 reduction in mice treated with single 35 mg/kg dose of compound of 7p. Serum RBP4 reduction, absolute values (μg/ml Plasma RBP4). Single dose 35 mg/kg PO, mice, serum RPB4 values.

Two doses, 25 mg/kg and 35 mg/kg, were tested for 7p (FIGS. 10A-B). At the 25 mg/kg dose, 7p induced a maximum RBP4 reduction of 89% at the 6 hr timepoint. At the 35 mg/kg dose, 7p induced a maximum RBP4 reduction of 87% at the 6 hr timepoint. Overall, at both doses 7p induced robust reduction of serum RBP4.

Example 6: RPB4 Binding of Additional Compounds

An additional aspect of the invention provides analogs of the compounds 7a and 7p containing similar "B" groups that are active as RBP4 antagonists. These compounds analogously bind to RBP4 and antagonize retinol-dependent RBP4-TTR interaction without substantially activating PPARγ.

Example 7: Efficacy in a Mammalian Model

Age-dependent accumulation of cytotoxic lipofuscin in the RPE matches the age-dependent increase in the prevalence of the atrophic (dry) form of age-related macular degeneration (AMD) and represents an important pathogenic factor in etiology and progression of dry AMD. Excessive accumulation of toxic lipofuscin in the retina represents a primary pathologic defect in Stargardt disease. Lipofuscin bisretinoids (exemplified by bisretinoid N-retinylidene-N-retinylethanolamine, A2E) mediate lipofuscin toxicity in the AMD and Stargardt disease retina. Enhanced bisretincid synthesis and excessive lipofuscin accumulation can be faithfully mimicked in the mouse Abca4$^{-/-}$ model. Genetic ablation of the Abca4 transporter leads to the massive accumulation of toxic lipofuscin pigments in the retinal pigment epithelium.

To assess pre-clinical efficacy of 7a in the mouse Abca4$^{-/-}$ model, the compound was formulated into a standard mouse chow to provide the daily oral dosing of 35 mg/kg. Long-term 8-week dosing of the compound formulated into a chow was conducted in Abca4$^{-/-}$ mice. The second group of age-matched Abca$^{-/-}$ mice was kept on a standard Picolab 5053 chow. The age-matched reference group of C57BL/6J (wild-type control) was used for defining the basal level of A2E in mice in the absence of the Abca4 ablation; the C57BL/6J mice were kept on a standard Picolab 5053 chow. Blood samples for assessing the serum levels of RBP4 were collected at pre-dose and after 8 weeks of treatment.

Figure 11:
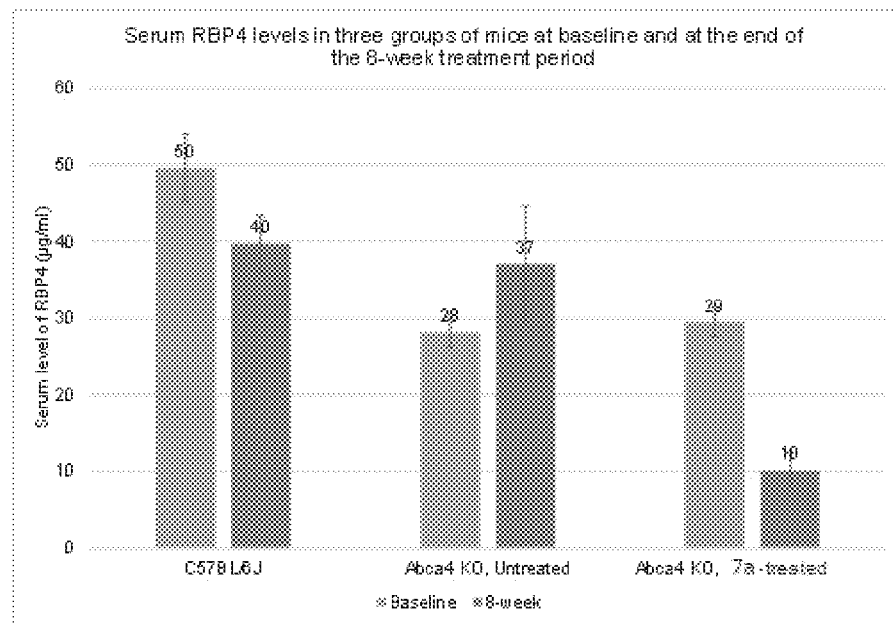
Figure 12:
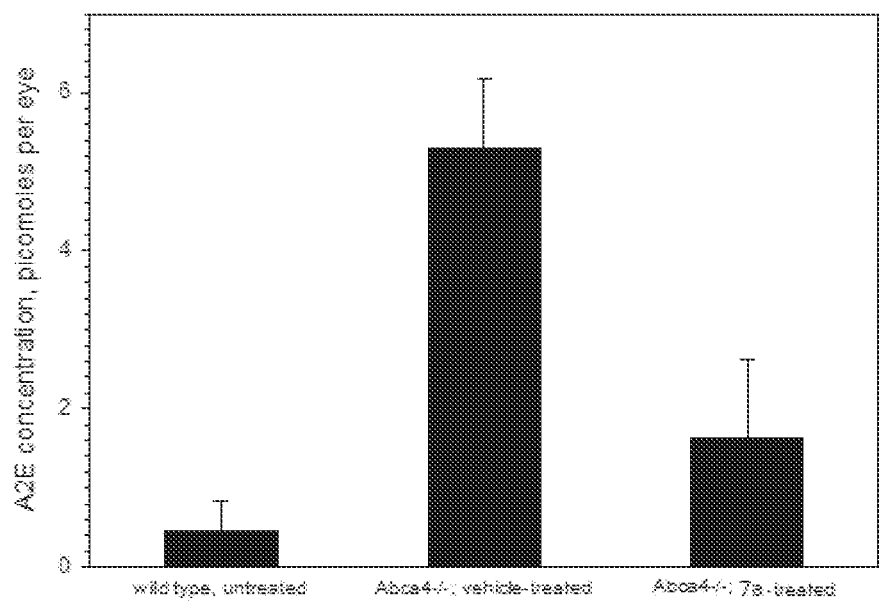
FIG. 12: Effect of 7a treatment on bisretinoid accumulation in eyes of Abca4$^{-/-}$ mice.

Approximately 70% serum RBP4 reduction was documented in 7a treated mice at the end of the 8-week treatment (FIG. 11). RBP4 levels in two other groups did not significantly change. Following the 8 weeks of dosing, the eyecups of treated and untreated Abca4$^{-/-}$ mice, as well as the eyecups of the reference C57BL/6J wild type mice, were collected and subjected to the quantitative A2E analysis. This analysis revealed statistically significant 69% A2E reduction (p=0.0007) in the 7a-treated mice as compared to the control chow-treated Abca4$^{-/-}$ animals (FIG. 12). This significant inhibition of bisretinoid synthesis in treated animals provided evidence of pre-clinical efficacy of AKR-XI-85 in the mouse Abca4$^{-/-}$ model of enhanced retinal lipofuscinogenesis.

An amount of a compound of the present application is administered to the eye of a subject afflicted with Age-Related Macular Degeneration, dry (atrophic) Age-Related Macular Degeneration, Stargardt Disease, Best disease, adult vitelliform maculopathy or Stargardt-like macular dystrophy. The amount of the compound is effective to treat the subject.

Example 8: Significance of Nitrogen Positions

The following compounds were tested in two in vitro assays, RBP4 binding (SPA) and retinol-dependent RBP4-TTR interaction (HTRF) (Table 4). The compounds were significantly less active than the compounds listed in Table 1.

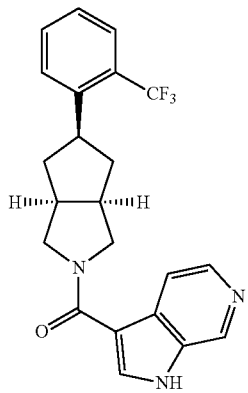

(8a)

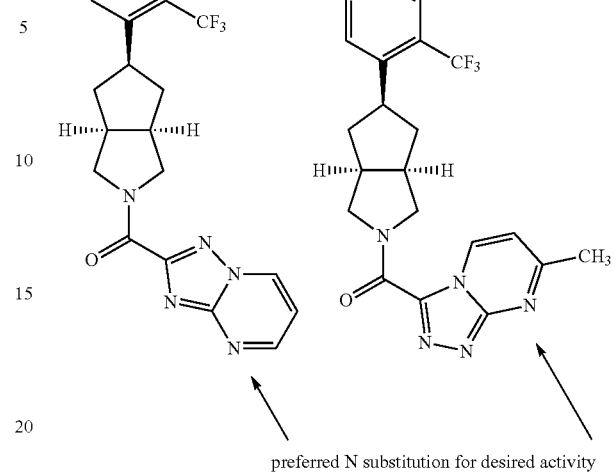

(8b)

TABLE 4

| Compound | SPA binding assay for RBP4 - IC$_{50}$ (μM) | HTRF assay for antagonists of RBP4-TTR interaction - IC$_{50}$ (μM) |
| --- | --- | --- |
| 8a | >3 | >30 |
| 8b | >3 | >30 |

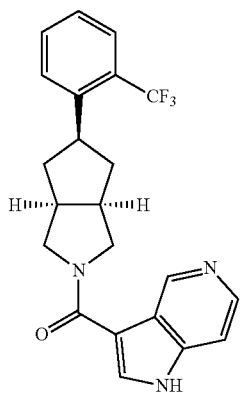

Without being bound by any specific theory, it is believed that the position of the N on the biaryl ring of compounds 8a and 8b reduces activity relative to, for example, compound 7a. The claimed compounds each containing a N at a position analogous to compounds 7a and 7g (below) have improved activity in RBP4 assays and reduced or no substantial activity in PPARγ assays.

preferred N substitution for desired activity

Example 9: RPB4 Assay of Additional Compounds

The compounds listed below were prepared using the procedure described herein and tested in two in vitro assays, RBP4 binding (SPA) and retinol-dependent RBP4-TTR interaction (HTRF) (Table 5). The compounds bound to RBP4 and/or antagonized retinol-dependent RBP4-TTR interaction. This activity indicates that the compounds reduce the levels of serum RBP4 and retinal.

TABLE 5

| Compound | SPA binding assay for RBP4 -IC$_{50}$ (μM) | HTRF assay for antagonists of RBP4-TTR interaction - IC$_{50}$ (μM) |
| --- | --- | --- |
| 9a | 0.0273 | 1.1 |
| 9b | 0.0395 | 0.45 |
| 9c | 0.0829 | 1.13 |
| 9d | 0.0881 | 1.45 |
| 9e | 0.0346 | 0.604 |
| 9f | 0.0571 | 0.45 |
| 9g | 0.0784 | 0.741 |
| 9h | 0.104 | 2.48 |
| 9i | 0.443 | 20.4 |
| 9j | 0.019 | 0.551 |
| 9j | 0.0409 | 0.473 |
| 10a | 14.8 | 0.617 |
| 10b | 2.46 | 0.103 |
| 10c | 1.92 | 0.0408 |
| 10d | 4.53 | 0.3 |

Discussion

Age-related macular degeneration (AMD) is the leading cause of blindness in developed countries. Its prevalence is higher than that of Alzheimer's disease. There is no treatment for the most common dry form of AMD. Dry AMD is triggered by abnormalities in the retinal pigment epithelium (RPE) that lies beneath the photoreceptor cells and provides critical metabolic support to these light-sensing cells. RPE dysfunction induces secondary degeneration of photoreceptors in the central part of the retina called the macula. Experimental data indicate that high levels of lipofuscin induce degeneration of RPE and the adjacent photoreceptors in atrophic AMD retinas. In addition to AMD, dramatic accumulation of lipofuscin is the hallmark of Stargardt's disease (STGD), an inherited form of juvenile onset macular degeneration. One of the major cytotoxic components of RPE lipofuscin is a pyridinium bisretinoid A2E. A2E formation occurs in the retina in a non-enzymatic manner and can be considered a by-product or a properly functioning visual cycle. Given the established cytotoxic effects of A2E on RPE and photoreceptors, inhibition of A2E formation could lead to delay in visual loss in patients with dry AMD and STGD. It was suggested that small molecule visual cycle modulators may reduce the formation of A2E in the retina and prolong RPE and photoreceptor survival in patients with dry AMD and STGD. Rates of the A2E production in the retina depend on the influx of all-trans retinol from serum to the RPE. RPE retinol uptake depends on serum retinol concentrations. Pharmacological down-regulation of serum retinol is a valid treatment strategy for dry AMD and STGD. Serum retinol is maintained in circulation as a tertiary complex with retinol-binding protein (RBP4) and transthyretin (TTR). Without interacting with TTR, the RBP4-retinol complex is rapidly cleared due to glomerular filtration. Retinol binding to RBP4 is required for formation of the RBP4-TTR complex; apo-RBP4 does not interact with TTR. Importantly, the retinol-binding site on RBP4 is sterically proximal to the interface mediating the RBP4-TTR interaction. Without wishing to be bound by any scientific theory, the data herein show that small molecule RBP4 antagonists displacing retinol from RBP4 and disrupting the RBP4-TTR interaction will reduce serum retinol concentration, inhibit retinol uptake into the retina and act as indirect visual cycle inhibitors reducing the formation of cytotoxic A2E.

Figure 4:
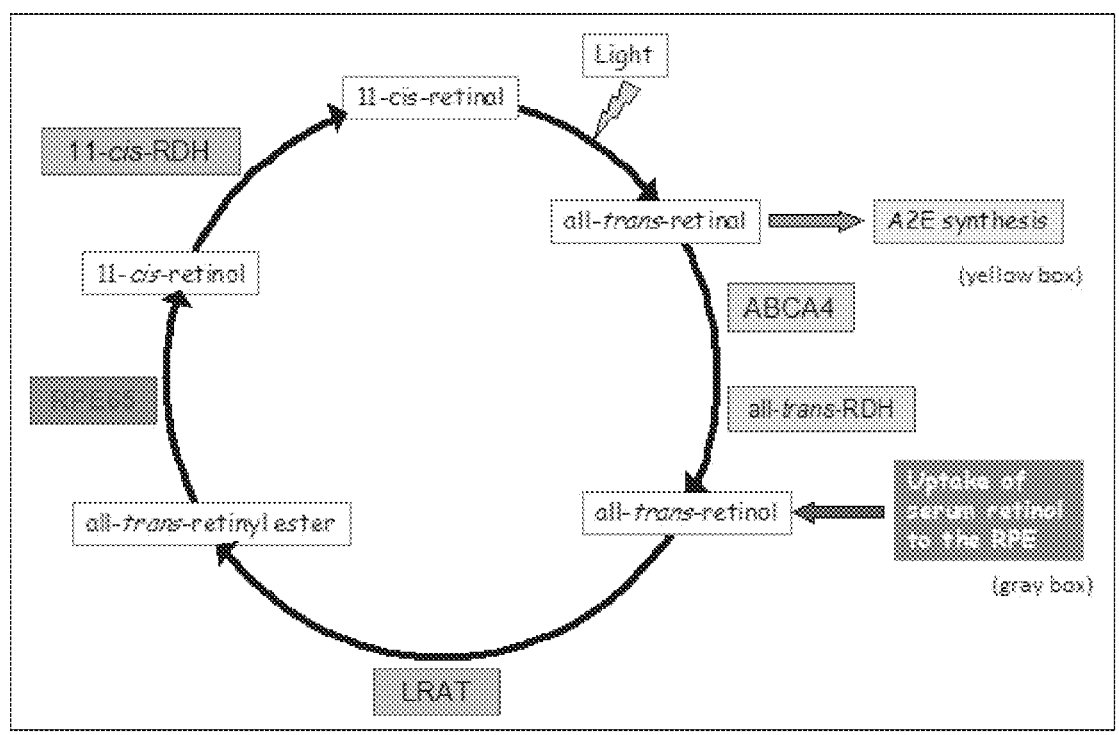
FIG. 4. Visual cycle and biosynthesis of A2E. A2E biosynthesis begins when a portion of all-trans-retinal escapes the visual cycle (yellow box) and non-enzymatically reacts with phosphatidyl-ethanolamine forming the A2E precursor, A2-PE. Uptake of serum retinol to the RPE (gray box) fuels the cycle.
Figure 5:
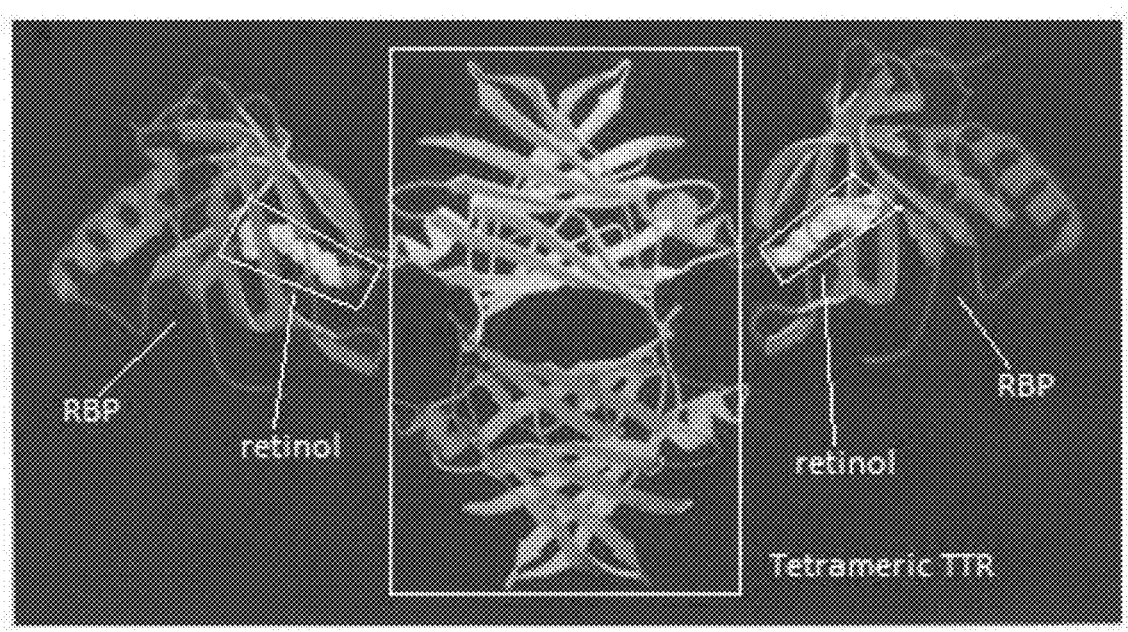
FIG. 5. Three-dimensional structure of the RBP4-TTR-retinol complex. Tetrameric TTR is shown in blue, light blue, green and yellow (large boxed region). RBP is shown in red (unboxed region) and retinol is shown in gray (small boxed region) (28).

As rates of the A2E production in the retina depend on the influx of all-trans retinol from serum to the RPE (FIG. 4), it has been suggested that partial pharmacological down-regulation of serum retinol may represent a target area in dry AMD treatment (11). Serum retinol is bound to retinol-binding protein (RBP4) and maintained in circulation as a tertiary complex with RBP4 and transthyretin (TTR) (FIG. 5). Without interacting with TTR, the RBP4-retinol complex is rapidly cleared from circulation due to glomerular filtration. Additionally, formation of the RBP4-TTR-retinol complex is required for receptor-mediated all-trans retinol uptake from serum to the retina.

Without wishing to be bound by any scientific theory, visual cycle modulators may reduce the formation of toxic bisretinoids and prolong RPE and photoreceptor survival in dry AMD. Rates of the A2E production depend on the influx of all-trans retinol from serum to the RPE. Formation of the tertiary retinol-binding protein 4 (RBP4)-transthyretin (TTR)-retinol complex in serum is required for retinol uptake from circulation to the RPE. Retinol-binding site on RBP4 is sterically proximal to the interface mediating the RBP4-TTR interaction. RBP4 antagonists that compete with serum retinol for binding to RBP4 while blocking the RBP4-TTR interaction would reduce serum retinol, partially reduce visual cycle retinoid concentration, and inhibit the formation of cytotoxic bisretinoids.

RBP4 represents an attractive drug target for indirect pharmacological modulation of the visual cycle and A25 formation. The retinol-binding site on RBP4 is sterically proximal to the interface mediating the RBP4-TTR interaction. Retinol antagonists competing with serum retinol for binding to RBP4 while blocking the RBP4-TTR interaction would reduce serum RBP4 and retinal levels which would lead to reduced uptake of retinol to the retina. The outcome would be visual cycle modulation which is manifested in partial reduction of visual cycle retinoids that serve as precursors of bisretinoid synthesis with subsequent reduction in the A2E synthesis.

Figure 6:
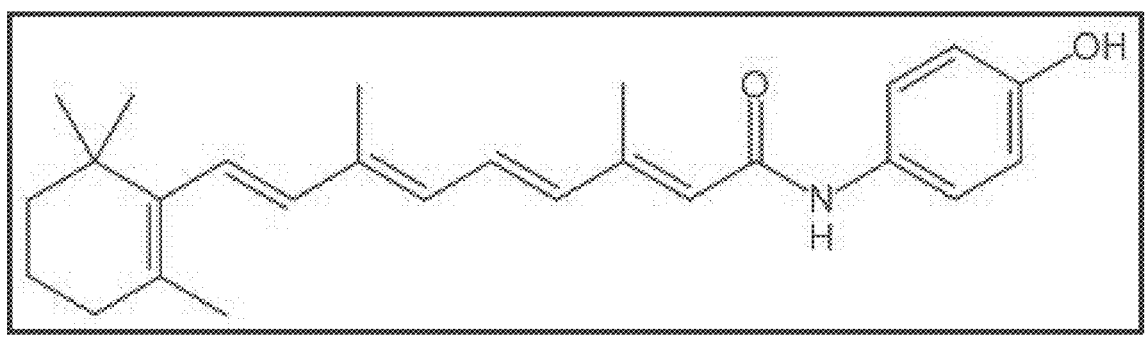
FIG. 6. Structure of fenretinide, [N-(4-hydroxyphenyl)retinamide, 4HRP], a retinoid RBP4 antagonist.

A synthetic retinoid called fenretinide [N-(4-hydroxyphenyl)retinamide, 4HRP] (FIG. 6) previously considered as a cancer treatment (29) was found to bind to RBP4, displace all-trans retinol from RBP4 (13), and disrupt the RBP4-TTR interaction (13,14).

Fenretinide was shown to reduce serum RBP4 and retinol (15), inhibit ocular all-trans retinol uptake and slow down the visual cycle (11). Importantly, fenretinide administration reduced A2E production in an animal model of excessive bisretinoid accumulation, Abca4 –/– mice (11). Pre-clinical experiments with fenretinide validated RBP4 as a drug target for dry AMD. However, fenretinide is non-selective and toxic. Independent of its activity as an antagonist of retinol binding to RBP4, fenretinide is an extremely active inducer of apoptosis in many cell types (16-19), including the retinal pigment epithelium cells (20). It has been suggested that fenretinide's adverse effects are mediated by its action as a ligand of a nuclear receptor RAR (21-24). Additionally, similar to other retinoids, fenretinide is reported to stimulate formation of hemangiosarcomas in mice. Moreover, fenretinide is teratogenic, which makes its use problematic in Stargardt disease patients of childbearing age.

As fenretinide's safety profile may be incompatible with long-term dosing in individuals with blinding but non-life threatening conditions, identification of new classes of RBP4 antagonists is of significant importance. The compounds of the present invention displace retinol from RBP4, disrupt retinol-induced RBP4-TTR Interaction, and reduce serum REBP4 levels. The compounds of the present invention reduce serum RBP4 concentration in mice and inhibit bisretinoid accumulation in the Abca4 –/– mouse model of excessive lipofuscinogenesis which indicates usefulness a treatment for dry AMD and Stargardt disease.

Peroxisome proliferator-activated receptor gamma (PPARγ) is a ligand-dependent transcription factor that belongs to the nuclear receptor protein family. As most nuclear receptors, PPARγ has a DNA-binding domain (mediates docking to regulatory genomic regions) and ligand-binding domain (LBD) which is responsible for binding small molecule natural or synthetic ligands that change the conformation of the LRD. PPARγ agonists are compounds that bind to the ligand binding domain of this nuclear receptor leading to its conformational changes and recruitment of transcriptional co-activators leading to enhanced expression of the target genes. PPARγ agonists, such as rosiglitazone (brand name Avandia) and pioglitazone (brand name Actos), have been used for treatment of diabetes. However, the clinical use of PPARγ agonists is highly restricted due to their mechanism-based adverse effects such as increased risk of death, myocardial infarction, stroke, congestive heart failure, hepatotoxicity, peripheral edema, weight gain and carcinogenicity (44-47). Our data shows that some of the previously described RBP4 antagonists may act as PPARγ agonists. Cross-reactivity of RBP4 antagonists with PPARγ would be a highly undesirable attribute. The present invention describes potent and selective RBP4 antagonists that lack the PPARγ liability.

The present invention relates to small molecules for the treatment of macular degeneration and Stargardt Disease. Disclosed herein is the ophthalmic use of the small molecule as non-retinoid RBP4 antagonists. The compounds of Examples 1-19 have been shown to bind RBP4 in vitro and/or to antagonize RBP4-TTR interaction in vitro at biologically significant concentrations. Additional compounds described herein, which are analogs of Examples 1-19 analogously bind RBP4 in vitro and antagonize RBP4-TTR interaction in vitro at biologically significant concentrations. The compounds described herein unexpectedly fail to activate PPARγ, which has been implicated to cause weight gain in hum subjects.

Currently, there is no FDA-approved treatment for dry AMD or Stargardt disease, which affects millions of patients. An over the counter, non-FDA-approved cocktail of antioxidant vitamins and zinc (AREDS formula) is claimed to be beneficial in a subset of dry AMD patients. There are no treatments for Stargardt disease. The present invention identified non-retinoid RBP4 antagonists that are useful for the treatment of dry AMD and other conditions characterized by excessive accumulation of lipofuscin. Without wishing to be bound by any scientific theory, as accumulation of lipofuscin seems to be a direct cause of RPE and photoreceptor demise in AMD and STGD retina, the compounds described herein are disease-modifying agents since they directly address the root cause of these diseases. The present invention provides novel methods of treatment that will preserve vision in AMD and Stargardt disease patients, and patients' suffering from conditions characterized by excessive accumulation of lipofuscin.

REFERENCES

1. Petrukhin K. New therapeutic targets in atrophic age-related macular degeneration. Expert Opin. Ther. Targets. 2007, 11(5): 625-639
2. C. Delori, D. G. Goger and C. K. Dorey, Age-related accumulation and spatial distribution of lipofuscin in RPE of normal subjects. Investigative Ophthalmology and Visual Science 42 (2001), pp. 1855-1866
3. F. C. Delori, RPE lipofuscin in ageing and age-related macular degeneration. In: G. Coscas and F. C. Piccolino, Editors, Retinal Pigment Epithelium and Macular Disease (Documenta Ophthalmologica) vol. 62, Kluwer Academic Publishers, Dordrecht, The Netherlands (1995), pp. 37-45.
4. C. K. Dorey, G. Wu, D. Ebenstein, A. Garsd and J. J. Weiter, Cell loss in the aging retina. Relationship to lipofuscin accumulation and macular degeneration. Investigative Ophthalmology and Visual Science 30 (1989), pp. 1691-1699.
5. L. Feeney-Burns, E. S. Hilderbrand and S. Eldridge, Aging human RPE: morphometric analysis of macular, equatorial, and peripheral cells. Investigative Ophthalmology and Visual Science 25 (1984), pp. 195-200.
6. F. G. Holz, C. Bellman, S. Staudt, F. Schutt and H. E. Volcker, Fundus autofluorescence and development of geographic atrophy in age-related macular degeneration. Investigative Ophthalmology and Visual Science 42 (2001), pp. 1051-1056.
7. F. G. Holz, C. Bellmann, M. Margaritidis, F. Schutt, T. P. Otto and H. E. Volcker, Patterns of increased in vivo fundus autofluorescence in the junctional zone of geographic atrophy of the retinal pigment epithelium associated with age-related macular degeneration. Graefe's Archive for Clinical and Experimental Ophthalmology 237 (1999), pp. 145-152.
7. A. von Rückmann, F. W. Fitzke and A. C. Bird, Fundus autofluorescence in age-related macular disease imaged with a laser scanning ophthalmoscope. Investigative Ophthalmology and Visual Science 38 (1997), pp. 478-486.
9. F. G. Holz, C. Bellman, S. Staudt, F. Schutt and H. E. Volcker, Fundus autofluorescence and development of geographic atrophy in age-related macular degeneration. Investigative Ophthalmology and Visual Science 42 (2001), pp. 1051-1056.
10. Sparrow J R, Fishkin N, Zhou J, Cai B, Jang Y P, Krane S, Itagaki Y, Nakanishi K. A2E, a byproduct of the visual cycle. Vision Res. 2003 December; 43(28):2983-90
11. Radu R A, Han Y, Bui T V, Nusinowitz S, Bok D, Lichter J, Widder K, Travis G H, Mata N L. Reductions in serum vitamin A arrest accumulation of toxic retinal fluorophores: a potential therapy for treatment of lipofuscin-based retinal diseases. Invest Ophthalmol Vis Sci. 2005 December; 46(12):4393-401
12. Motani A, Wang Z, Conn M, Siegler K, Zhang Y, Liu Q, Johnstone S, Xu H, Thibault S, Wang Y, Fan P, Connors R, Le H, Xu G, Walker N, Shan B, Coward P. Identification and characterization of a non-retinoid ligand for retinol-binding protein 4 which lowers serum retinol-binding protein 4 levels in vivo. J Biol Chem. 2009 Mar. 20; 284(12):7673-80.
13. Berni R, Formelli F. In vitro interaction of fenretinide with plasma retinol-binding protein and its functional consequences. FEBS Lett. 1992 Aug. 10; 308(1):43-5.
14. Schaffer E M, Ritter S J, Smith J R. N-(4-hydroxyphenyl)retinamide (fenretinide) induces retinol-binding protein secretion from liver and accumulation in the kidneys in rats. J Nutr. 1993 September; 123(9):1497-503
15. Adams W R, Smith J E, Green M H. Effects of N-(4-hydroxyphenyl)retinamide on vitamin A metabolism in rats. Proc Soc Exp Biol Med. 1995 February; 208(2):178-85.
16. Puduvalli V K, Saito Y, Xu R, Kouraklis G P, Levin V A, Kyritsis A P. Fenretinide activates caspases and induces apoptosis in gliomas. Clin Cancer Res. 1999 August; 5(8):2230-5
17. Holmes W F, Soprano D R, Soprano K J. Synthetic retinoids as inducers of apoptosis in ovarian carcinoma cell lines. J Cell Physiol. 2004 June; 199(3):317-29
18. Simeone A M, Ekmekcioglu S, Broemeling L D, Grimm E A, Tari A M. A novel mechanism by which N-(4-hydroxyphenyl)retinamide inhibits breast cancer cell growth: the production of nitric oxide. Mol Cancer Ther. 2002 October; 1(12):1009-17
19. Fontana J A, Rishi A K. Classical and novel retinoids: their targets in cancer therapy. Leukemia. 2002 April; 16(4):463-72
20. Samuel W, Kutty R K, Nagineni S, Vijayasarathy C, Chandraratna R A, Wiggert B. N-(4-hydroxyphenyl)retinamide induces apoptosis in human retinal pigment epithelial cells: retinoic acid receptors regulate apoptosis, reactive oxygen species generation, and the expression of heme oxygenase-1 and Gadd153. J Cell Physiol. 2006 December; 209(3):854-65
21. Fontana J A, Rishi A K. Classical and novel retinoids: their targets in cancer therapy. Leukemia. 2002 April; 16(4):463-72
22. Samuel W, Kutty R K, Nagineni S, Vijayasarathy C, Chandraratna R A, Wiggert B. N-(4-hydroxyphenyl)retinamide induces apoptosis in human retinal pigment epithelial cells: retinoic acid receptors regulate apoptosis, reactive oxygen species generation, and the expression of heme oxygenase-1 and Gadd153. J Cell Physiol. 2006 December; 209(3):854-65
23. Sabichi A L, Xu H, Fischer S, Zou C, Yang X, Steele V E, Kelloff G J, Lotan R, Clifford J L. Retinoid receptor-dependent and independent biological activities of novel fenretinide analogues and metabolites. Clin Cancer Res. 2003 Oct. 1; 9(12):4606-13
24. Clifford J L, Menter D G, Wang M, Lotan R, Lippman S M. Retinoid receptor-dependent and -independent effects of N-(4-hydroxyphenyl)retinamide in F9 embryonal carcinoma cells. Cancer Res. 1999 Jan. 1; 59(1):14-8.
25. Gollapalli D R, Rando R R. The specific binding of retinoic acid to RPE65 and approaches to the treatment of macular degeneration. Proc Natl Acad Sci USA. 2004 Jul. 6; 101(27):10030-5
26. Maiti P, Kong J, Kim S R, Sparrow J R, Allikmets R, Rando R R. Small molecule RPE65 antagonists limit the visual cycle and prevent lipofuscin formation. Biochemistry. 2006 Jan. 24; 45(3):852-60
27. Radu R A, Mate N L, Nusinowitz S, Liu X, Sieving P A, Travis G H. Treatment with isotretinoin inhibits lipofuscin accumulation in a mouse model of recessive Stargardt's macular degeneration. Proc Natl Acad Sci USA. 2003 Apr. 15; 100(8):4742-7
28. Monaco H L, Rizzi M, Coda A. Structure of a complex of two plasma proteins: transthyretin and retinol-binding protein. Science. 1995 May 19; 268(5213):1039-41.
29. Bonanni B, Lazzeroni M, Veronesi U. Synthetic retinoid fenretinide in breast cancer chemoprevention. Expert Rev Anticancer Ther. 2007 April; 7(4):423-32.
30. Sunness J S, Margalit E, Srikumaran D, Applegate C A, Tian Y, Perry D, Hawkins R S, Bressler N M. The long-term natural history of geographic atrophy from age-related macular degeneration: enlargement of atrophy and implications for interventional clinical trials. Ophthalmology. 2007 February; 114(2):271-7.
31. Glickman J F et al. A comparison of ALPHAScreen, TR-FRET, and TRF as assay methods for FXR nuclear receptors. J. Biomol. Screening 2002; 7:3-10
32. Fujimura T et al. Unique properties of coactivator recruitment caused by differential binding of FK614, an anti-diabetic agent, to PPARgamma. Biol. Pharm. Bull. 2006; 29:423-429
33. Zhou G et al. Nuclear receptors have distinct affinities of coactivators: characterization by FRET. Mol. Endocrinol. 1998; 12:1594-1605
34. Cogan U, Kopelman M, Mokady S, Shinitzky M. Binding affinities of retinol and related compounds to retinol binding proteins. Eur J Biochem. 1976 May 17; 65(1):71-8.
35. Decensi A, Torrisi R, Polizzi A, Gesi R, Brezzo V, Rolando M, Rondanina G, Orengo M A, Formelli F, Costa A. Effect of the synthetic retinoid fenretinide on dark adaptation and the ocular surface. J Natl Cancer Inst. 1994 Jan. 19; 86(2):105-10.
36. Conley B, O'Shaughnessy J, Prindiville S, Lawrence J, Chow C, Jones E, Merino M J, Kaiser-Kupfer M I, Caruso R C, Podgor M, Goldspiel B, Venzon D, Danforth D, Wu S, Noone M, Goldstein J, Cowan K H, Zujewski J. Pilot trial of the safety, tolerability, and retinoid levels of N-(4-hydroxyphenyl) retinamide in combination with tamoxifen in patients at high risk for developing invasive breast cancer. J. Clin Oncol. 2000 January; 18(2):275-83.
37. Fain G L, Lisman J E. Photoreceptor degeneration in vitamin A deprivation and retinitis pigmentosa: the equivalent light hypothesis. Exp Eye Res. 1993 September; 57(3):335-40.
38. Makimura H, Wei J, Dolan-Looby S E, Ricchiuti V, Grinspoon S. Retinol-Binding Protein Levels are Increased in Association with Gonadotropin Levels in Healthy Women. Metabolism. 2009 April; 58(4): 479-487.
39. Yang Q, Graham T E, Mody N, Preitner F, Peroni O D, Zabolotny J M, Kotani K, Quadro L, Kahn B B. Serum retinol binding protein 4 contributes to insulin resistance in obesity and type 2 diabetes. Nature. 2005 Jul. 21; 436(7049):356-62.
40. Kim S R, Jang Y P, Jockusch S, Fishkin N E, Turro N J, Sparrow J R. The all-trans-retinal dimer series of lipofuscin pigments in retinal pigment epithelial cells in a recessive Stargardt disease model. PNAS. Dec. 4, 2007, Vol. 104, No. 49, 19273-8.
41. Wu Y, Fishkin N E, Pande A, Pande J, Sparrow R J. Novel Lipofuscin Bisretinoids Prominent in Human Retina and in a Model of Recessive Stargardt Disease. Journal of Biological Chemistry. Jul. 24, 2009, Vol. 284, No. 30, 20155-20166.
42. E. G. Holz, C. Hellmann, M. Margaritidis, F. Schutt, T. P. Otto and H. E. Volcker, Patterns of increased in vivo fundus autofluorescence in the junctional zone of geographic atrophy of the retinal pigment epithelium associated with age-related macular degeneration. Graefe's Archive for Clinical and Experimental Ophthalmology 237 (1999), pp. 145-152.
43. Larsen, T. M. et al. PPARgamma agonists in the treatment of type II diabetes: is increased fatness commensurate with long-term efficacy? International Journal of Obesity (2003), 27, 147-161.
44. Lehmann D F, Lohray B B. A lesson in moderation: Applying pharmacodynamics to clarify the relationship between thiazolidinediones and adverse vascular outcomes in type 2 diabetes. J Clin Pharmacol. 2008; 48(8): 999-1002.
45. Rosenson R S, Wright R S, Farkouh M, Plutzky J. Modulating peroxisome proliferator-activated receptors for therapeutic benefit? Biology, clinical experience, and future prospects. American heart journal. 2012; 164(5): 672-680.
46. Nissen S E, Wolski K, Topol E J. Effect of muraglitazar on death and major adverse cardiovascular events in patients with type 2 diabetes mellitus. Jama. 2005; 294 (20); 2581-2586.
47. Nissen S E. Perspective: effect of rosiglitazone on cardiovascular outcomes. Current cardiology reports. 2007; 9(5):343-344.

What is claimed is:

1. A compound having the structure:

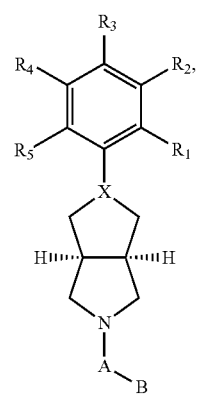

wherein

R₁, R₂, R₃, R₄, and R₅ are each independently H, halogen, alkyl, haloalkyl, O-haloalkyl, aryl or heteroaryl;
X is N or CR₆,
  wherein Re is H, OH, or halogen;
A is absent or present, and when present is

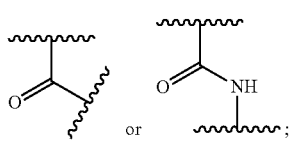

B has the structure:

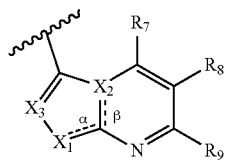

wherein
α and β are each a bond that is present or absent;
X₁ is N, NH or NR₁₀,
  wherein R₁₀ is alkyl, alkenyl or alkynyl;
X₂ is C or N;
X₃ is CH or N;
R₇, R₈ and R₉ are each, independently, H, halogen, alkyl, alkenyl, alkynyl, alkyl-OH, alkyl-NH₂, alkyl-OAc alkyl-O(CO)-alkyl, alkyl-O-alkyl, haloalkyl, cycloalkyl, O-alkyl, NH-alkyl, C(O)OH, C(O)—NH₂, C(O)—N(CH₃)₂, C(O)—NHCH₃, NHC(O)—N(CH₃)₂, CN or CF₃,
wherein
  X₁, X₂ and X₃ are each N, α is present and β is absent; or
  X₁ is NH, X₂ is C, X₃ is CH, α is absent and β is present; or
  X₁ is N, X₂ is N, X₃ is CH, α is present and β is absent; or
  X₁ is NH or NR₁₀, X₂ is C, X₃ is N, α is absent and β is present, wherein when X₁ is NH, X₂ is C, X₃ is N, α is absent and β is present, then one of R₇, R₈ and R₉ is other than H,
or B has the structure:

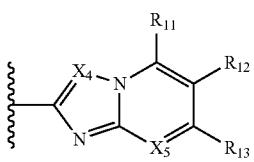

wherein
X₄ and X₅ are each, independently, is N or CH; and
R₁₁, R₁₂ and R₁₃ are each, independently, H, halogen, alkyl, alkenyl, alkynyl, alkyl-OH, alkyl-NH₂, alkyl-OAc, alkyl-O(CO)-alkyl, alkyl-O-alkyl, haloalkyl, cycloalkyl, O-alkyl, NH-alkyl, C(O)OH, C(O)—NH₂, C(O)—N(CH₃)₂, C(O)—NHCH₃, NHC(O)—N(CH₃)₂, CN or CF₃,
or a pharmaceutically acceptable salt thereof.

2. The compound of claim 1 having the structure:

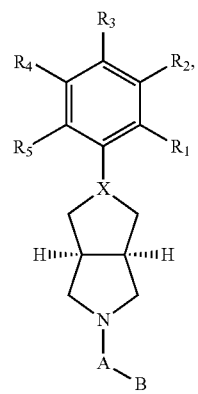

wherein
R₁, R₂, R₃, R₄, and R₅ are each independently H, halogen, CF₃ or C₁-C₄ alkyl;
X is N or CR₆,
  wherein Re is H, OH, or halogen;
A is absent or present, and when present is

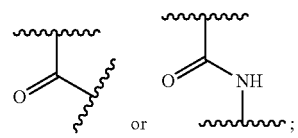

B has the structure:

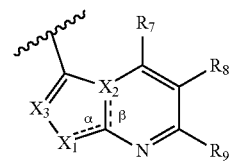

wherein
α and β are each a bond that is present or absent;
X₁ is N, NH or NR₁₀,
  wherein R₁₀ is alkyl, alkenyl or alkynyl;
X₂ is C or N;
X₃ is CH or N;
R₇, R₈ and R₉ are each, independently, H, halogen, alkyl, alkenyl, alkynyl, alkyl-OH, alkyl-NH₂, alkyl-OAc alkyl-O(CO)-alkyl, alkyl-O-alkyl, haloalkyl, cycloalkyl, O-alkyl, NH-alkyl, C(O)OH, C(O)—NH₂, C(O)—N(CH₃)₂, C(O)—NHCH₃, NHC(O)—N(CH₃)₂, CN or CF₃, wherein
  X₁, X₂ and X₃ are each N, α is present and β is absent; or
  X₁ is NH, X₂ is C, X₃ is CH, a is absent and β is present; or
  X₁ is N, X₂ is N, X₃ is CH, & is present and β is absent; or
  X₁ is NH or NR₁₀, X₂ is C, X₃ is N, α is absent and β is present, wherein when X₁ is NH, X₂ is C, X₃ is N,
  α is absent and β is present, then one of R₇, R₈ and R₉ is other than H, or B has the structure:

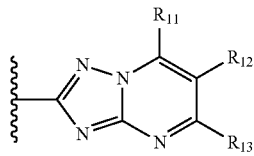

wherein

R$_{11}$, R$_{12}$ and R$_{13}$ are each, independently, H, halogen, alkyl, alkenyl, alkynyl, alkyl-OH, alkyl-NH$_2$, alkyl-OAc, alkyl-O(CO)-alkyl, alkyl-O-alkyl, haloalkyl, cycloalkyl, O-alkyl, NH-alkyl, C(O)OH, C(O)—NH$_2$, C(O)—N(CH$_3$)$_2$, C(O)—NHCH$_3$, NHC(O)—N(CH$_3$)$_2$, CN or CF$_3$, or a pharmaceutically acceptable salt thereof.

3. The compound of claim 1 having the structure:

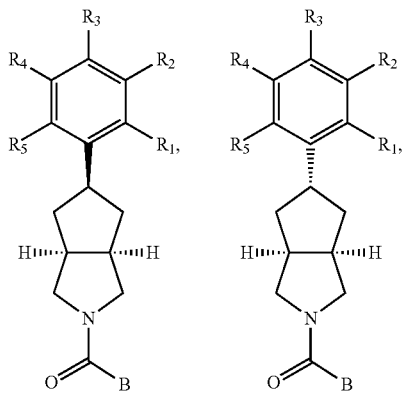

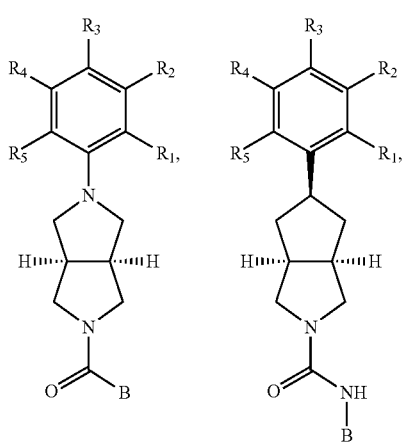

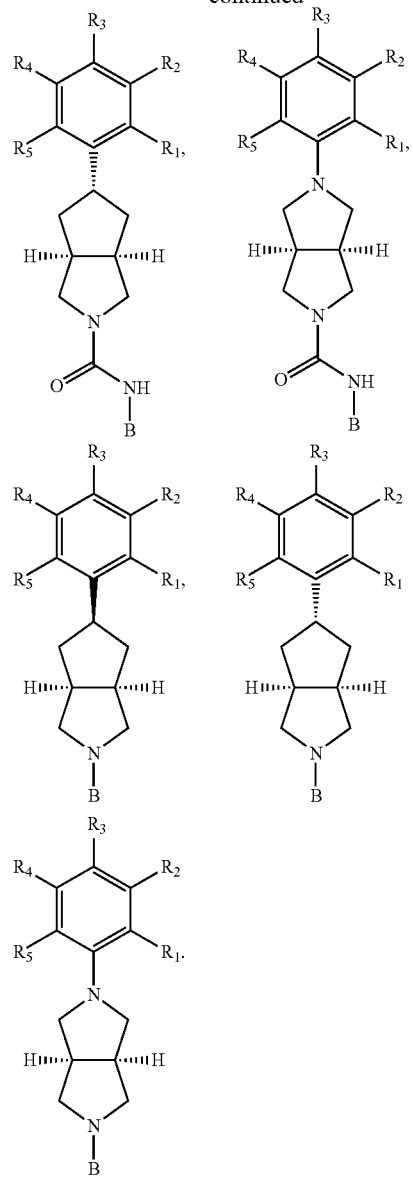

4. The compound of claim 1,
wherein one of R$_1$, R$_2$, R$_3$, R$_4$, and R$_5$ is other than H, or wherein two of R$_1$, R$_2$, R$_3$, R$_4$, and R$_5$ are other than H.

5. The compound of claim 1, wherein B has the structure:

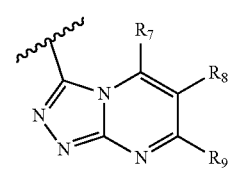

R$_7$, R$_8$ and R$_9$ are each, independently, H, halogen, alkyl, alkyl-OH, alkyl-NH$_2$, alkyl-OAc, alkyl-O-alkyl, haloalkyl, cycloalkyl, O-alkyl, NH-alkyl, C(O)OH, C(O)—NH$_2$, C(O)—N(CH$_3$)$_2$, C(O)—NHCH$_3$, NHC(O)—N(CH$_3$)$_2$, CN, or CF$_3$.

6. The compound of claim 5, wherein $R_7$, $R_8$ and $R_9$ are each, independently, H, Cl, Br, F, $OCH_3$, $OCH_2CH_3$, $CF_3$, CN, $CH_3$, $CH_3CH_3$, C(O)OH or C(O)—$NH_2$, or $R_7$, $R_8$ and $R_9$ are each, independently, H, $CH_2CH_2OH$, $CH_2CH_2OCH_3$, $CH_2CH_2OAc$, $CH_2CH_2Cl$, $CH_2CH_2F$ or $CH_2CH_2Br$, or $R_7$, $R_8$ and $R_9$ are each, independently, H, halogen or alkyl, or two of $R_7$, Re and Ry are each H and the remaining one of $R_7$, $R_8$ and $R_9$ is other than H; or wherein one of $R_7$, $R_8$ and $R_9$ is H and the remaining two of $R_7$, Re and Ry are each other than H.

7. The compound of claim 5, wherein B has the structure:

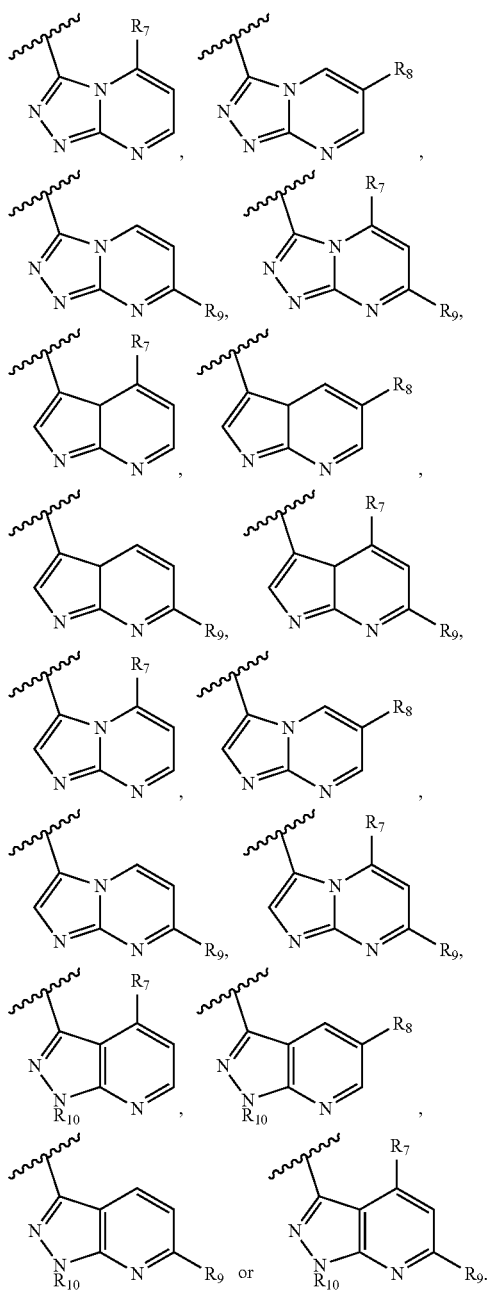

8. The compound of claim 1, wherein B has the structure:

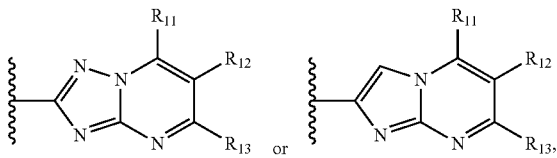

wherein $R_{11}$, $R_{12}$ and $R_{13}$ are each, independently, H, halogen, alkyl, alkyl-OH, alkyl-$NH_2$, alkyl-OAc, alkyl-O-alkyl, haloalkyl, cycloalkyl, O-alkyl, NH-alkyl, C(O)OH, C(O)—$NH_2$, C(O)—$N(CH_3)_2$, C(O)—$NHCH_3$, NHC(O)—$N(CH_3)_2$, CN, or $CF_3$, or $R_{11}$, $R_{12}$ and $R_{13}$ are each, independently, H, Cl, Br, F, $OCH_3$, $OCH_2CH_3$, $CF_3$, CN, $CH_3$, $CH_3CH_3$, C(O)OH or C(O)—$NH_2$, or $R_{11}$, $R_{12}$ and $R_{13}$ are each, independently, H, $CH_2CH_2OH$, $CH_2CH_2OCH_3$, $CH_2CH_2OAc$, $CH_2CH_2Cl$, $CH_2CH_2F$ or $CH_2CH_2Br$, or two of $R_{11}$, $R_{12}$ and $R_{13}$ are each H and the remaining one of $R_{11}$, $R_{12}$ and $R_{13}$ is other than H; or wherein one of $R_{11}$, $R_{12}$ and $R_{13}$ is H and the remaining two of $R_{11}$, $R_{12}$ and $R_{13}$ are each other than H.

9. The compound of claim 8, wherein B has the structure:

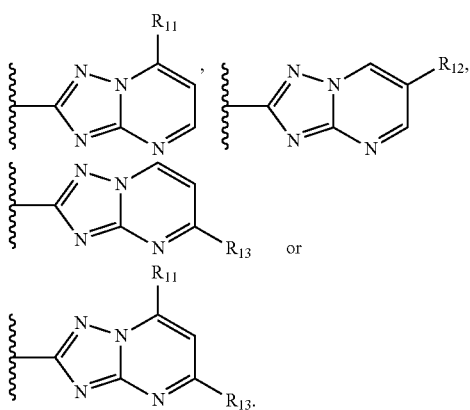

10. The compound of claim 1 having the structure:

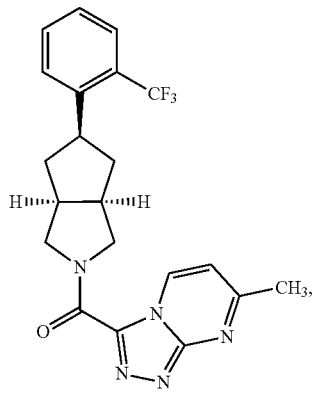

69
-continued
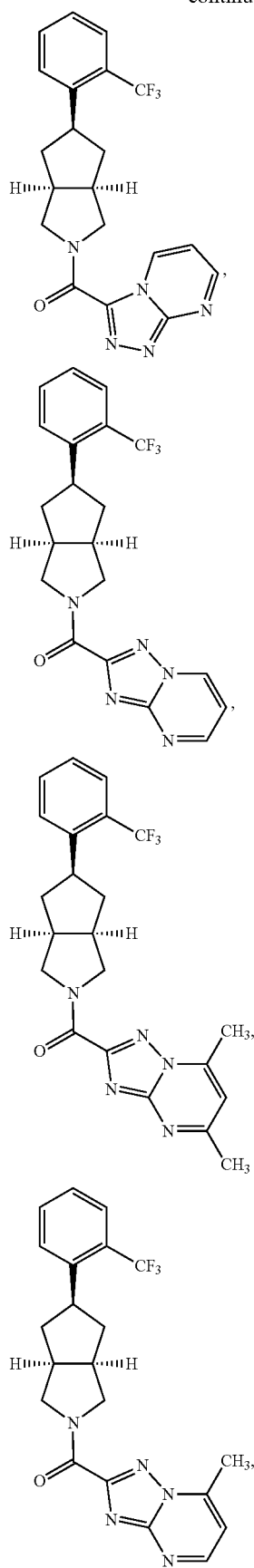
70
-continued
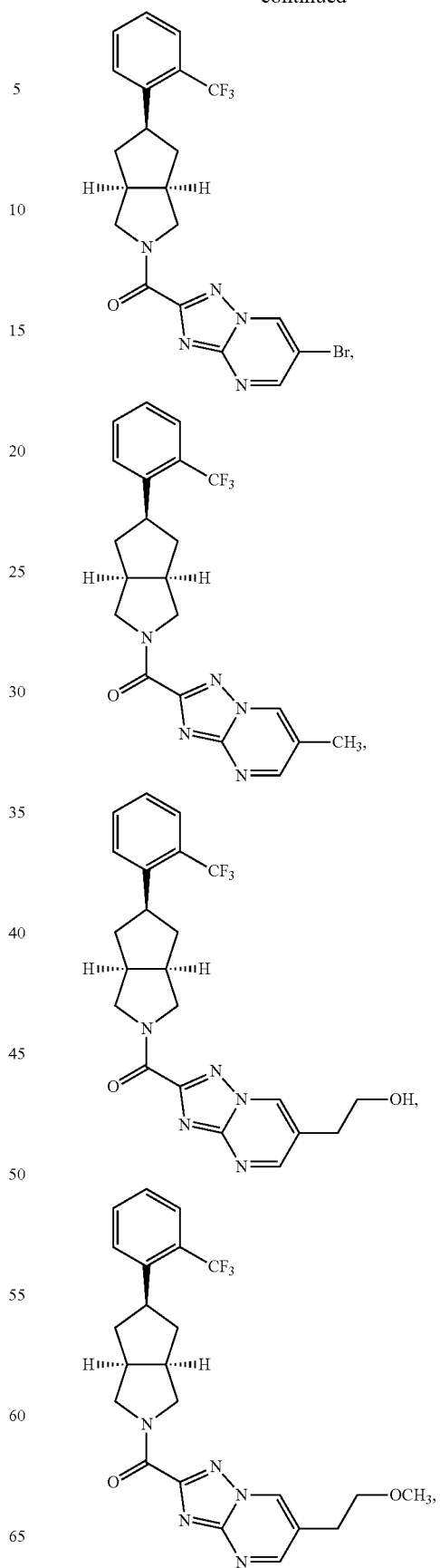

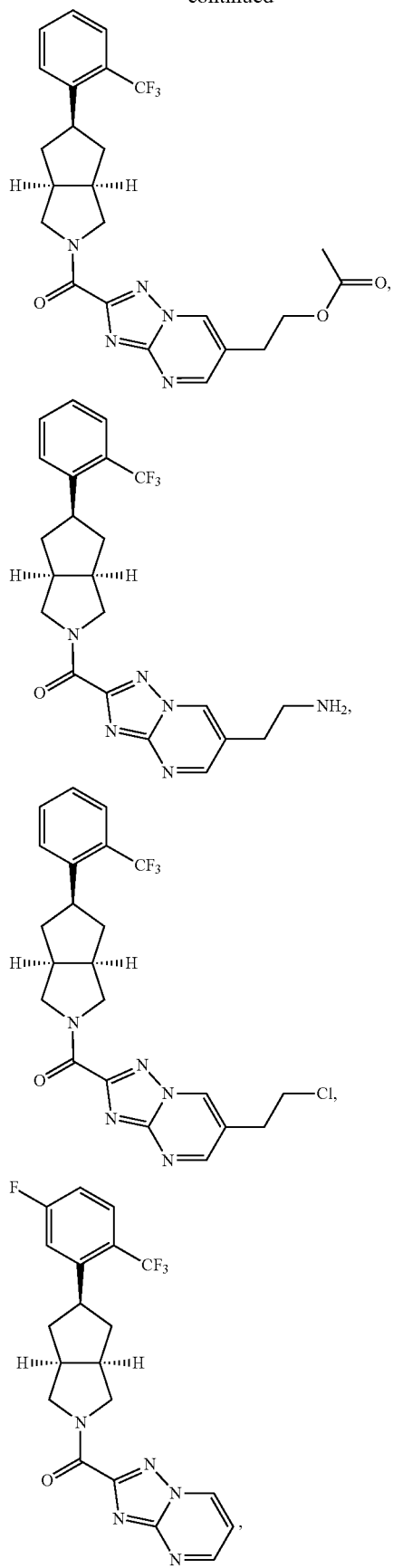
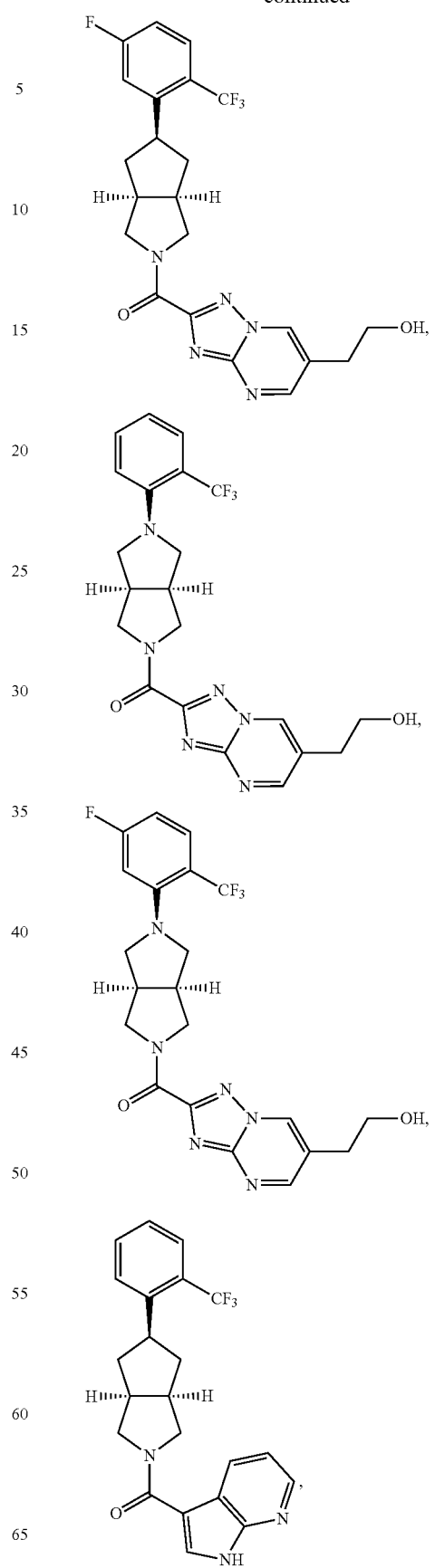

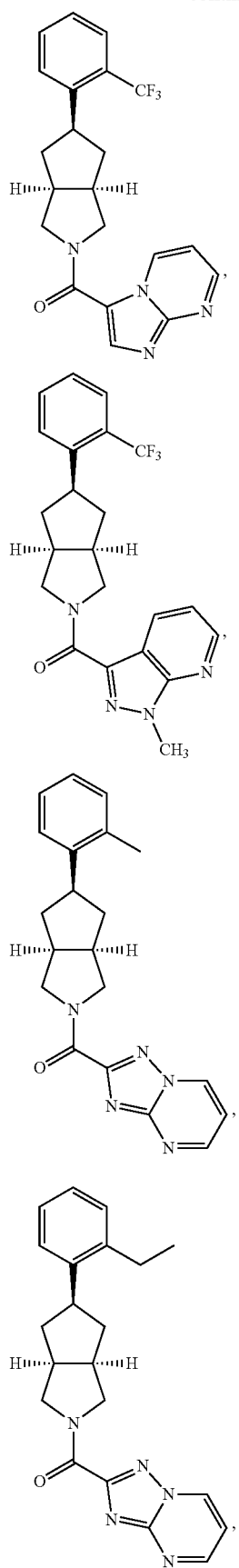
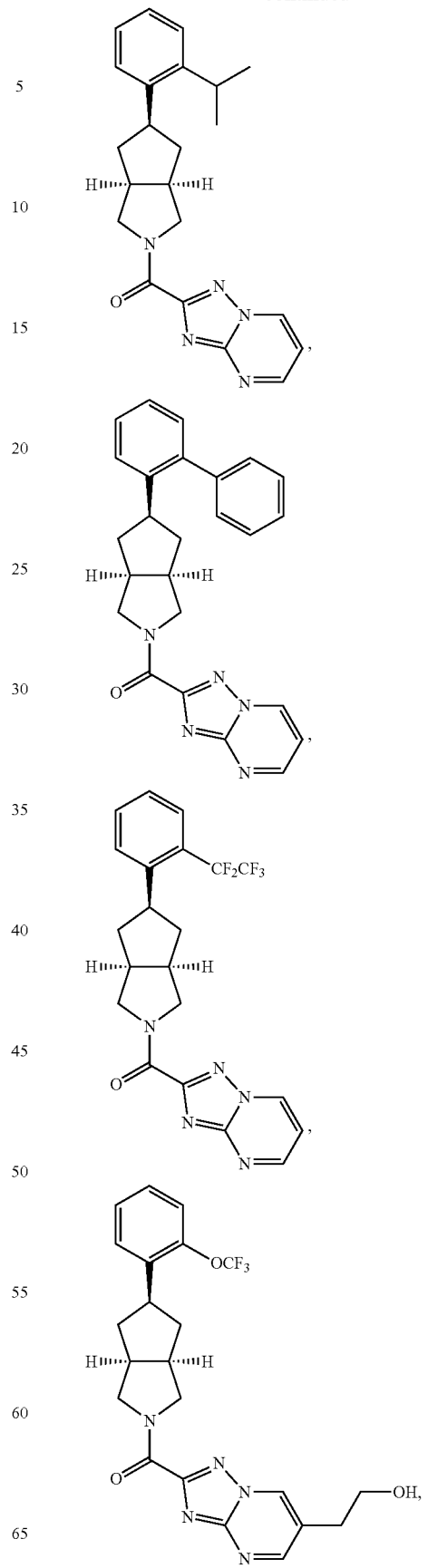

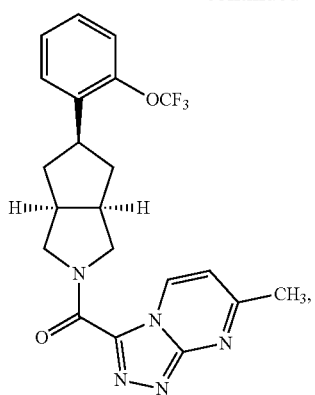

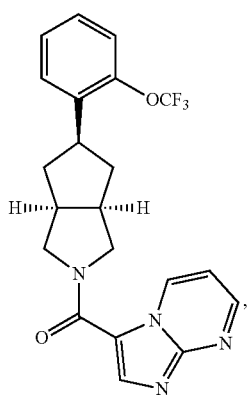

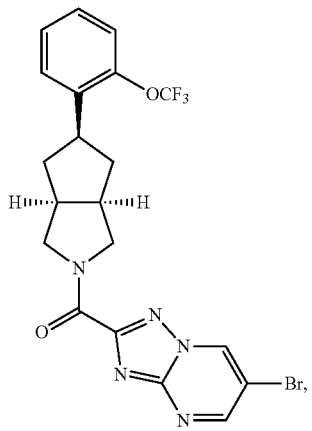

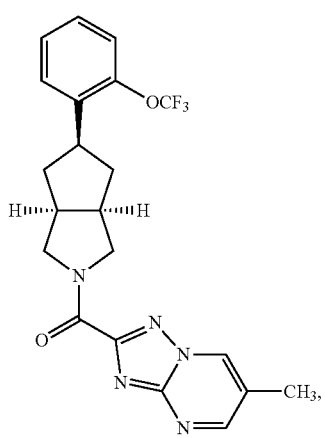

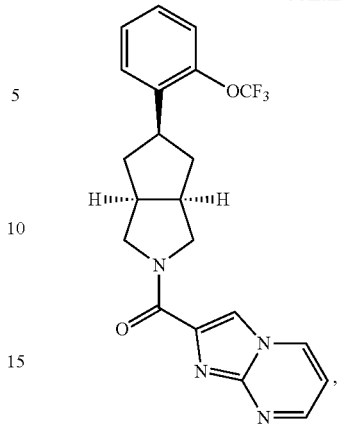

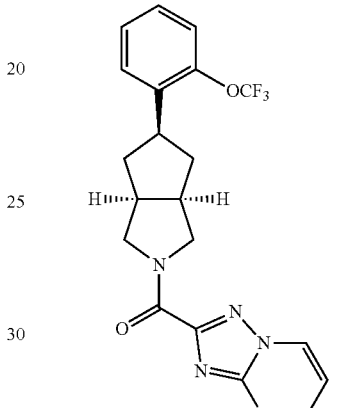

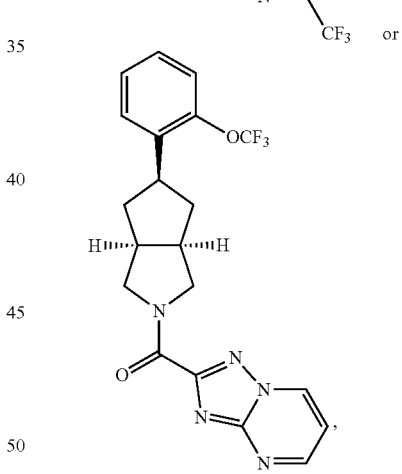

or a pharmaceutically acceptable salt thereof.

11. A pharmaceutical composition comprising the compound of claim 1 and a pharmaceutically acceptable carrier.

12. A method for treating a disease characterized by excessive lipofuscin accumulation in the retina in a mammal afflicted therewith comprising administering to the mammal an effective amount of a compound of claim 1,
   wherein the disease characterized by excessive lipofuscin accumulation in the retina is Age-Related Macular Degeneration, dry (atrophic) Age-Related Macular Degeneration, Stargardt Disease, Best disease, adult vitelliform maculopathy or Stargardt-like macular dystrophy.

13. The method of claim 12, wherein the amount of the compound is effective to lower the serum concentration of RBP4 in the mammal or to lower the retinal concentration of a bisretinoid in lipofuscin in the mammal without substantially activating PPAR gamma in the mammal.

14. The method of claim 13, wherein the bisretinoid is A2E, isoA2E, A2-DHP-PE or atRAL di-PE.

15. The compound of 8, wherein $R_1$, $R_2$, $R_3$, $R_4$, and $R_5$ are each H, methyl, ethyl, phenyl, t-Bu, i-Pr, $OCF_3$, $CF_3$, $OCF_2CF_3$, $CF_2CF_3$, Cl, Br, or F.

16. The compound of claim 1, wherein B has the structure:

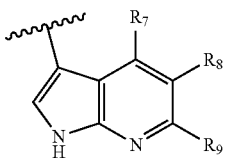

$R_7$, $R_8$ and $R_9$ are each, independently, H, halogen, alkyl, alkyl-OH, alkyl-$NH_2$, alkyl-OAc, alkyl-O-alkyl, haloalkyl, cycloalkyl, O-alkyl, NH-alkyl, C(O)OH, C(O)—$NH_2$, C(O)—N($CH_3$)$_2$, C(O)—NH$CH_3$, NHC(O)—N($CH_3$)$_2$, CN, or $CF_3$.

17. The compound of claim 1, wherein B has the structure:

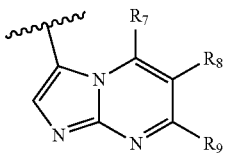

18. The compound of claim 1, wherein B has the structure:

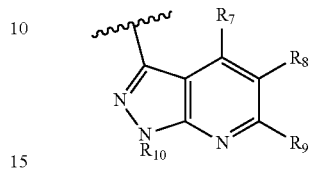

$R_7$, $R_8$ and $R_9$ are each, independently, H, halogen, alkyl, alkyl-OH, alkyl-$NH_2$, alkyl-OAc, alkyl-O-alkyl, haloalkyl, cycloalkyl, O-alkyl, NH-alkyl, C(O)OH, C(O)—$NH_2$, C(O)—N($CH_3$)$_2$, C(O)—NH$CH_3$, NHC(O)—N($CH_3$)$_2$, CN, or $CF_3$.

$R_7$, $R_8$ and $R_9$ are each, independently, H, halogen, alkyl, alkyl-OH, alkyl-$NH_2$, alkyl-OAc, alkyl-O-alkyl, haloalkyl, cycloalkyl, O-alkyl, NH-alkyl, C(O)OH, C(O)—$NH_2$, C(O)—N($CH_3$)$_2$, C(O)—NH$CH_3$, NHC(O)—N($CH_3$)$_2$, CN, or $CF_3$; and $R_{10}$ is alkyl, alkenyl or alkynyl.

19. The compound of claim 9, wherein X is N or CH.

20. The compound of claim 9, wherein
(a) $R_1$, $R_2$, $R_3$, $R_4$, and $R_5$ are each H, t-Bu, Cl, Br, F or $CF_3$;
(b) $R_1$, $R_2$, $R_3$, $R_4$, and $R_5$ are each H, methyl, ethyl, phenyl, t-Bu, i-Pr, $OCF_3$, $CF_3$, $OCF_2CF_3$, $CF_2CF_3$, Cl, Br, or F;
(c) $R_1$, $R_2$, $R_3$, and $R_4$ are each H; $R_5$ is —H, $OCF_3$, $CF_2CF_3$, methyl, ethyl, i-Pr or phenyl;
(d) $R_1$, $R_3$ and $R_4$ are each H; $R_2$ is halogen; $R_5$ is $CF_3$ or t-Bu; or
(e) $R_1$, $R_2$, $R_3$, and $R_4$ are each H; $R_5$ is $CF_3$ or t-Bu.

* * * * *